(12) United States Patent
Shimizu et al.

(10) Patent No.: US 10,954,222 B2
(45) Date of Patent: Mar. 23, 2021

(54) BENZOTHIOPHENE COMPOUND, ALTERNATIVE AUTOPHAGY-INDUCING AGENT AND ANTICANCER AGENT INCLUDING THE COMPOUND AS ACTIVE INGREDIENT, AND METHOD FOR SCREENING FOR COMPOUND HAVING ANTICANCER ACTIVITY

(71) Applicant: National University Corporation Tokyo Medical and Dental University, Tokyo (JP)

(72) Inventors: Shigeomi Shimizu, Bunkyo-ku (JP); Takamitsu Hosoya, Bunkyo-ku (JP); Michiko Murohashi, Bunkyo-ku (JP); Suguru Yoshida, Bunkyo-ku (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 316 days.

(21) Appl. No.: 14/376,671

(22) PCT Filed: Feb. 7, 2013

(86) PCT No.: PCT/JP2013/052947
§ 371 (c)(1),
(2) Date: Aug. 5, 2014

(87) PCT Pub. No.: WO2013/118842
PCT Pub. Date: Aug. 15, 2013

(65) Prior Publication Data
US 2015/0056141 A1  Feb. 26, 2015

(30) Foreign Application Priority Data

Feb. 9, 2012 (JP) .............................. JP2012-026373
Feb. 9, 2012 (JP) .............................. JP2012-026377

(51) Int. Cl.
*A61K 49/00* (2006.01)
*C07D 409/04* (2006.01)
*C07D 333/68* (2006.01)
*G01N 33/50* (2006.01)
*A61K 31/381* (2006.01)

(52) U.S. Cl.
CPC .......... *C07D 409/04* (2013.01); *A61K 31/381* (2013.01); *A61K 49/0008* (2013.01); *C07D 333/68* (2013.01); *G01N 33/5011* (2013.01); *G01N 2500/04* (2013.01)

(58) Field of Classification Search
CPC ............................ C07D 409/04; C07D 333/68; A61K 49/0008; G01N 33/5011; G01N 2500/04

USPC .......................................................... 424/9.2
See application file for complete search history.

(56) References Cited

U.S. PATENT DOCUMENTS

| 5,972,639 | A  | * | 10/1999 | Parandoosh | C12Q 1/42 435/29 |
|---|---|---|---|---|---|
| 6,268,137 | B1 | * | 7/2001 | Szyf | C07H 21/00 435/375 |
| 2006/0058371 | A1 | * | 3/2006 | Callahan et al. | 514/443 |
| 2008/0269259 | A1 | * | 10/2008 | Thompson et al. | 514/263.4 |
| 2009/0099072 | A1 | | 4/2009 | Geneste et al. | |
| 2011/0038880 | A1 | | 2/2011 | Katayama et al. | |
| 2011/0124104 | A1 | * | 5/2011 | Gudkov et al. | 435/375 |

FOREIGN PATENT DOCUMENTS

| JP | 2007-153792 A |   | 6/2007 |
|---|---|---|---|
| JP | 2007153792 A | * | 6/2007 |
| JP | 2008-532486 A |   | 8/2008 |
| WO | 2009/123145 A1 |   | 10/2009 |

OTHER PUBLICATIONS

Falcon-Perez et al. J. Cell Sci. 2015, 5243-5255.*
Buzzai et al. Cancer Res. 2007, 6745-6752.*
Chen et al. Mol. Cancer Ther. 2012, 370-382.*
Fabre et al. Cell Cycle 2008 7: 2139-2145.*

(Continued)

*Primary Examiner* — Michael G. Hartley
*Assistant Examiner* — Sean R Donohue
(74) *Attorney, Agent, or Firm* — Sughrue Mion, PLLC

(57) ABSTRACT

It has been found that efficient screening for a compound having anticancer activity can be achieved by selecting a compound having activity to induce alternative autophagy using, as an index, formation of fluorescent bright spots due to aggregation of a lysosomal protein to which a fluorescent protein is attached in cells expressing the lysosomal protein. In addition, it has been found that a benzothiophene compound represented by the following general formula (1) has alternative autophagy-inducing activity and anticancer activity:

[Chem. 1]

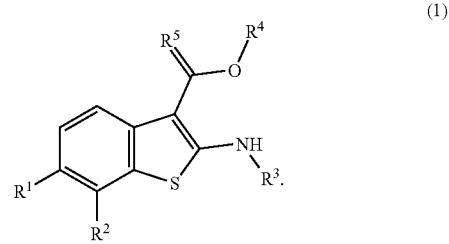

(1)

7 Claims, 9 Drawing Sheets

(56) References Cited

OTHER PUBLICATIONS

Yu et al. Nature, 2010, 942-947.*
Hundeshagen et al. B<C Biology, 2011, 1-15.*
Garcia-Escudero et al. Autophagy 2008, 923-925.*
Nishida et al. Nature Lett. 2009, S1-S21.*
Lefranc et al. The Oncologist 2007, 1295-1403.*
Papandreou et al. Cell Death Diff. 2008, 15, 1572-1581.*
Lee et al. DNA and Cell Biol. 2007, 713-720.*
Communication dated Jul. 8, 2015, issued by the European Patent Office in corresponding European Application No. 13746448.3.
Kapustina et al., "Synthesis 6-Formylbenzo(b)Thiophene Derivatives and their Antiviral Activity", S. Ordzhonikidze All-Union Scientific-Research Chemical Pharmaceutical Institute, 1991, pp. 789 (1 pg. total), XP-002736471, Retrieved from the Internet: URL:http://download.springer.com/static/pdf/912/art%253A10.1007%252FBF00767259.pdf?auth66=1424870939_86319c107f68919a57a45a2d3f590b24&ext=.pdf [retrieved Feb. 25, 2015].
Grinev et al., "Synthesis of Derivatives of 2-Acylamino-7-Oxybenzo[b]Thiophene. Bromination and Nitration", S. Ordzhonikidze All-Union Scientific-Research Institute of Pharmaceutical Chemistry, 1987, pp. 384 (1 pg. total), XP-002736470, Retrieved from the Internet: URL:http://download.springer.com/static/pdf/335/art%253A10.1007%252FBF00546729.pdf?auth66=1424869408_f9d9f334d427964134d5919b7a7d6450&ext=.pdf [retrieved Feb. 25, 2015].
Communication dated Jul. 24, 2015, issued by the European Patent Office in corresponding European Application No. 13746448.3.
Yuya Nishida et al., "Discovery of Atg5/Atg7-independent alternative macroautophagy", Nature, 2009, pp. 654-658, vol. 461, No. 7264.
Yoshihiro Inami et al., "Persistent activation of Nrf2 through p62 in hepatocellular carcinoma cells", Journal of Cell Biology, 2011, pp. 275-284, vol. 193, No. 2.
International Search Report for PCT/JP2013/052947 dated Apr. 2, 2013.
Wang et al., "Role of death receptor and mitochondrial pathways in conventional chemotherapy drug induction of apoptosis," Cell Signal., 2006, 18: 1528-35.
Katayama et al. "DNA damaging agent-induced autophagy produces a cytoprotective adenosine triphosphate surge in malignant glioma cells," Cell Death Differ., 2007, 14: 548-58.

\* cited by examiner

BENZOTHIOPHENE COMPOUND, ALTERNATIVE AUTOPHAGY-INDUCING AGENT AND ANTICANCER AGENT INCLUDING THE COMPOUND AS ACTIVE INGREDIENT, AND METHOD FOR SCREENING FOR COMPOUND HAVING ANTICANCER ACTIVITY

CROSS REFERENCE TO RELATED APPLICATIONS

This application is a National Stage of International Application No. PCT/JP2013/052947 filed Feb. 7, 2013, claiming priority based on Japanese Patent Application Nos. 2012-026373 filed Feb. 9, 2012 and 2012-026377 filed Feb. 9, 2012, the contents of all of which are incorporated herein by reference in their entireties.

TECHNICAL FIELD

The present invention relates to a benzothiophene compound, and an alternative autophagy-inducing agent and an anticancer agent comprising the compound as an active ingredient. The present invention also relates to a method for inducing alternative autophagy and a method for treating cancer using a benzothiophene compound. Furthermore, the present invention relates to a method for screening for a compound having anticancer activity.

BACKGROUND ART

Autophagy (macroautophagy) is an intracellular cleaning mechanism for degrading intracellular components such as organelles. It is known that, in autophagy, an organelle or the like is surrounded by a double membrane (isolation membrane), and then the isolation membrane is closed and further fuses with a lysosome to degrade the content such as an organelle. By analyses conducted so far, about 30 autophagy-related molecules were identified. Of these molecules, especially Atg5, Atg7, LC3, etc. were considered as molecules necessary for execution of autophagy.

However, the present inventors have recently found the presence of a novel autophagy (alternative autophagy) which does not require these molecules, but is originated from Golgi apparatus and endosomes, and is regulated by molecules such as Rab9 (NPL 1). Since the alternative autophagy is strongly induced by a cellular stress, a failure of this mechanism is assumed to be involved in induction of cancer and the like. For this reason, development of an anticancer agent utilizing the alternative autophagy is awaited, but has not been successfully achieved yet. Moreover, under the current situation, an approach for screening for a candidate compound for such an anticancer agent has not been developed yet.

Meanwhile, regarding benzothiophene compounds, it is disclosed that benzothiophene compounds in which the substituent at the 2-position is an acetamide group or the like and the substituent at the 6-position is a hydrogen or halogen atom have DNA methyltransferase-inhibitory activity and cancer growth-inhibitory effect (PTL 1). However, no benzothiophene compound having alternative autophagy-inducing activity has been identified yet.

CITATION LIST

Patent Literature

[PTL 1] Japanese Unexamined Patent Application Publication No. 2007-153792

Non Patent Literature

[NPL 1] Nishida Yuya, Arakawa Satoko, Shimizu Shigeomi, et al., Nature, Oct. 1, 2009, Vol. 461, No. 7264, pp. 654 to 658

SUMMARY OF INVENTION

Technical Problem

The present invention has been made in view of the above-described problems of the conventional technologies, and an object of the present invention is to provide an efficient method for screening for a compound having anticancer activity using activity to induce alternative autophagy as an index. Moreover, another object of the present invention is to provide a benzothiophene compound useful as an alternative autophagy-inducing agent and an anticancer agent, and a method for treating cancer.

Solution to Problem

To achieve the above-described objects, the present inventors first designed a system in which test compounds are brought into contact with Atg5-deficient cells expressing a lysosomal protein Lamp1 to which a fluorescent protein is attached, and a compound having activity to induce alternative autophagy is selected by using, as an index, formation of fluorescent bright spots due to aggregation of the lysosomal protein. Then, by actually using this system, compounds having activity to induce alternative autophagy were selected from as much as 11588 test compounds. Further, from these compounds, compounds which did not induce cell death of primary cultured cells, but which were capable of inducing cell death of immortalized cells (cancer cells) were selected. Moreover, the selected compounds were introduced into cancer-bearing non-human animals, and evaluated for anticancer activity by using, as an index, the size of the cancer borne by the cancer-bearing non-human animals. Thus, multiple compounds having anticancer activity were identified.

Subsequently, by using cancer-bearing non-human animals, the present inventors evaluated the anticancer activity of compounds found to have activity to induce alternative autophagy by using the formation of the fluorescent bright spots as an index and compounds found not to have the activity. As a result, the compounds not having the activity to induce alternative autophagy were found to have no anticancer activity at all, whereas almost all the compounds having activity to induce alternative autophagy were found to have anticancer activity.

Based on these facts, the present inventors have found that the use of the system in which activity to induce alternative autophagy is evaluated by using the formation of fluorescent bright spots as an index makes it possible to conduct efficient screening for a compound having anticancer activity. This finding has led to the completion of the screening method of the present invention.

Furthermore, the present inventors conducted the screening, and consequently have found that 2-acetamido-6- bromo-7-(2-(N,N-diethylamino)ethoxy)benzo[b]thiophene-3-carboxylic acid ethyl ester (ethyl 2-acetylamino-6-bromo-7-[2-(N,N-diethylamino)ethyloxy]benzo[b]thiophene-3-carboxylate) has activity to induce alternative autophagy. Moreover, it is found that the compound also has cell death-inducing activity and anticancer activity. In addition, the compound and analogous compounds thereof were investigated for activity to induce alternative autophagy and anticancer activity. As a result, it was also found that benzothiophene compounds having no alternative autophagy-inducing activity had no anticancer activity, whereas almost all benzothiophene compounds having alternative autophagy-inducing activity had anticancer activity.

Moreover, based on these findings, the present inventors synthesized novel benzothiophene compounds in which the substituent at the 2-position was an amino group, and the substituent at the 6-position was a halogen atom, and novel benzothiophene compounds in which the substituent at the 2-position was an acetamide group or the like, and the substituent at the 6-position was an aromatic carbon ring or the like, and evaluated the alternative autophagy-inducing activity of these compounds. As a result, the present inventors have found that these compounds had the activity, and this finding has led to the completion of the present invention.

Accordingly, the present invention relates to a benzothiophene compound and an alternative autophagy-inducing agent and an anticancer agent comprising the compound as an active ingredient. Moreover, the present invention relates to a method for inducing alternative autophagy and a method for treating cancer using a benzothiophene compound. Furthermore, the present invention relates to a method for screening for a compound having anticancer activity. More specifically, the following invention is provided.

<1> An alternative autophagy-inducing agent comprising, as an active ingredient, a benzothiophene compound represented by the following general formula (1):

[Chem. 1]

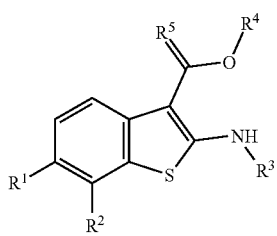

(1)

[in the formula (1), $R^1$ represents a halogen atom, an optionally substituted 5- to 10-membered aromatic carbon ring, an optionally substituted 5- to 10-membered aromatic heterocycle, or a group represented by —$R^6$—$R^7$, $R^2$ represents a halogen atom, a hydroxyl group, or a group represented by —O—$R^6$—$R^7$ or —O—$R^6$—$R^8$, $R^3$ represents a hydrogen atom or a group represented by —C(=O)$R^9$, $R^4$ represents a linear, branched, or cyclic alkyl group having 1 to 6 carbon atoms, and $R^5$ represents an oxygen atom or an imino group, and also in the formula (1), $R^6$s, which may be the same or different, each independently represent a linear, branched, or cyclic alkylene group having 1 to 6 carbon atoms, $R^7$s, which may be the same or different, each independently represent an amino group optionally substituted by a linear, branched, or cyclic alkyl group having 1 to 6 carbon atoms, a linear, branched, or cyclic alkenyl group having 2 to carbon atoms, or a linear, branched, or cyclic hydroxyalkyl group having 1 to 6 carbon atoms, $R^8$ represents an optionally substituted 5- to 10-membered aromatic carbon ring or an optionally substituted 5- to 10-membered aromatic heterocycle, and $R^9$ represents a linear, branched, or cyclic alkyl group having 1 to 6 carbon atoms, an optionally substituted 5- to 10-membered aromatic carbon ring, or an optionally substituted 5- to 10-membered aromatic heterocycle].

<2> A method for inducing alternative autophagy, comprising a step of introducing a benzothiophene compound represented by the following general formula (1) into a cell:

[Chem. 2]

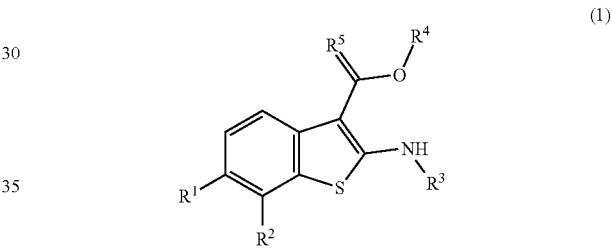

(1)

[in the formula (1), $R^1$ represents a halogen atom, an optionally substituted 5- to 10-membered aromatic carbon ring, an optionally substituted 5- to 10-membered aromatic heterocycle, or a group represented by —$R^6$—$R^7$, $R^2$ represents a halogen atom, a hydroxyl group, or a group represented by —O—$R^6$—$R^7$ or —O—$R^6$—$R^8$, $R^3$ represents a hydrogen atom or a group represented by —C(=O)$R^9$, $R^4$ represents a linear, branched, or cyclic alkyl group having 1 to 6 carbon atoms, and $R^5$ represents an oxygen atom or an imino group, and also in the formula (1), $R^6$s, which may be the same or different, each independently represent a linear, branched, or cyclic alkylene group having 1 to 6 carbon atoms, $R^7$s, which may be the same or different, each independently represent an amino group optionally substituted by a linear, branched, or cyclic alkyl group having 1 to 6 carbon atoms, a linear, branched, or cyclic alkenyl group having 2 to 6 carbon atoms, or a linear, branched, or cyclic hydroxyalkyl group having 1 to 6 carbon atoms, $R^8$ represents an optionally substituted 5- to 10-membered aromatic carbon ring or an optionally substituted 5- to 10-membered aromatic heterocycle, and $R^9$ represents a linear, branched, or cyclic alkyl group having 1 to 6 carbon atoms, an optionally substituted 5- to 10-membered aromatic carbon ring, or an optionally substituted 5- to 10-membered aromatic heterocycle].

<3> at least one benzothiophene compound selected from the group consisting of the following (a) and (b):
(a) benzothiophene compounds represented by the following general formula (1):

[Chem. 3]

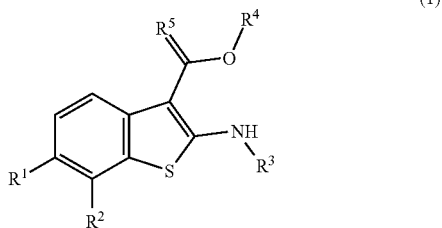

(1)

[in the formula (1), $R^1$ represents an optionally substituted 5- to 10-membered aromatic carbon ring or an optionally substituted 5- to 10-membered aromatic heterocycle, $R^2$ represents a halogen atom, a hydroxyl group, or a group represented by —O—$R^6$—$R^7$ or —O—$R^6$—$R^8$, $R^3$ represents a hydrogen atom or a group represented by —C(=O) $R^9$, $R^4$ represents a linear, branched, or cyclic alkyl group having 1 to 6 carbon atoms, and $R^5$ represents an oxygen atom or an imino group, and also in the formula (1), $R^6$ represents a linear, branched, or cyclic alkylene group having 1 to 6 carbon atoms, $R^7$ represents an amino group optionally substituted by a linear, branched, or cyclic alkyl group having 1 to 6 carbon atoms, a linear, branched, or cyclic alkenyl group having 2 to 6 carbon atoms, or a linear, branched, or cyclic hydroxyalkyl group having 1 to 6 carbon atoms, $R^8$ represents an optionally substituted 5- to 10-membered aromatic carbon ring or an optionally substituted 5- to 10-membered aromatic heterocycle, and $R^9$ represents a linear, branched, or cyclic alkyl group having 1 to 6 carbon atoms, an optionally substituted 5- to 10-membered aromatic carbon ring, or an optionally substituted 5- to 10-membered aromatic heterocycle]; and (b) benzothiophene compounds represented by the above-described general formula (1):
[in the formula (1), $R^1$ represents a halogen atom, $R^2$ represents a halogen atom, a hydroxyl group, or a group represented by —O—$R^6$—$R^7$, $R^3$ represents a group represented by a hydrogen atom, $R^4$ represents a linear, branched, or cyclic alkyl group having 1 to 6 carbon atoms, and $R^5$ represents an oxygen atom or an imino group, and also in the formula (1), $R^6$ represents a linear, branched, or cyclic alkylene group having 1 to 6 carbon atoms, and $R^7$ represents an amino group optionally substituted by a linear, branched, or cyclic alkyl group having 1 to 6 carbon atoms, a linear, branched, or cyclic alkenyl group having 2 to 6 carbon atoms, or a linear, branched, or cyclic hydroxyalkyl group having 1 to 6 carbon atoms].

<4> An anticancer agent comprising the benzothiophene compound according to <3> as an active ingredient.

<5> A method for treating cancer, comprising a step of administering the benzothiophene compound according to <3> to a patient.

<6> A method for screening for a compound having anticancer activity, comprising the following step (a):
(a) a step of bringing test compounds into contact with cells expressing a lysosomal protein to which a fluorescent protein is attached, and selecting a compound having activity to induce alternative autophagy by using, as an index, formation of fluorescent bright spots due to aggregation of the lysosomal protein.

<7> The method according to <6>, further comprising the following step (b):
(b) a step of bringing test compounds into contact with cells, and selecting a compound having activity to induce cell death by using, as an index, a survival rate of the cells after the contact.

<8> The method according to <7>, wherein
in the step (b), the cells are primary cultured cells and immortalized cells, and criteria based on the index are that a survival rate of the primary cultured cells is 80% or higher, and a survival rate of the immortalized cells is 30% or lower.

<9> The method according to <7>, wherein
in the step (b), the cells are apoptosis resistant cells, and a criterion based on the index is that the survival rate is 20% or lower.

<10> The method according to anyone of <7> to <9>, further comprising the following step (c):
(c) introducing the compound which is selected as the compound having activity to induce alternative autophagy in the step (a) and is selected as the compound having activity to induce cell death in the step (b) into a cancer-bearing non-human animal,
measuring a size of the cancer borne by the cancer-bearing non-human animal, and
selecting the test compound as a compound having anticancer activity, when an obtained measured value is smaller than a measured value of a size of the cancer borne by a cancer-bearing non-human animal into which the test compound is not introduced.

Advantageous Effects of Invention

According to the present invention, it is possible to provide a benzothiophene compound useful as an alternative autophagy-inducing agent and an anticancer agent, as well as a method for treating cancer. In addition, the method for screening for a compound having anticancer activity of the present invention makes it possible to conduct efficient screening for a compound having anticancer activity, especially, a compound having anticancer activity which effectively acts on cancer cells acquiring apoptosis resistance, by using activity to induce alternative autophagy as an index.

DESCRIPTION OF EMBODIMENTS

Figure 1:
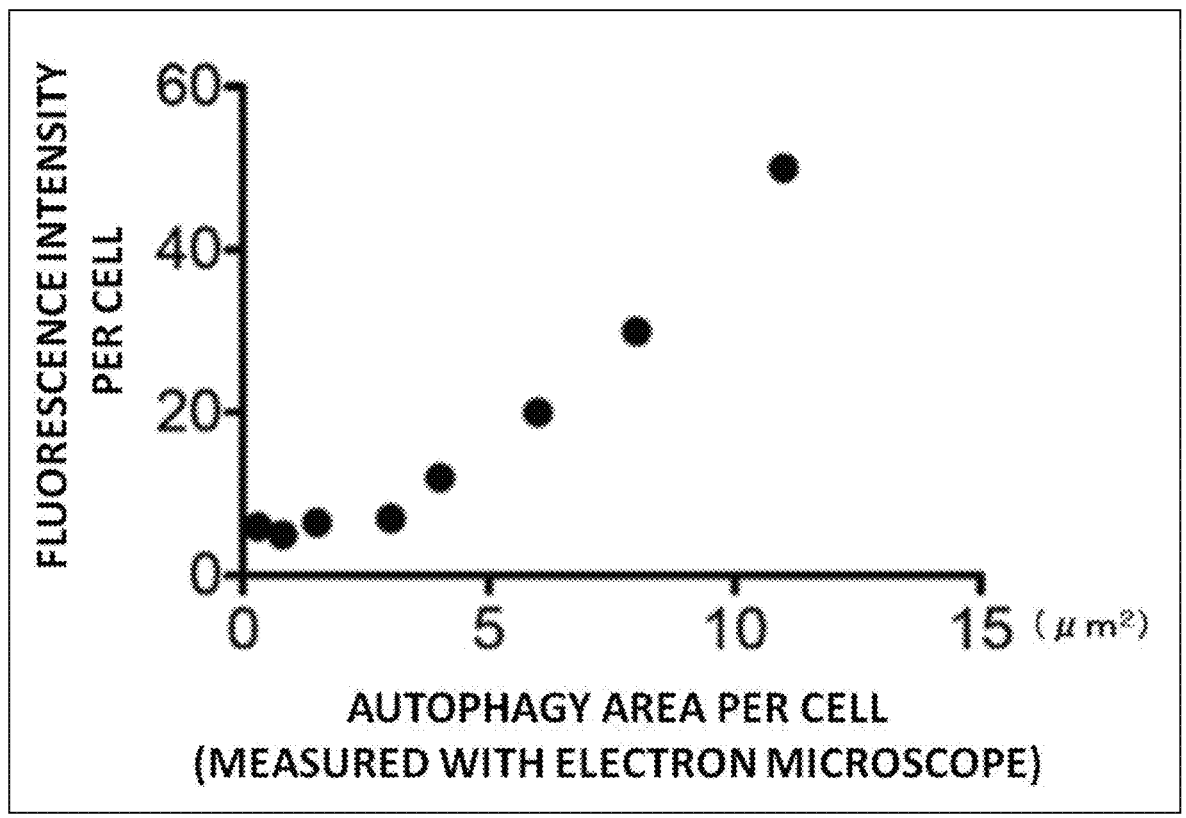
FIG. 1 is a plot showing a correlation between the area of autophagy per cell obtained by measurement using an electron microscope and the fluorescence intensity of fluorescent bright spots due to the aggregation of Lamp1-GFP in Lamp1-GFP expressing cells.

An autophagy-inducing agent of the present invention is an alternative autophagy-inducing agent comprising, as an active ingredient, a benzothiophene compound represented by the following general formula (1):

[Chem. 4]

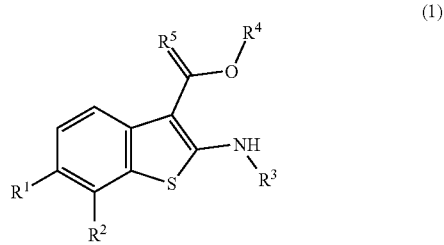

[in the formula (1), $R^1$ represents a halogen atom, an optionally substituted 5- to 10-membered aromatic carbon ring, an optionally substituted 5- to 10-membered aromatic heterocycle, or a group represented by —$R^6$—$R^7$, $R^2$ represents a halogen atom, a hydroxyl group, or a group represented by —O—$R^6$—$R^7$ or —O—$R^6$—$R^8$, $R^3$ represents a hydrogen atom or a group represented by —C(=O)$R^9$, $R^4$ represents a linear, branched, or cyclic alkyl group having 1 to 6 carbon atoms, and $R^5$ represents an oxygen atom or an imino group, and also in the formula (1), $R^6$s, which may be the same or different, each independently represent a linear, branched, or cyclic alkylene group having 1 to 6 carbon atoms, $R^7$s, which may be the same or different, each independently represent an amino group optionally substituted by a linear, branched, or cyclic alkyl group having 1 to 6 carbon atoms, a linear, branched, or cyclic alkenyl group having 2 to 6 carbon atoms, or a linear, branched, or cyclic hydroxyalkyl group having 1 to 6 carbon atoms, $R^8$ represents an optionally substituted 5- to 10-membered aromatic carbon ring or an optionally substituted 5- to 10-membered aromatic heterocycle, and $R^9$ represents a linear, branched, or cyclic alkyl group having 1 to 6 carbon atoms, an optionally substituted 5- to 10-membered aromatic carbon ring, or an optionally substituted 5- to 10-membered aromatic heterocycle].

The "halogen atom" in the general formula (1) means a fluorine atom, a chlorine atom, a bromine atom, or an iodine atom. The "halogen atom" as $R^1$ is preferably a bromine atom.

The "5- to 10-membered aromatic carbon ring" may be monocyclic or polycyclic, and examples thereof include benzene, naphthalene, and indene.

The "5- to 10-membered aromatic heterocycle" contains at least one hetero atom selected from sulfur atoms, nitrogen atoms, and oxygen atoms, and may be monocyclic or polycyclic. The number of substituent hetero atoms is preferably 1 to 3, and more preferably 1. Examples of such a 5- to 10-membered aromatic heterocycle include thiophene, benzothiophene, benzofuran, benzimidazole, benzoxazole, benzothiazole, benzisothiazole, furan, pyrrole, imidazole, pyrazole, pyridine, pyrazine, pyrimidine, pyridazine, indole, isoindole, indazole, quinolizine, isoquinoline, quinoline, phthalazine, naphthyridine, quinoxaline, quinazoline, cinnoline, thiazole, isothiazole, isoxazole, and furazan.

In addition, in the general formula (1), each of the "5- to 10-membered aromatic carbon ring" and the "5- to 10-membered aromatic heterocycle" may have one or multiple substituents in any combination at any substitutable positions. The substituents are not particularly limited, and examples thereof include halogen atoms, amino groups, imino groups, alkyl groups, cycloalkyl groups, halogenated alkyl groups, alkenyl groups, alkoxy groups, alkylthio groups, alkylamino groups, aryl groups, arylamino groups, hydroxy groups, siloxy groups, nitro groups, cyano groups, azido groups, and azidoalkyl groups.

In the general formula (1), $R^6$ represents a linear, branched, or cyclic alkylene group having 1 to 6 carbon atoms. Examples of the alkylene group include a methylene group, an ethylene group, a trimethylene group, a tetramethylene group, a pentamethylene group, a hexamethylene group, an ethylethylene group, a dimethylethylene group, a butylethylene group, a cyclohexylene group, and a cyclopentylene group.

In the general formula (1), $R^7$ represents an amino group optionally substituted by a linear, branched, or cyclic alkyl group having 1 to 6 carbon atoms, an amino group optionally substituted by a linear, branched, or cyclic alkenyl group having 2 to 6 carbon atoms, or an amino group optionally substituted by a linear, branched, or cyclic hydroxyalkyl group having 1 to 6 carbon atoms. The expression "amino group optionally substituted by a group" means that the amino group may have one or multiple substituents in any combination at any substitutable positions.

Examples of the "linear, branched, or cyclic alkyl group having 1 to 6 carbon atoms" include a methyl group, an ethyl group, a n-propyl group, an i-propyl group, a n-butyl group, an i-butyl group, a sec-butyl group, a tert-butyl group, a pentyl group, an isopentyl group, a neopentyl group, a hexyl group, a cyclopropyl group, a cyclobutyl group, a cyclopentyl group, and a cyclohexyl group.

Examples of the "linear, branched, or cyclic alkenyl group having 2 to 6 carbon atoms" include a vinyl group, a 1-propenyl group, a 2-propenyl group, an isopropenyl group, a 2-butenyl group, a 1,3-butadienyl group, a 2-pentenyl group, a 2-hexenyl group, a cyclopropenyl group, a cyclopentenyl group, and a cyclohexenyl group.

Examples of the "linear, branched, or cyclic hydroxyalkyl group having 1 to 6 carbon atoms" include a hydroxyethyl group, a 2-hydroxypropyl group, a 3-hydroxypropyl group, a 4-hydroxybutyl group, a 2-hydroxybutyl group, a 2-(hydroxymethyl)propyl group, a 2-hydroxypentyl group, a 3-hydroxypentyl group, a 5-hydroxypentyl group, a 2-hydroxyhexyl group, and a 6-hydroxyhexyl group.

$R^1$ according to the autophagy-inducing agent of the present invention represents a halogen atom, an optionally substituted 5- to 10-membered aromatic carbon ring, an optionally substituted 5- to 10-membered aromatic heterocycle, or a group represented by —$R^6$—$R^7$. The "halogen atom" is as described above, and is preferably a bromine atom. Each "substituent" for the optional substitution is as described above, and is preferably a halogen atom, an alkyl group, a nitro group, an alkoxy group, an alkylthio group, a hydroxyl group, an alkyl amino group, a halogenated alkyl group, an azido group, or an azidoalkyl group, and more preferably a fluorine atom, a nitro group, a methyl group, a methylthio group, a hydroxyl group, a dimethylamino group, a trifluoromethyl group, an azido group, or an azidomethyl group. From the viewpoint that the ability to induce alternative autophagy is higher, the "substituent" is further preferably an alkylthio group (particularly, a methylthio group), an alkoxy group (particularly, a methoxy group), or a hydroxyl group. Moreover, the "5- to 10-membered aromatic carbon ring" is as described above, and is preferably benzene. Meanwhile, the "5- to 10-membered aromatic heterocycle" is preferably thiophene or pyridine. Thiophene (particularly, 3-thiophene or 2-thiophene) is more preferable, from the viewpoint that the ability to induce alternative autophagy is higher.

Moreover, the "optionally substituted 5- to 10-membered aromatic carbon ring" or the "optionally substituted 5- to 10-membered aromatic heterocycle" as $R^1$ according to the autophagy-inducing agent of the present invention is further preferably any of the substituents represented by the following formulae. In the following formulae, "Me" represents a methyl group ($CH_3$ group) (hereinafter the same shall apply).

[Chem. 5]

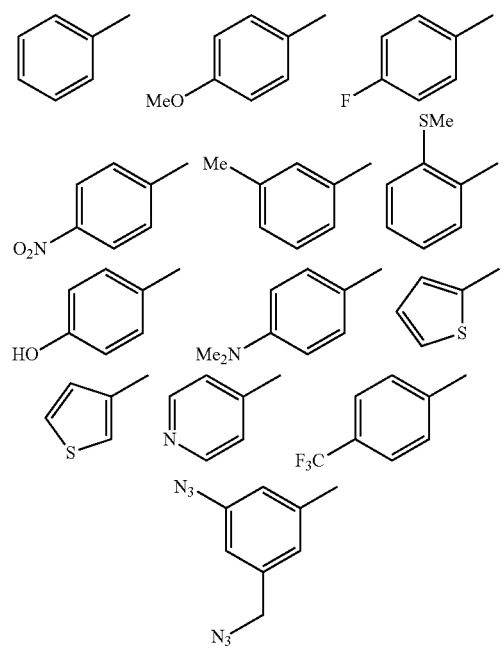

Of these substituents, particularly preferred are those represented by the following formulae.

[Chem. 6]

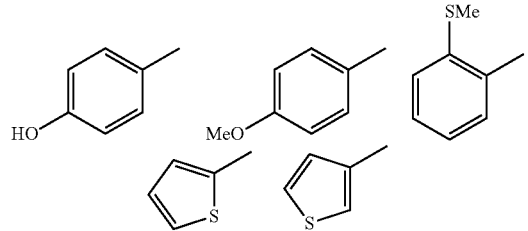

$R^6$ in $R^1$ according to the autophagy-inducing agent of the present invention is as described above, and is preferably a methylene group. Meanwhile, $R^7$ in $R^1$ is as described above, and is preferably a diethyl-substituted amide group, a 2-propenyl-substituted amide group, a hydroxyethyl-substituted amide group, or a 4-hydroxybutyl-substituted amide group.

Moreover, the "group represented by —$R^6$—$R^7$" as $R^1$ according to the autophagy-inducing agent of the present invention is more preferably any of the substituents represented by the following formulae.

[Chem. 7]

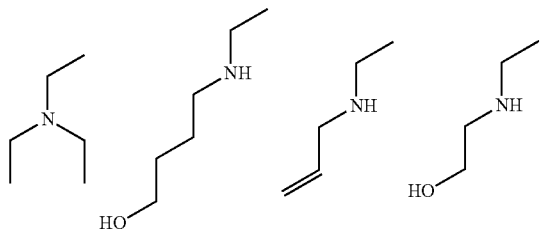

$R^2$ according to the autophagy-inducing agent of the present invention represents a halogen atom, a hydroxyl group, or a group represented by —O—$R^6$—$R^7$ or —O—$R^6$—$R^8$. The "halogen atom" is as described above, and is preferably a chlorine atom. In addition, $R^6$ is as described above, and is preferably a methylene group or an ethylene group. Further, $R^7$ is as described above, and is preferably a diethyl-substituted amide group. In $R^1$ and $R^2$ according to the autophagy-inducing agent of the present invention, each of the pairs of $R^6$ s and $R^7$s may be the same or different, and $R^6$s and $R^7$s each independently represent any of the above-described groups.

$R^8$ represents an optionally substituted 5- to 10-membered aromatic carbon ring or an optionally substituted 5- to 10-membered aromatic heterocycle. The "optionally substituted 5- to 10-membered aromatic carbon ring" and the "optionally substituted 5- to 10-membered aromatic heterocycle" are as described above, and benzene is preferable.

In addition, the "group represented by —O—$R^6$—$R^7$ or —O—$R^6$—$R^8$", as $R^2$ according to the autophagy-inducing agent of the present invention is more preferably any of the substituents represented by the following formulae.

[Chem. 8]

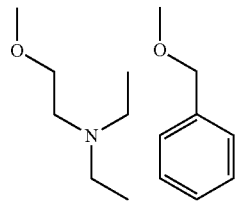

$R^3$ according to the autophagy-inducing agent of the present invention represents a hydrogen atom or a group represented by —C(=O)$R^9$. $R^9$ represents a linear, branched, or cyclic alkyl group having 1 to 6 carbon atoms, an optionally substituted 5- to 10-membered aromatic carbon ring, or an optionally substituted 5- to 10-membered aromatic heterocycle. In $R^9$, the "linear, branched, or cyclic alkyl group having 1 to 6 carbon atoms", the "optionally substituted 5- to 10-membered aromatic carbon ring", and the "optionally substituted 5- to 10-membered aromatic heterocycle" are as described above. Here, the "linear, branched, or cyclic alkyl group having 1 to 6 carbon atoms" is preferably a methyl group, and the "optionally substituted 5- to 10-membered aromatic carbon ring" is preferably benzene.

$R^4$ in the general formula (1) represents a linear, branched, or cyclic alkyl group having 1 to 6 carbon atoms. In $R^4$, the "linear, branched, or cyclic alkyl group having 1 to 6 carbon atoms" is as described above, and the "linear, branched, or cyclic alkyl group having 1 to 6 carbon atoms" is preferably a methyl group or an ethyl group.

In the general formula (1), $R^5$ represents an oxygen atom or an imino group (NH group).

In addition, the benzothiophene compound which is the active ingredient of the autophagy-inducing agent of the present invention is more preferably any of the benzothiophene compounds represented by the following formulae (1-1) to (1-33).

[Chem. 9]

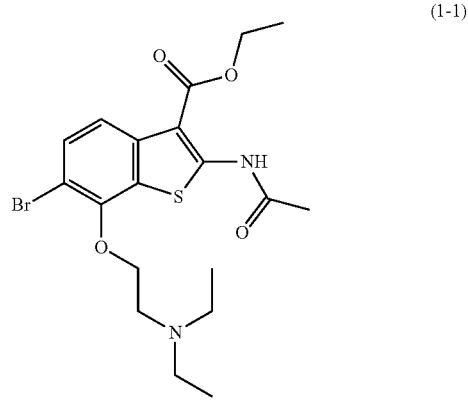
(1-1)

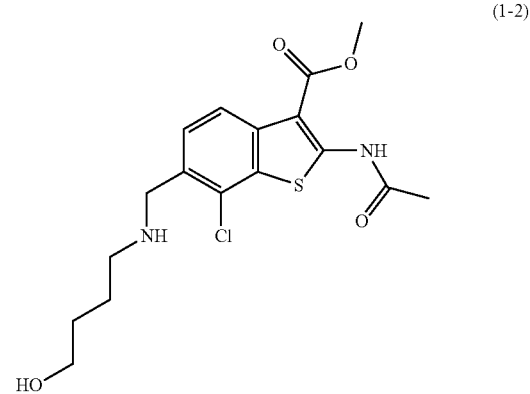
(1-2)

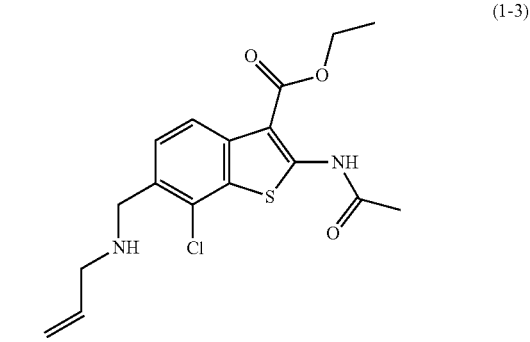
(1-3)

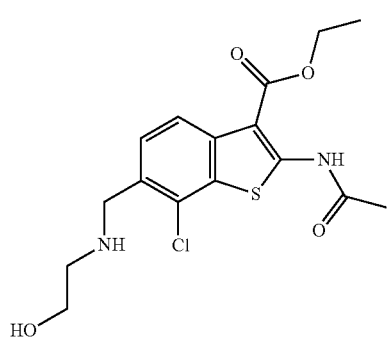
(1-4)
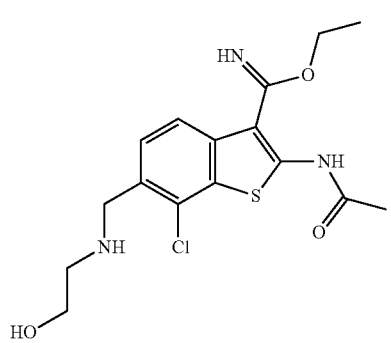
(1-5)
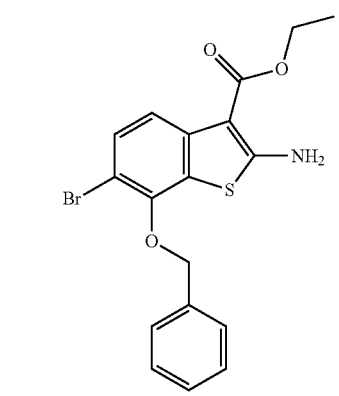
(1-6)
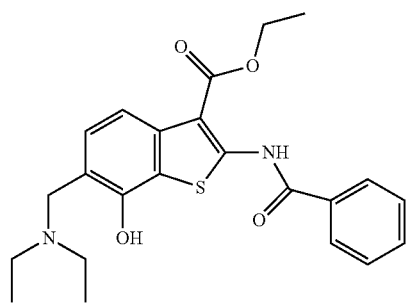
(1-7)
[Chem. 10]
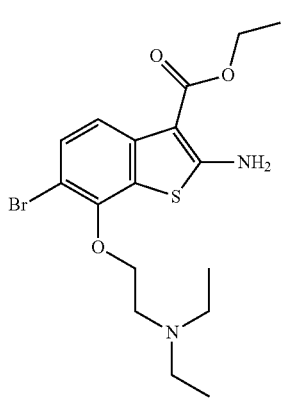
(1-8)
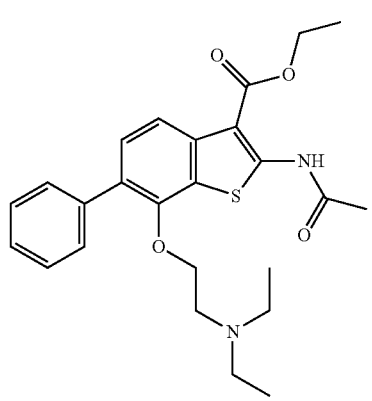
(1-9)
[Chem. 11]
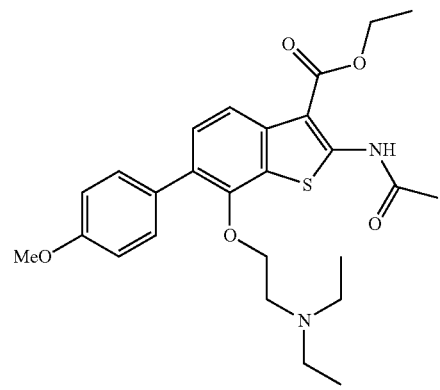
(1-10)
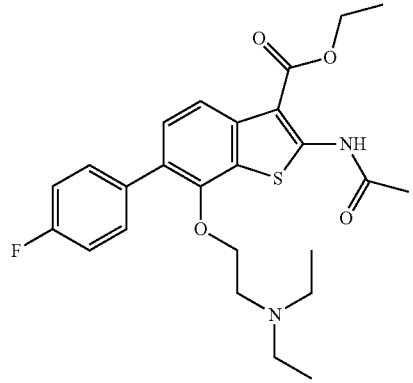
(1-11)

-continued
(1-12)
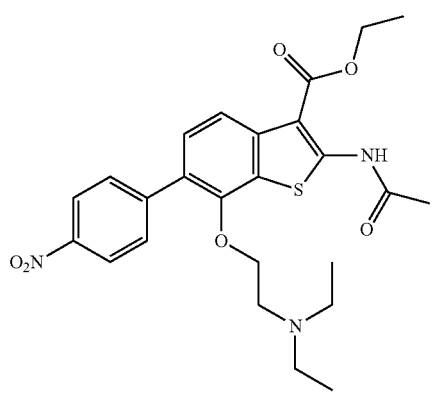
(1-16)
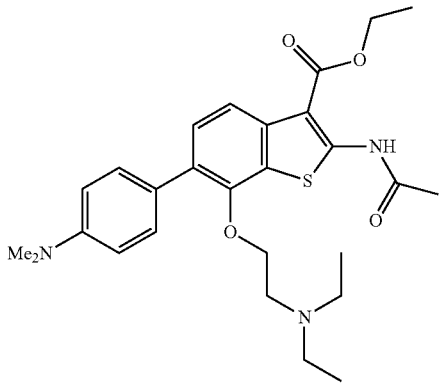
(1-13)
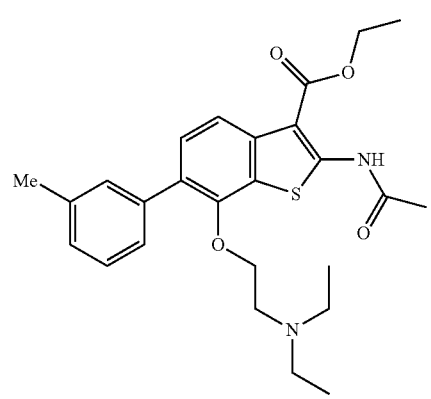
(1-17)
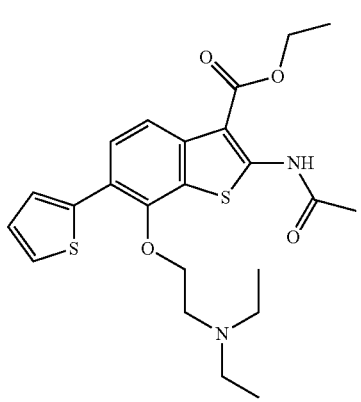
(1-14)
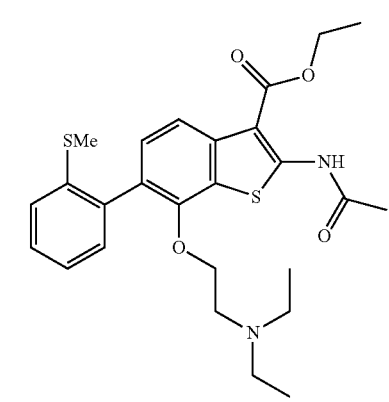
(1-18)
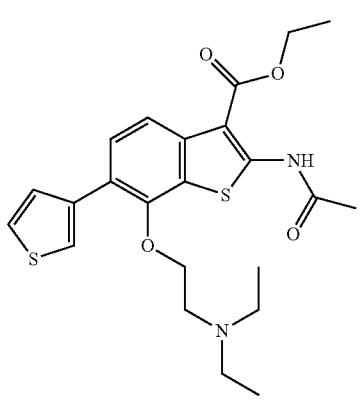
(1-15)
(1-19)
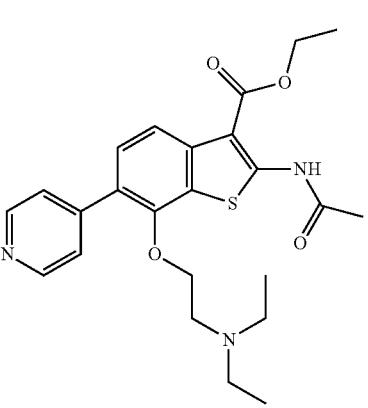

-continued (1-20), (1-21), (1-22), (1-23), (1-24), (1-25), (1-26), (1-27)

[Chem. 12]

(1-28)
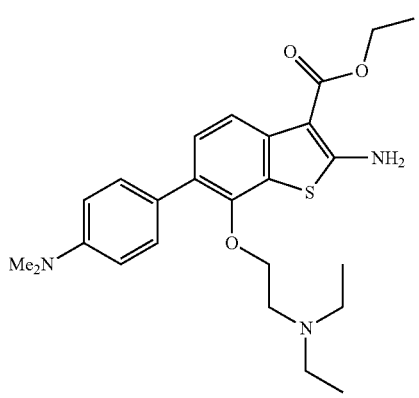

(1-29)
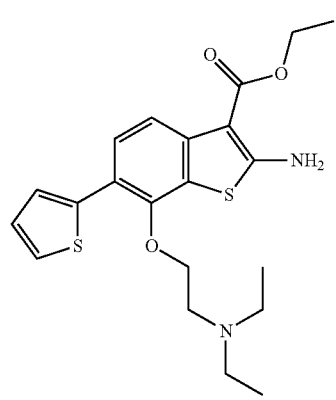

(1-30)
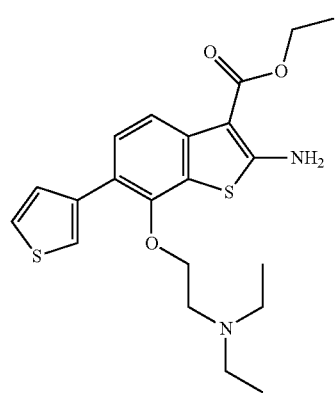

(1-31)
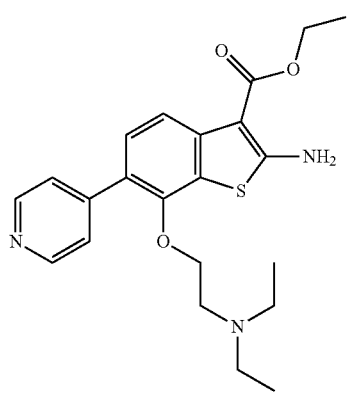

(1-32)
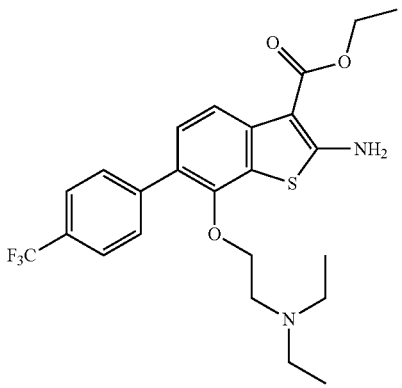

(1-33)
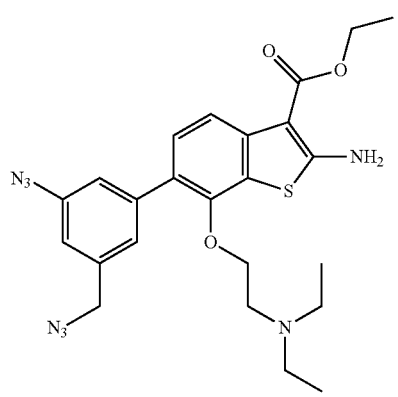

In addition, from the viewpoint that the ability to induce alternative autophagy is higher, as shown in Examples described later, the benzothiophene compound which is the active ingredient of the autophagy-inducing agent of the present invention is further preferably the benzothiophene compound represented by the above-described formula (1-10), (1-14), (1-15), (1-17), or (1-18), and particularly preferably the benzothiophene compound represented by the above-described formula (1-15).

In addition, the benzothiophene compound of the present invention also includes pharmacologically acceptable salts and solvates. The pharmacologically acceptable salts are not particularly limited, and a salt can be selected, as appropriate, according to purpose. Examples of the salts include hydrochloric acid salts, sulfuric acid salts, hydrogen bromide salts, nitric acid salts, hydrogen sulfate salts, phosphoric acid salts, acetic acid salts, lactic acid salts, succinic acid salts, citric acid salts, maleic acid salts, hydroxymaleic acid salts, tartaric acid salts, fumaric acid salts, methane sulfonic acid salts, p-toluenesulfonic acid salts, camphorsulfonic acid salts, sulfamic acid salts, mandelic acid salts, propionic acid salts, glycolic acid salts, stearic acid salts, malic acid salts, ascorbic acid salts, pamoic acid salts, phenylacetic acid salts, glutamic acid salts, benzoic acid salts, salicylic acid salts, sulfanilic acid salts, 2-acetoxybenzoic acid salts, ethanedisulfonic acid salts, oxalic acid salts, isethionic acid salts, formic acid salts, trifluoroacetic acid salts, ethylsuccinic acid salts, lactobionic acid salts, gluconic acid salts, glucoheptonic acid salts, 2-hydroxyethanesulfonic acid salts, benzenesulfonic acid salts, lauryl sulfate salts, aspartic acid salts, adipic acid salts, hydroiodic acid salts, nicotinic acid salts, oxalic acid salts, picric acid salts, thiocyanic acid salts, and undecanoic acid salts. In addition, the solvates are not particularly limited, and a solvate can be selected, as appropriate, according to purpose. The solvates also include hydrates.

Moreover, the benzothiophene compound of the present invention includes all isomers such as geometrical isomers, optical isomers based on asymmetric carbon, stereoisomers, and tautomers, as well as isomer mixtures. In addition, the benzothiophene compound of the present invention also includes compounds which are derived from the benzothiophene compound of the present invention by metabolism such as oxidation, reduction, hydrolysis, or conjugation in a living organism but which still exhibit a desired activity. The present invention further includes compounds which produce the benzothiophene compound of the present invention by being subjected to metabolism such as oxidation, reduction, or hydrolysis in a living organism. In addition, as described later, pharmaceutical preparations of the autophagy-inducing agent of the present invention can be prepared by known pharmaceutical methods.

A method for obtaining the benzothiophene compound of the present invention is not particularly limited, and, for example, the benzothiophene compounds represented by the above-described formulae (1-1) to (1-8) can be purchased from Pharmeks Ltd., RUSSIA.

In addition, a method for synthesizing the benzothiophene compound of the present invention is not particularly limited, and, for example, the benzothiophene compound can be produced by the following methods. In the following formulae (2) and (3) and the benzothiophene compounds represented by (1a) to (1d), $R^4$ to $R^9$ are as described above.

First, according to a description in "Grinev. A. N. et al., "Synthesis of 2-(acylamino)-7-hydroxybenzo[b]thiophene derivatives, bromination and nitration" Khimiya Geterotsiklicheskikh Soedinenii, 1987, vol. 4, pp. 460 to 462," a benzothiophene compound represented by the following formula (2) is reacted with bromine in a solvent (for example, chloroform) to synthesize a benzothiophene compound represented by the following formula (3).

[Chem. 13]

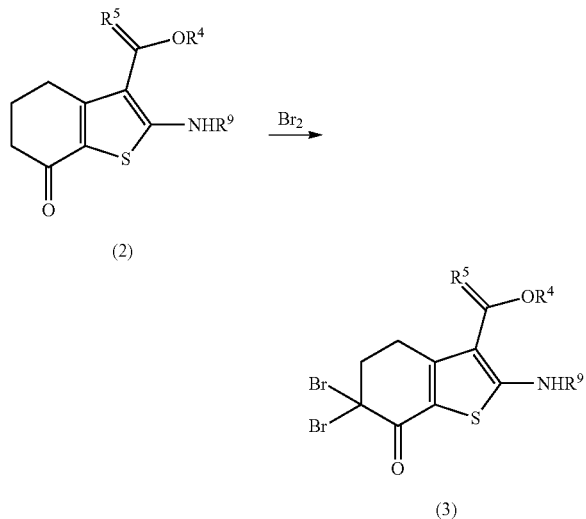

Subsequently, the benzothiophene compound represented by the following formula (3) is reacted with abase (for example, potassium carbonate) in a solvent (for example, a mixture solvent of dioxane and water). Thus, a benzothiophene compound represented by the following formula (1a) can be synthesized.

[Chem. 14]

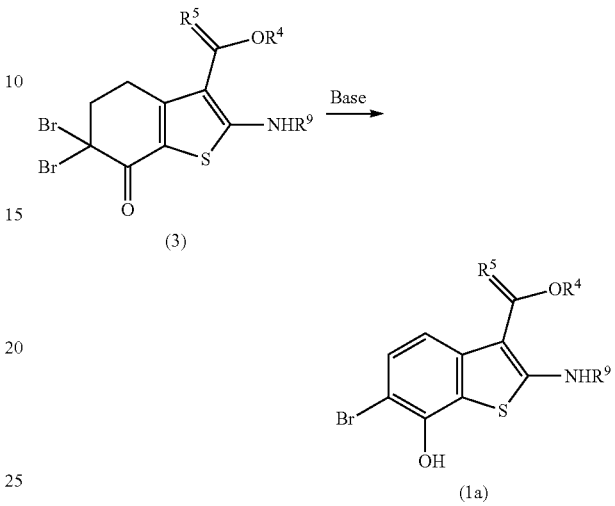

Moreover, the benzothiophene compound represented by the above-described formula (1a) is reacted with a halogenated compound (a compound represented by X—$R^6$—$R^7$ or a compound represented by X—$R^6$—$R^8$) in a solvent (for example, dimethylformamide). Thus, also a benzothiophene compound represented by the following formula (1b) can be synthesized.

[Chem. 15]

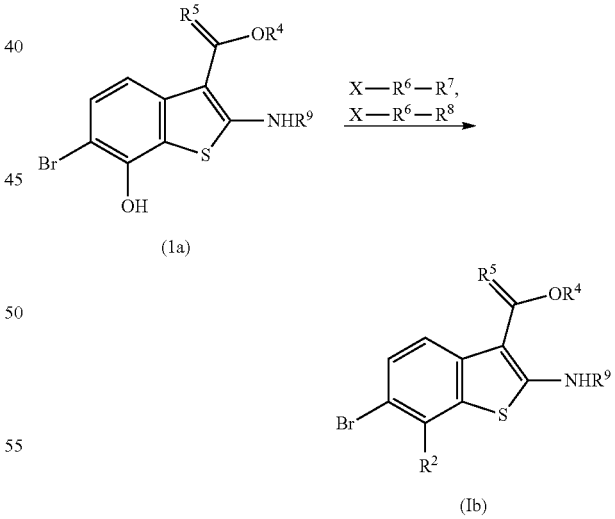

In the halogenated compound, X means a halogen atom (a fluorine atom, a chlorine atom, a bromine atom, or an iodine atom). In addition, in the benzothiophene compounds represented by the formula (1b) shown above and the formulae (1c) to (1e) shown below, $R^2$ represents a "group represented by —O—$R^6$—$R^7$ or —O—$R^6$—$R^8$".

Moreover, the benzothiophene compound represented by the above-described formula (1b) and a boronic acid reagent (a compound represented by $R^1$—B(OH)$_2$) are reacted with each other in the presence of a base (for example, potassium phosphate) and a palladium catalyst (for example, dichlorobis[di-t-butyl(p-dimethylaminophenyl)phosphino]palladium(II)) in a solvent (for example, a mixture solvent of acetonitrile and water). Thus, also a benzothiophene compound represented by the following formula (1c) can be synthesized.

[Chem. 16]

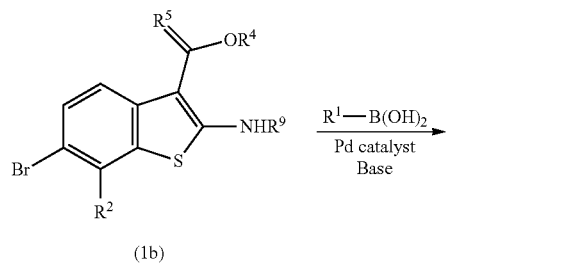

(1b)

(1c)

In the above-described boronic acid reagent, the benzothiophene compound represented by the formula (1c) shown above, and a benzothiophene compound represented by the formula (1e) shown below, $R^1$ represents "an optionally substituted 5- to 10-membered aromatic carbon ring, an optionally substituted 5- to 10-membered aromatic heterocycle, or a group represented by —$R^6$—$R^7$".

Moreover, the benzothiophene compound represented by the above-described formula (1b) is hydrolyzed with a strong base or the like (for example, sodium hydroxide or potassium hydroxide) in a solvent (for example, a mixture solvent of tetrahydrofuran (THF) and methanol, or a mixture solvent of methanol and water). Thus, the benzothiophene compound represented by the following formula (1d) can also be synthesized. Still moreover, the benzothiophene compound represented by the above-described formula (1c) is hydrolyzed in the same manner as described above. Thus, a benzothiophene compound represented by the following formula (1e) can also be synthesized.

[Chem. 17]

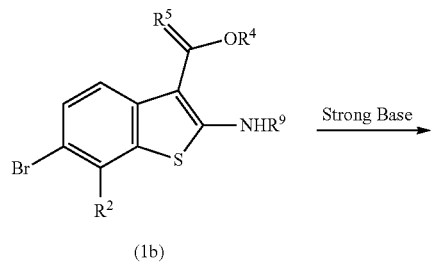

(1b)

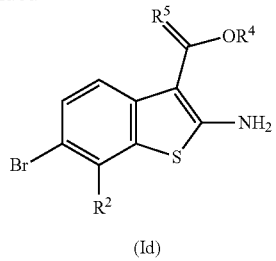

(1d)

[Chem. 18]

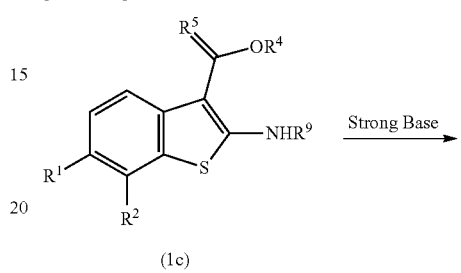

(1c)

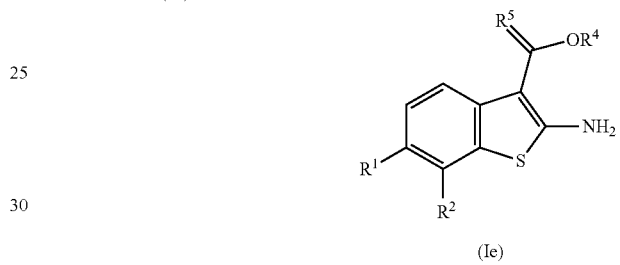

(1e)

In each of the synthesis methods, a protective group may be introduced, as appropriate, to protect a substituent in each compound. The protective group is not particularly limited, and examples thereof include a methyl group, a benzyl group, a p-methoxybenzyl group, a tert-butyl group, a tert-butyl ester group, an acetal group, a phthaloyl group, a tert-butoxycarbonyl group, and a benzyloxycarbonyl group. Moreover, when a compound in which a protective group is introduced is used, a deprotection reaction suitable for the protective group may be conducted, if necessary.

In addition, in each of the synthesis methods, the isolation and purification of the target product from the obtained reaction mixture are not particularly limited, and a known approach (concentration, crystallization, distillation, purification by suspension, chromatographic purification, or the like) selected, as appropriate, can be conducted.

As described above, preferred methods for synthesizing the benzothiophene compound of the present invention (the benzothiophene compounds represented by the above-described formulae (1a) to (1d)) are described. However, the method for synthesizing the compound of the present invention is not limited the above-described methods. In addition, specific methods for producing compounds of the present invention are shown in Examples described later. Hence, those skilled in the art can produce the benzothiophene compounds of the present invention by selecting, as appropriate, the reaction raw material, the reaction reagent, the reaction conditions (for example, the solvent, the reaction temperature, the catalyst, and the reaction time), and the like with reference to the description given above and the description in Examples, and, if necessary, modifying or altering these methods, as appropriate.

In the present invention, the "alternative autophagy" means an intracellular cleaning mechanism in which an autophagosome is formed without using any autophagy-related molecule such as Atg5 or Atg7, and further a lysosome fuses with the autophagosome to degrade an intracellular component taken up by the autophagosome. The above-described benzothiophene compound represented by the above-described general formula (1) has activity to induce alternative autophagy, as shown in Examples described later. Hence, the present invention can provide not only the alternative autophagy-inducing agent comprising the compound as an active ingredient, but also a method for inducing alternative autophagy, the method comprising a step of introducing the benzothiophene compound into a cell.

The "introduction" of the benzothiophene compound into the cell is generally conducted by adding the benzothiophene compound to a culture liquid of the cell. However, the "introduction" is not limited to this method, and can be conducted by a known approach selected, as appropriate. The concentration of the benzothiophene compound to be introduced varies depending on the properties (solubility, toxicity, and the like) of the compound. For example, the concentration at which the benzothiophene compound is added to the culture liquid of the cell is preferably selected, as appropriate, within a range from 0.1 nM to 100 µM. Moreover, for example, the time for which the benzothiophene compound is kept added to the culture liquid of the cell is preferably 10 minutes to 48 hours.

Among the above-described benzothiophene compounds represented by the above-described general formula (1), the benzothiophene compounds represented by the above-described formulae (1-8) to (1-33) were newly designed in the present invention.

Accordingly, the present invention makes it possible to provide at least one benzothiophene compound selected from the group consisting of the following (a) and (b):

(a) benzothiophene compounds represented by the above-described general formula (1):

[in the formula (1), $R^1$ represents an optionally substituted 5- to 10-membered aromatic carbon ring or an optionally substituted 5- to 10-membered aromatic heterocycle, $R^2$ represents a halogen atom, a hydroxyl group, or a group represented by —O—$R^6$—$R^7$ or —O—$R^6$—$R^8$, $R^3$ represents a hydrogen atom or a group represented by —C(=O)$R^9$, $R^4$ represents a linear, branched, or cyclic alkyl group having 1 to 6 carbon atoms, and $R^5$ represents an oxygen atom or an imino group, and also in the formula (1), $R^6$ represents a linear, branched, or cyclic alkylene group having 1 to 6 carbon atoms, $R^7$ represents an amino group optionally substituted by a linear, branched, or cyclic alkyl group having 1 to 6 carbon atoms, a linear, branched, or cyclic alkenyl group having 2 to 6 carbon atoms, or a linear, branched, or cyclic hydroxyalkyl group having 1 to 6 carbon atoms, $R^8$ represents an optionally substituted 5- to 10-membered aromatic carbon ring or an optionally substituted 5- to 10-membered aromatic heterocycle, and $R^9$ represents a linear, branched, or cyclic alkyl group having 1 to 6 carbon atoms, an optionally substituted 5- to 10-membered aromatic carbon ring, or an optionally substituted 5- to 10-membered aromatic heterocycle]; and (b) benzothiophene compounds represented by the above-described general formula (1):

[in the formula (1), $R^1$ represents a halogen atom, $R^2$ represents a halogen atom, a hydroxyl group, or a group represented by —O—$R^6$—$R^7$, $R^3$ represents a group represented by a hydrogen atom, $R^4$ represents a linear, branched, or cyclic alkyl group having 1 to 6 carbon atoms, and $R^5$ represents an oxygen atom or an imino group, and also in the formula (1), $R^6$ represents a linear, branched, or cyclic alkylene group having 1 to 6 carbon atoms, and $R^7$ represents an amino group optionally substituted by a linear, branched, or cyclic alkyl group having 1 to 6 carbon atoms, a linear, branched, or cyclic alkenyl group having 2 to carbon atoms, or a linear, branched, or cyclic hydroxyalkyl group having 1 to 6 carbon atoms].

In each of the benzothiophene compounds (a), the optionally substituted 5- to 10-membered aromatic carbon ring, the optionally substituted 5- to 10-membered aromatic heterocycle, and $R^2$ to $R^5$ are as described above. In each of the benzothiophene compounds (b), the halogen atom, the group represented by —O—$R^6$—$R^7$, $R^4$, and $R^5$ are as describe above.

The benzothiophene compounds (a) are preferably the benzothiophene compounds represented by (1-9) to (1-33) shown above, and the benzothiophene compound (b) is the benzothiophene compound represented by (1-8) shown above.

As described above, the above-described benzothiophene compounds (a) and (b) also include pharmacologically acceptable salts and solvates, and also include all isomers such as geometrical isomers, optical isomers based on asymmetric carbon, stereoisomers, and tautomers, as well as isomer mixtures. Moreover, as described above, the above-described benzothiophene compounds (a) and (b) also include compounds which are derived from the benzothiophene compounds (a) and (b) by metabolism such as oxidation, reduction, hydrolysis, or conjugation in a living organism, but which still exhibit a desired activity. The present invention further includes compounds which produce the above-described benzothiophene compounds (a) and (b) by being subjected to metabolism such as oxidation, reduction, or hydrolysis in a living organism. In addition, methods for synthesizing the above-described benzothiophene compounds (a) and (b) are not particularly limited, and the above-described benzothiophene compounds (a) and (b) can be produced by, for example, the above-described synthesis methods.

As shown in Examples described later, it has been also found that the above-described benzothiophene compound represented by the above-described general formula (1) not only has the activity to induce alternative autophagy, but also can induce cell death specific to cancer cells. Hence, the present invention can provide an anticancer agent comprising, as an active ingredient, at least one benzothiophene compound selected from the group consisting of the above-described (a) and (b).

In the present invention, the "anticancer" activity means activity to inhibit growth of cancer cells and/or activity to induce death of cancer cells. The cancer to which the anticancer agent and the method for treating cancer of the present invention are directed is not particularly limited, and examples thereof include nasopharyngeal tumors, thyroid tumors, central nervous system tumors (neuroblastoma, astrocytoma, glioblastoma multiforme, and the like), melanoma, vascular tumors, epithelial tumors, non-epithelial tumors, hematoma, leukemia, lymphoma, cervical cancer, breast cancer, pulmonary cancer, prostate cancer, colorectal cancer, hepatic cancer, urogenital cancer, osteosarcoma, chondrosarcoma, gastric cancer, and pancreatic cancer.

Pharmaceutical preparations can be prepared from the anticancer agent or the alternative autophagy-inducing agent of the present invention by known pharmaceutical methods. For example, the anticancer agent and the alternative autophagy-inducing agent of the present invention can be used orally or parenterally in the forms of capsules, tablets, pills, liquids, powders, granules, fine granules, film-coated agents, pellets, troches, sublingual preparations, chewables, buccals, pastes, syrups, suspensions, elixirs, emulsions, liniments, ointments, plasters, cataplasms, transdermal systems, lotions, inhalants, aerosols, injections, suppositories, and the like.

For preparing these pharmaceutical preparations, the anticancer agent or the alternative autophagy-inducing agent of the present invention can be used, as appropriate, in combination with any ones of pharmacologically acceptable carriers and media, other additives, and the like. Here, specific examples of the pharmacologically acceptable carriers and media include sterile water, physiological saline, vegetable oils, solvents, bases, emulsifiers, suspending agents, surfactants, stabilizers, flavoring agents, aromatics, excipients, vehicles, preservatives, binders, diluents, tonicity adjusting agents, analgesics, bulking agents, disintegrators, buffering agents, coating agents, lubricants, coloring agents, sweeteners, thickening agents, flavor modifiers, and solubilizers. Moreover, the anticancer agent and the alternative autophagy-inducing agent of the present invention may be used in combination with other known anticancer agents.

Preferred modes of administration of the anticancer agent and the alternative autophagy-inducing agent of the present invention include, but are not particularly limited to, oral administration and parenterally administration, and more specifically include intravenous administration, intraarterial administration, intraperitoneal administration, subcutaneous administration, intradermal administration, intratracheal administration, rectal administration, and intramuscular administration, as well as administration by infusion.

The anticancer agent and the alternative autophagy-inducing agent of the present invention can be used for subjects which are animals including human. The animals other than human are not particularly limited, and the subjects other than human include various domestic animals, poultry, pet animals, experimental animals, and the like.

When the anticancer agent or the alternative autophagy-inducing agent of the present invention is administered, the administered amount is selected, as appropriate, according to the age, body weight, symptoms, health conditions, and the like of the subject. For example, the amount of the anticancer agent or the alternative autophagy-inducing agent of the present invention administered per administration is preferably such that the amount of the at least one benzothiophene compound selected from the group consisting of the above-described (a) and (b), which is the active ingredient, is 0.01 mg/kg body weight to 0.2 g/kg body weight.

As described above, the present invention makes it possible to treat cancer by administering the anticancer agent or the like of the present invention to a subject. Hence, the present invention also provides a method for treating cancer comprising administering at least one benzothiophene compound selected from the group consisting of the above-described (a) and (b).

A product of the anticancer agent or the like of the present invention and a manual thereof may be provided with an indication stating that the product is used for treating cancer. Here, "a product or a manual provided with an indication" means that an indication is provided to a main body, a container, a package, or the like of the product, or an indication is provided to a manual, a package insert, an advertisement, other printed matters, or the like in which information of the product is disclosed. In addition, the indication stating that the product is used for treating cancer can include the fact that the administration of the benzothiophene compound of the present invention can induce alternative autophagy, and induce cell death specific to cancer cells, as information about the mechanism of action of the anticancer agent of the present invention.

The benzothiophene compound, the alternative autophagy-inducing agent, the anticancer agent, the method for inducing alternative autophagy, and the method for treating cancer of the present invention are described above. Next, a method for screening for a compound having anticancer activity of the present invention is described step by step.

<Step of Selecting Compound Having Anticancer Activity by Using Activity to Induce Alternative Autophagy as Index>

A method for screening for a compound having anticancer activity of the present invention is a method comprising:

(a) a step of bringing test compounds into contact with cells expressing a lysosomal protein to which a fluorescent protein is attached, and selecting a compound having activity to induce alternative autophagy by using, as an index, formation of fluorescent bright spots due to aggregation of the lysosomal protein.

In the present invention, the "alternative autophagy" means an intracellular cleaning mechanism in which an autophagosome is formed without using any autophagy-related molecule such as Atg5 or Atg7, and further a lysosome fuses with the autophagosome to degrade an intracellular component taken up by the autophagosome.

In the present invention, the "anticancer activity" means activity to inhibit growth of cancer cells and/or activity to induce death of cancer cells. Examples of target cancer cells include cancer cells of nasopharyngeal tumors, thyroid tumors, central nervous system tumors (neuroblastoma, astrocytoma, glioblastoma multiforme, and the like), melanoma, vascular tumors, epithelial tumors, non-epithelial tumors, hematoma, leukemia, lymphoma, cervical cancer, breast cancer, pulmonary cancer, prostate cancer, colorectal cancer, hepatic cancer, urogenital cancer, osteosarcoma, chondrosarcoma, gastric cancer, and pancreatic cancer.

The "lysosomal protein" according to the present invention only needs to be a protein expressed specifically in the lysosome, and examples thereof include Lamp1, Lamp2, Limp1, Limp2, and AEP.

In the present invention, the "fluorescent protein" attached to the lysosomal protein only needs to be a protein capable of emitting fluorescent light upon irradiation with excitation light, and examples thereof include GFP and mCherry.

The fluorescent protein may be attached to either the N-terminus or the C-terminus of the lysosomal protein, unless a function of the lysosomal protein is suppressed. The fluorescent protein may be attached directly to the lysosomal protein, or may be attached indirectly with a spacer provided therebetween.

In addition to the fluorescent protein, another functional protein may be attached to the lysosomal protein. The other functional protein is not particularly limited, and examples thereof include a Myc-tag, a His-tag, a hemagglutin (HA)-tag, a FLAG-tag, and a glutathione S-transferase (GST).

In the present invention, the "cells" in which the lysosomal protein is expressed are not particularly limited, and are preferably cells in which a function of at least one protein selected from the group consisting of Atg5, Atg7, Atg9, Atg12, and Atg16 is suppressed, from the viewpoint that the aggregation of the lysosomal protein which depends on the induction of alternative autophagy can be easily detected.

Those skilled in the art can prepare the cells in which a function of Atg5 or the like is suppressed by selecting a known approach, as appropriate. Examples of the known approach include a method in which a pluripotent stem cell such as an ES cell is made deficient in the gene of the above-described Atg5 or the like by homologous recombination, and a method a mutation is introduced into the gene. Desired cells in which a function of Atg5 or the like is suppressed can be isolated from a non-human animal produced by implanting such a pluripotent stem cell in a blastocyst. In addition, desired differentiated cells in which a function of Atg5 or the like is suppressed can be prepared by culturing such a pluripotent stem cell in the presence of cytokines and the like.

In the present invention, as a method for suppressing a function of Atg5 or the like in cells other than the method using homologous recombination, for example, a method may be employed in which an siRNA, shRNA, or antisense nucleic acid having a sequence complementary to the gene for the Atg5 or the like is introduced into the cells.

Those skilled in the art can prepare the cells expressing a lysosomal protein to which a fluorescent protein is attached by selecting a known approach, as appropriate. The known approach is, for example, a method in which a vector containing DNA coding for a lysosomal protein to which a fluorescent protein is attached in an expressible manner is introduced into a cell. Examples of the "vector" used include plasmid DNA, adenovirus vectors, adeno-associated virus vectors, retrovirus vectors, lentivirus vectors, herpes virus vectors, and Sendai virus vectors into which DNA coding for a lysosomal protein in which a fluorescent protein is attached is inserted. For efficient expression of the DNA, the vector preferably has a promoter, an enhancer, a terminator, a poly A signal, a selectable marker such as a drug resistant gene, and the like.

To introduce the vector into the cell, for example, a known method such as a calcium phosphate method, a DEAE dextran method, a lipofection method, an electroporation method, or a microinjection method can be used, when a plasmid DNA is used as the vector. Meanwhile, when a virus vector is used as the vector, for example, a method can be employed in which a viral vector is introduced into packaging cells by a calcium phosphate method or the like, virus particles are produced by the cells, and collected virus particles are brought into contact with the cell.

The "expression" of the lysosomal protein to which the fluorescent protein is attached in the cells may be transient or constitutive.

The "test compounds" brought into contact with the thus prepared cells are not particularly limited, and examples thereof include a synthetic low-molecular weight compound library, expression products of a gene library, a peptide library, antibodies, substances released from bacteria, an extraction liquid or culture supernatant of cells (microorganisms, plant cells, animal cells), purified or partially purified polypeptides, an extract from a marine organism, plant, or animal, soil, and a random phage peptide display library.

In general, the "contact" of the test compounds with the cells is conducted by adding each test compound to a culture liquid of the cells, but is not limited to this method. The concentration of each test compound brought into contact varies depending on the type and properties (solubility, toxicity, and the like) of the test compound. For example, in a case of a low-molecular weight compound, the concentration at which the compound is added to the culture liquid of the cells is preferably selected, as appropriate, within a range from 0.1 nM to 100 µM. In addition, the time for which the test compounds are kept into contact with the cells is preferably 10 minutes to 48 hours.

The "fluorescent bright spots due to aggregation of the lysosomal protein" formed in cells brought into contact with the test compound are bright spots formed when autophagosomes formed by fusion between the isolation membrane and trans-Golgi/endosome without using Atg5 or Atg7 fuse with the lysosomal protein to which the fluorescent protein is attached, and the fused products aggregate (are accumulated).

Detection of the formation of the fluorescent bright spots in the present invention can be conducted by, for example, observation with a fluorescence microscope equipped with an excitation filter and an absorption filter suitable for the fluorescent protein, an analysis using a flow cytometer, or an analysis using an imaging cytometer such as IN Cell Analyzer (manufactured by GE Healthcare). From the viewpoint that a high through put analysis can be achieved, the detection is preferably conducted by an analysis using an imaging cytometer.

The degree of the formation of the fluorescent bright spots can be evaluated, for example, based on the number of the fluorescent bright spots, the area of the fluorescent bright spots per cell, the ratio of the area of the fluorescent bright spots to that of cells expressing the lysosomal protein, and the like.

When the degree of the formation of the fluorescent bright spots is evaluated based on the area of the fluorescent bright spots per cell, it is preferable to use the fact that the area of the fluorescent bright spots per cell is 4 $\mu m^2$ or more (for example, 4 to 100 $\mu m^2$) as a criterion for selecting a compound having activity to induce alternative autophagy, from the viewpoint that the area of the fluorescent bright spots is less than 4 $\mu m^2$ in a cell in which no autophagy is observed.

In addition, as shown in FIG. 1, the fact that the area of the fluorescent bright spots per cell (the ratio of the area of the fluorescent bright spots to the intracellular area) has a proportional relationship with the fluorescence intensity per cell is first revealed by Examples of the present invention. Hence, it is also possible to use the fluorescence intensity, instead of the area (ratio), as an index for selecting a compound having activity to induce alternative autophagy.

For the selection of a compound having activity to induce alternative autophagy, it is also possible to use a relative evaluation based on comparison with a control, instead of such an absolute evaluation. Specifically, when the degree of the formation of the fluorescent bright spots in cells brought into contact with a test compound is higher than that of the cells not brought into contact with any test compound, the test compound can be selected as a compound having activity to induce alternative autophagy.

<Step of Selecting Compound Having Anticancer Activity by Using Activity to Induce Cell Death In Vitro as Index>

In addition to the above-described step (a), the method for screening for a compound having anticancer activity of the present invention preferably further comprises a step (step (b)) of bringing test compounds into contact with cells, and selecting a compound having activity to induce cell death by using, as an index, a survival rate of the cells after the contact. Thus, screening for a compound having high anticancer activity can be achieved more efficiently.

In general, programmed cell death of cells can be morphologically classified into apoptosis (type 1 cell death), autophagic cell death (type 2 cell death), and cell death (type 3 cell death) in which swelling of cell organelles and formation of vesicles occur, but lysosomes are not involved.

The "activity to induce cell death" in the step (b) may be activity to induce any type of the cell death, and is preferably activity to induce the autophagic cell death (type 2 cell death), from the viewpoint that a compound which exhibits anticancer activity against cancer cells having apoptosis resistance can be selected.

A method for detection for the "survival rate of cells" used as an index of the activity to induce cell death is not particularly limited, and is preferably not a method for specifically detecting apoptosis such as an annexin-V staining method or a propidium iodide (PI) staining method, but an apoptosis non-specific detection method such as, for example, a trypan blue dye exclusion test method, MTT assay, XTT assay, an alamar blue staining method, a tritiated thymidine uptake assay, a bromodeoxyuridine (BrdU) uptake assay, Cell Titer Blue (registered trademark, CTB) assay utilizing conversion of a redox dye, resazurin, to a fluorescent product, resorufin, in a living cell, or the like. The CTB assay is more preferable from the viewpoint that the cell death can be detected more simply with a high sensitivity.

The "cells" in the step (b) are not particularly limited, and, for example, primary cultured cells and immortalized cell can be used.

The "primary cultured cells" are cells obtained by culturing cells collected from a living organism and seeded for the first time. Those skilled in the art can prepare the primary cultured cells by selecting a known approach, as appropriate. Examples of the "immortalized cells" include cells immortalized by introduction of SV40T antigen, cells immortalized by introduction or activation of myc, ras, etc., and the like. Note that properties of these immortalized cells are known to be similar to those of cancer cells. In addition, those skilled in the art can prepare these cells by selecting, as appropriate, a known approach, as appropriate.

When primary cultured cells and immortalized cells are used, the selection of a compound having activity to induce cell death can be achieved by using, as a criterion, the fact that the survival rate of the primary cultured cells brought into contact with the test compound is 80% or higher, and the survival rate of the immortalized cells brought into contact with the test compound is 30% or lower.

In addition, it is also possible to use, for example, apoptosis resistant cells as the "cells" in the step (b). This enables efficient detection of programmed cell death different from apoptosis, and, in turn, selection of a compound having anticancer activity against cancer cells having apoptosis resistance.

Examples of the "apoptosis resistant cells" include cells in which a function of an apoptosis-inhibitory protein (Bcl-xL, Bcl-2, or the like) is enhanced, and cells in which a function of an apoptosis-inducing protein (Bax, Bak, Apaf-1, caspase-9, caspase-3, or the like) is suppressed. Those skilled in the art can prepare these cells by selecting a known approach, as appropriate. For example, when cells in which expression of an apoptosis-inhibitory prate in is enhanced are prepared, the same methods as those described for preparation of the cells expressing a lysosomal protein to which a fluorescent protein is attached can be employed. Meanwhile, when cells in which a function of an apoptosis-inducing protein is suppressed, the same methods as those described for preparation of the cells in which a function of Atg5 or the like is suppressed can be employed.

When the apoptosis resistant cells are used, the selection of a compound having activity to induce cell death can be conducted by using as a criterion the fact that the survival rate of the cells brought into contact with the test compound is 20% or less.

Moreover, as the "cells" in the step (b), cells in which a function of the p53 protein is suppressed can be used from the viewpoints that abnormality of p53 is detected in a half or more of the types of cancer, and that when a function of the p53 protein is suppressed, resistance to apoptosis induced by DNA damage or the like is acquired.

Those skilled in the art can prepare the "cells in which a function of the p53 protein is suppressed" by selecting, as appropriate, a known approach (for example, a method which is the same as the method for preparing the cells in which a function of Atg5 or the like is suppressed).

When the cells in which a function of the p53 protein is suppressed are used, the selection of the compound having activity to induce cell death can be conducted by using, as a criterion, the fact that the survival rate of the cells brought into contact with the test compound is 20% or less.

For the selection of the compound having activity to induce cell death in the step (b), it is also possible to use a relative evaluation based on comparison with a control, instead of the above-described absolute evaluation. Specifically, when the survival rate of cells brought into contact with a test compound is lower than that of the cells not brought into contact with any test compound, the test compound can be selected as a compound having activity to induce cell death.

Note that the "test compounds" and "contact" in the step (b) are the same as those in the above-described step (a).

<Step of Selecting Compound Having Anticancer Activity Using Activity to Induce Cell Death In Vivo as Index>

In addition to the above-described steps (a) and (b), the method for screening for a compound having anticancer activity of the present invention preferably further comprises a step (step (c)) of introducing the compound which is selected as the compound having activity to induce alternative autophagy in the step (a) and is selected as the compound having activity to induce cell death in the step (b) into a cancer-bearing non-human animal, measuring a size of the cancer borne by the cancer-bearing non-human animal, and selecting the test compound as a compound having anti-cancer activity, when an obtained measured value is smaller than a measured value of a size of the cancer borne by a cancer-bearing non-human animal into which the test compound is not introduced. This enables more efficient screening for a compound having high anticancer activity. Moreover, actual cancer treatment/prevention effects can be predicted by also investigating improvement in survival rate, the presence or absence of metastasis, and the like.

The "cancer-bearing non-human animal" in the step (c) is a non-human animal bearing cancer in the body thereof. The cancer is not particularly limited, and examples thereof include the above-described nasopharyngeal tumors and the like. The "non-human animal" bearing cancer only needs to be an animal other than human, and examples thereof include mouse, rat, monkey, chimpanzee, pig, sheep, goat, birds, zebrafish, frogs, and the like. Moreover, the cancer borne by the "cancer-bearing non-human animal" may be one developed spontaneously, or one prepared by irradiation with radiation, or introduction of a carcinogen (a chemical, a cancer virus, or a cancer gene). In addition, the cancer borne by the non-human animal may be one produced by introduction of cancer cells prepared outside the body, as shown in Example 3 described later. The relationship between the introduced cancer cells and the non-human animal may be allogeneic or xenogeneic.

In the step (c), the mode of administration by which the compound is introduced into the cancer-bearing non-human animal is not particularly limited, and examples thereof include direct administration such as injection to the cancer, as well as intravenous administration, intraarterial administration, subcutaneous administration, intradermal administration, intraperitoneal administration, oral administration, intratracheal administration, rectal administration, intramuscular administration, and the like. In addition, those skilled in the art can achieve the introduction into the cancer-bearing non-human animal by selecting a known approach (dosage form and the like) suitable for the mode of administration.

As for the "introduction of the compound" in the step (c), the compound is preferably introduced after the non-human animal bears the cancer as shown in Examples described later, from the viewpoint of screening for a compound suitable for cancer treatment. From the viewpoint of screening for a compound suitable for cancer prevention, for example, the compound is preferably introduced simultaneously with or prior to the introduction of the cancer cells prepared outside the body into the non-human animal.

The amount of the compound introduced into the cancer-bearing non-human animal is not particularly limited, and for example, the compound can be introduced at 0.1 nmol to 100 μmol/individual per introduction 1 to 5 times per day for 1 to 3 weeks every day or every few days (every 2 to 5 days). When the compound is introduced multiple times, the amount per introduction may be constant, but the introduced amount may be increased or decreased stepwise.

The "size of the cancer borne by the cancer-bearing non-human animal" detected in the step (c) may be not only the volume of the cancer, but also the longitudinal diameter or transverse diameter of the cancer, or the weight which reflects the volume of the cancer. Examples of the "measured value" obtained by measuring the size of the cancer borne by the cancer-bearing non-human animal includes not only an actually measured value, but also values of the volume calculated based on measured values of the longitudinal diameter and the like of the cancer.

When the measured value is smaller than a measured value of a size of the cancer borne by a cancer-bearing non-human animal into which the test compound is not introduced, the test compound can be selected as a compound having anticancer activity.

EXAMPLES

Hereinafter, the present invention is described more specifically on the basis of Examples. However, the present invention is not limited to Examples below.

Example 1

By using 11588 compounds provided from Chemical Biology Screening Center, Tokyo Medical and Dental University (http://www.tmd.ac.jp/mri/SBS/cbsc/CopyPlateList/CopyPlate.html) as test compounds, compounds having activity to induce alternative autophagy were selected by the following method using, as an index, formation of fluorescent bright spots due to aggregation of a lysosomal protein.

<Preparation of Lamp1-GFP Expressing Cells>

First, by using a retrovirus, a gene for expression of a Lamp1-GFP fusion protein (also referred to as "Lamp1-GFP") was introduced into ATG5-deficient mouse embryonic fibroblasts (also referred to as "ATG5-KO MEFs"). Then, a cell with high expression of Lamp1-GFP was cloned and prepared as Lamp1-GFP/ATG5-KO MEFs.

The ATG5-KO MEFs were prepared by introducing a gene for expression of SV40T antigen into MEFs established from an ATG5-deficient C57/B6J mouse at a fetal age of 14.5 days by an electroporation method using an Nucleofector system (manufactured by amaxa) for immortalization. In addition, the retrovirus was prepared by introducing an MSCV-Lamp1-GFP (zeocin resistant) vector into plat E cells, which were retrovirus packaging cells.

<Verification of Correlation Between Ratio of Aggregation of Lysosomal Protein in Cells and the Fluorescence Intensity of Fluorescent Bright Spots Due to Aggregation>

Investigation was made as to whether or not the degree of autophagy occurring in the Lamp1-GFP expressing cells, i.e., the area of the aggregation of the Lamp1-GFP per cell has a correlation with the fluorescence intensity of fluorescent bright spots due to the aggregation of Lamp1-GFP.

Specifically, first, alternative autophagy was induced in Lamp1-GFP expressing cells by giving etoposide at 10 μM. Then, 16 hours after the treatment to induce alternative autophagy was conducted, the cells were fixed with glutaraldehyde. Then, the amount of GFP fluorescence per cell was quantitatively determined by using In Cell Analyzer. After that, the same samples were observed with an electron microscope, and the area of aggregation of Lamp1-GFP per cell (the area of autophagy region) was calculated. FIG. 1 shows the obtained results.

As is apparent from the results shown in FIG. 1, it was shown that the area of the autophagy region measured with the electron microscope had a proportional relationship with the fluorescence intensity of fluorescent bright spots due to the aggregation of Lamp1-GFP per cell. Hence, it has been shown that the degree of autophagy can also be evaluated by using, as an index, the fluorescence intensity of fluorescent bright spots due to the aggregation of Lamp1-GFP.

<Evaluation of Activity to Induce Alternative Autophagy>

To the Lamp1-GFP/ATG5-KO MEFs seeded at $1\times10^4$/96 wells on the preceding day, each of the test compounds was added at a final concentration of 50 μM, and the Lamp1-GFP/ATG5-KO MEFs were cultured at 37° C. under 10% $CO_2$ for 5 hours.

Then, for observation, Hoechst 33342 (manufactured by invitrogen) was added at a final concentration of 1 ng/ml to each culture liquid, followed by incubation for 5 minutes. Then, the culture liquid was replaced with 100 μl of HBSS. Subsequently, five visual fields per well were photographed at random with IN CELL ANALYZER 1000 (manufactured by GE Healthcare). Then, each test compound which resulted in an area per cell of the fluorescent bright spots due to the aggregation of Lamp1-GFP of 4 μm$^2$ or more in the obtained observation visual fields was selected as a compound having activity to induce alternative autophagy.

As a result, in Example 1, 54 compounds among the tested 11588 compounds were selected as compounds having activity to induce alternative autophagy.

Example 2

By using the 11588 compounds provided from Chemical Biology Screening Center, Tokyo Medical and Dental University as test compounds, compounds having activity to induce cell death were selected by the following method using a survival rate of cells as an index.

<Selection of Compounds Inducing Cell Death Specifically to Cancer Cells>

In this Example, compounds inducing cell death specifically to cancer cells were selected by using primary cultured wild-type MEFs (primary MEFs) having a low growth rate and transformed MEFs immortalized by introducing the SV40T antigen and having a high growth rate. Specifically, first, the transformed MEFs were seeded at $2\times10^4$/well and the primary MEFs were seeded at $4\times10^4$/well on 96-well plates. Then, on the following day, each compound was added at a final concentration of 50 μM, and the primary MEFs and transformed MEFs were cultured at 37° C. under 10% $CO_2$ for 24 hours. Subsequently, the survival rate of the cells brought into contact with each test compound was measured by using Cell titer blue (CTB) (manufactured by Promega) according to the attached protocol. Then, test compounds each of which greatly induced cell death in the transformed MEFs (with a survival rate of 30% or lower) and did not induce cell death in the primary MEFs (with a survival rate of 80% or higher) were selected as compounds inducing cell death specifically to cancer cells. As a result, in Example 2, 411 compounds were selected among the tested 11588 compounds.

Example 3

By using, as test compounds, 24 compounds selected in Example 1 and also selected in Example 2 from the 11588 compounds, compounds having anticancer activity were selected by the method using cancer-bearing non-human animal shown below.

<Selection of Compounds Having In Vivo Anticancer Activity>

Figure 2:
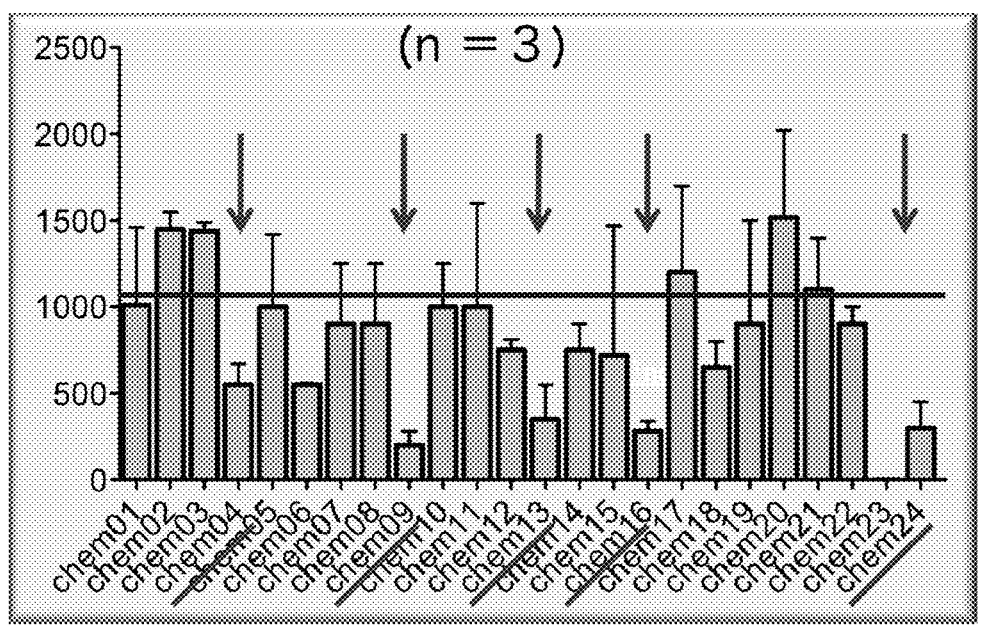
FIG. 2 is a graph showing tumor volumes (mm³) 20 days after 24 compounds selected as compounds having activity to induce alternative autophagy and activity to induce cell death by a method of the present invention were administered to cancer-bearing mice.
Figure 3:
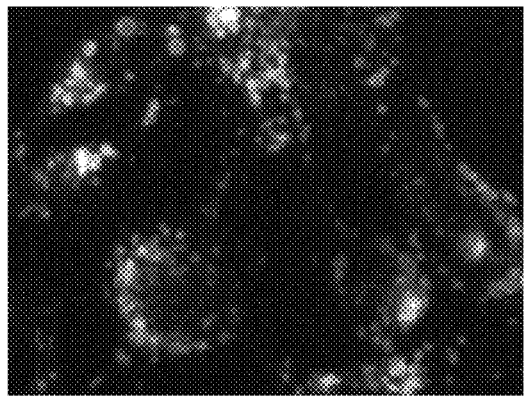
FIG. 3 is a fluorescence micrograph showing an observation result of aggregation of a lysosomal protein Lamp2 in p53-deficient cancer cells (53T) brought into contact with compound #09 (a benzothiophene compound according to the present invention) selected by the method of the present invention.
Figure 4:
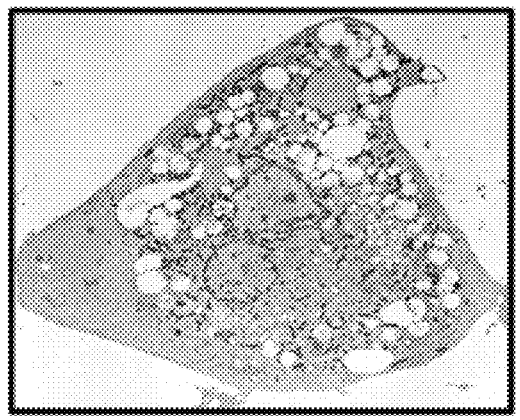
FIG. 4 is an electron micrograph showing an observation result of occurrence of autophagy in p53-deficient cancer cells (53T) brought into contact with compound #09 selected by the method of the present invention.
Figure 5:
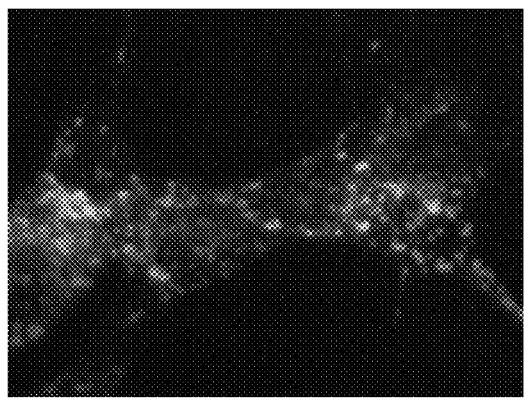
FIG. 5 is a fluorescence micrograph showing an observation result of aggregation of the lysosomal protein Lamp2 in p53-deficient cancer cells (53T) brought into contact with compound #13 selected by the method of the present invention.
Figure 6:
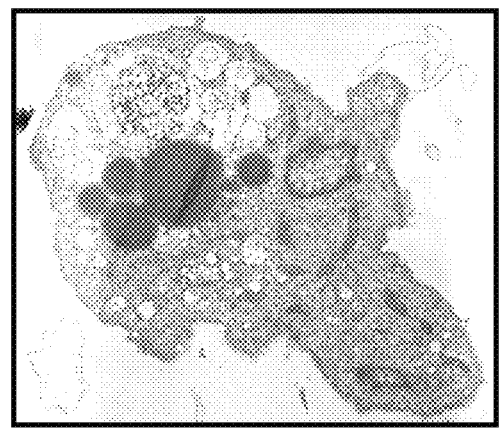
FIG. 6 is an electron micrograph showing an observation result of occurrence of autophagy in p53-deficient cancer cells (53T) brought into contact with compound #13 selected by the method of the present invention.

A tumor cell line (also referred to as "53T") established from a tumor developed spontaneously in a p53 deficient C57/B6J mouse was implanted at 4 sites in the ventral skin of each of wild-type C57/B6J mice at $3\times10^5$ cells per site. From the following day, the compounds were administered to the mice every other day five times in total. The concentration of each compound was 0.4 μmol/(50 μl DMSO+100 μl PBS)/mouse/administration. In addition, a negative control group to which only the same amount of DMSO was administered was prepared. Then, 21 days (3 weeks) after the implantation, the tumor diameters of the mice were measured, and the tumor volumes were calculated, and compared with that of the control group. FIG. 2 shows the obtained results. Note that, in FIG. 2, the vertical axis represents the average value ($mm^3$) of the tumor volumes, and the line in parallel with the horizontal axis at around 1000 $mm^2$ shows the average value of the tumor volumes of the negative control group.

As is apparent from the results shown in FIG. 2, 5 compounds (chem04, chem09, chem13, chem16, and chem24) were selected as compounds having in vivo anticancer activity, among the 24 compounds selected in Example 1 and also selected in Example 2.

Example 4

Alternative autophagy-inducing activity of each of Chem09 and chem13 selected in Example 3 was tested by a method using a tumor cell line shown below.

Chem09 and chem13 are also referred to as "compound #09" and "compound #13," respectively. In addition, the structures of the compounds are as follows. Note that the compounds #09 (STOCK3S-94453) and #13 (STOCK4S-32811) purchased from a supplier IBS were used in this Example and the following Examples.

[Chem. 19]

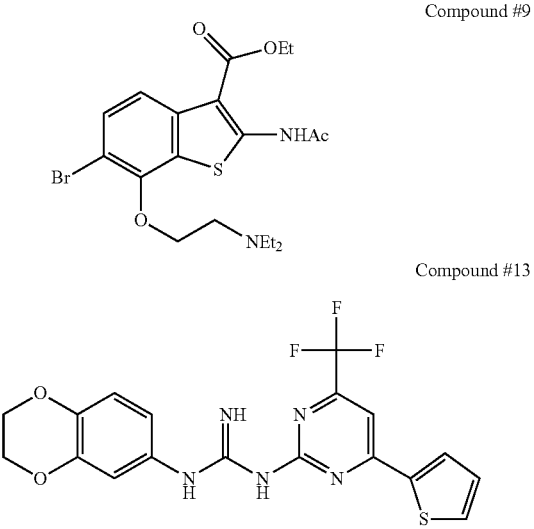

Compound #9

Compound #13

In the above-described formulae, "Et" represents an ethyl group ($C_2H_5$ group), and "Ac" represents an acetyl group ($C(=O)CH_3$ group) (hereinafter the same shall apply).

<Evaluation of Alternative Autophagy-Inducing Activity>

In the same manner as in the above-described <Evaluation of Alternative Autophagy-Inducing Activity> using the Lamp1-GFP/ATG5-KO MEFs, each of the compounds #09 and #13 was added at a final concentration of 20 μM to a culture liquid of the tumor cell line (also referred to as "53T") established from the tumor developed spontaneously in the p53 deficient C57/B6J mouse. Six hours later, the tumor cell line was observed with a fluorescence microscope and an electron microscope. Note that, in this evaluation, Lamp2 was used instead of Lamp1. FIGS. 3 to 6 show the obtained results.

As is apparent from the results shown in FIGS. 3 to 6, aggregation of the lysosomal protein Lamp2 and occurrence of autophagy were observed in the p53-deficient cancer cells to which compound #09 or #13 was administered. Hence, it was shown that the compounds (compounds #09 and #13) selected by the screening method of the present invention were capable of inducing alternative autophagy in the cancer cells.

Example 5

The anticancer activity of compounds #09 and #13 was tested by a method using a tumor cell line shown below.

<Evaluation of In Vitro Anticancer Activity>

First, the mouse tumor cell line 53T was seeded at $2\times10^4$/well on 96 well plates. Then, on the following day, each of compounds #09 and #13 dissolved in DMSO was added at a final concentration of 1, 5, 10, 20, or 50 μM. In addition, a negative control to which only DMSO was added was prepared. Subsequently, the cells were cultured at 37° C.

under 10% $CO_2$ for 24 hours. Then, by using Cell titer blue (CTB) (manufactured by Promega) according to the attached protocol, the amount of the fluorescence of each well of the cells 10 minutes after the addition of the CTB reagent was measured as a CTB measurement value of the cells brought into contact with compound #09 or #13. On the basis of such measurement values, the cell death induction rate of each of compounds #09 and #13 was calculated according to the following formula.

Cell death induction rate=(CTB measurement value of negative control−CTB measurement value of cells to which compound was added)/CTB measurement value of negative control Table 1 shows the obtained results.

TABLE 1

|  | 1 μM | 5 μM | 10 μM | 20 μM | 50 μM |
| --- | --- | --- | --- | --- | --- |
| Compound #09 | 0 | 0.07741 | 0.172515 | 0.630546 | 0.945621 |
| Compound #13 | 0 | 0.177583 | 0.455927 | 0.767985 | 0.942624 |

As is apparent from the results shown in Table 1, it was shown that the stimulation with each of compounds #09 and #13 at a final concentration of 50 μM for 24 hours successfully induced cell death of 90% or more of the cells of the tumor cell line. Hence, it has been found that the screening method of the present invention makes it possible to select a compound having anticancer activity.

Example 6

Investigation was made as to whether or not the cell death-inducing activity of each of compounds #09 and #13 was specific to cancer cells, by a method using normal cells and cancer cells shown below.

<Evaluation of Activity to Induce Cell Death Specific to Cancer Cells>

Figure 7:
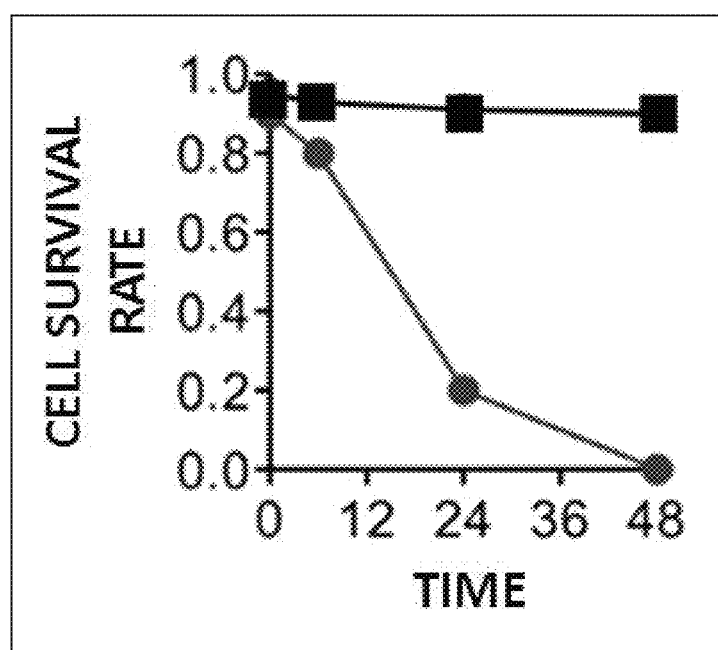
FIG. 7 is a graph showing the survival rates of normal cells and cancer cells brought into contact with compound #09 selected by the method of the present invention. Note that, in the graph, each square represents the survival rate of the normal cells, and each circle represents the survival rate of the cancer cells.
Figure 8:
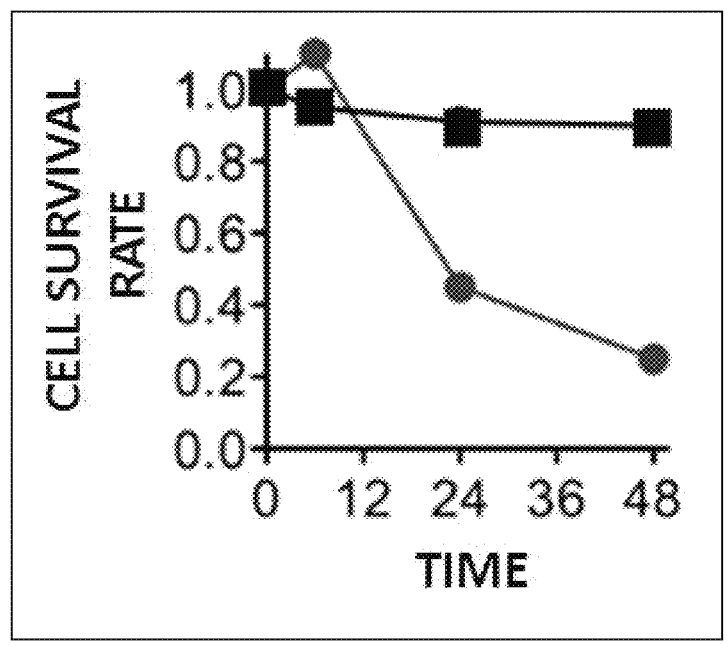
FIG. 8 is a graph showing the survival rates of normal cells and cancer cells brought into contact with compound #13 selected by the method of the present invention. Note that, in the graph, each square represents the survival rate of the normal cells, and each circle represents the survival rate of the cancer cells.

CTB measurement values were obtained in the same manner as in the above-described <Evaluation of In Vitro Anticancer Activity> by adding each of compounds #09 and #13 at a final concentration of 20 μM to culture liquids of primary cultured fibroblasts (normal cells) and fibroblasts (cancer cells) immortalized with SV40. On the basis of the obtained CTB measurement values, the cell survival rate was calculated over time. Note that the cell survival rate was defined as 1-cell death induction rate. FIGS. 7 and 8 show the obtained results.

As is apparent from the results shown in FIGS. 7 and 8, each of compounds #09 and #13 hardly induced cell death of the normal cells, but exhibited remarkable cell death-inducing activity on the cancer cells. Hence, it was found that the compounds (compounds #09 and #13) selected by the screening method of the present invention successfully induced cell death specific to the cancer cells.

Example 7

In vivo anticancer activity of each of compounds #09 and #13 was tested by a method using cancer-bearing mice shown below.

<Selection of Compounds Having In Vivo Anticancer Activity>

Figure 9:
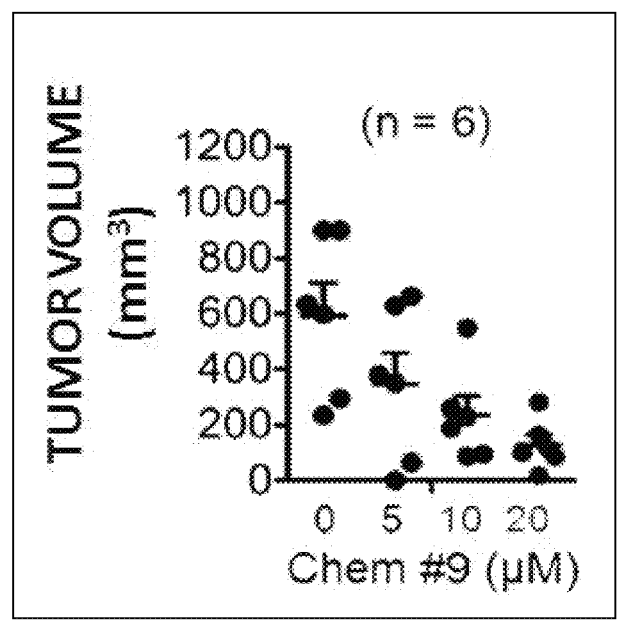
FIG. 9 is a plot showing tumor volumes in cancer-bearing mice to which compound #09 selected by the method of the present invention was introduced.
Figure 11:
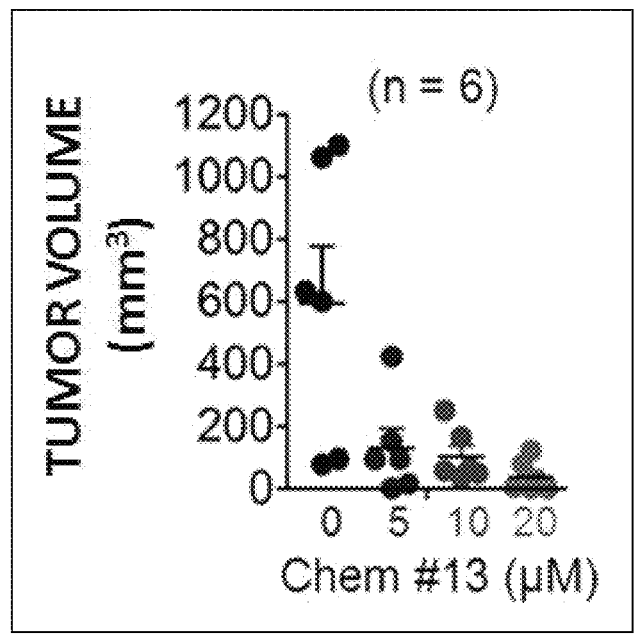
FIG. 11 is a plot showing tumor volumes in cancer-bearing mice to which compound #13 selected by the method of the present invention was introduced.

The 53T was implanted at 4 sites in the ventral skin of each of wild-type C57/B6J mice at $3 \times 10^5$ cells per site. From the following day, 0 (DMSO alone), 5, 10, or 20 μM of each of compounds #09 and #13 was administered to six mice every other day five times in total. Then, 21 days (3 weeks) after the implantation, the tumor diameters of the mice were measured, and the tumor volumes were calculated. FIGS. 9 and 11 show the obtained results. Note that, in FIGS. 9 and 11, each point indicates the average volume of the tumors at the four sites in a mouse.

Figure 10:
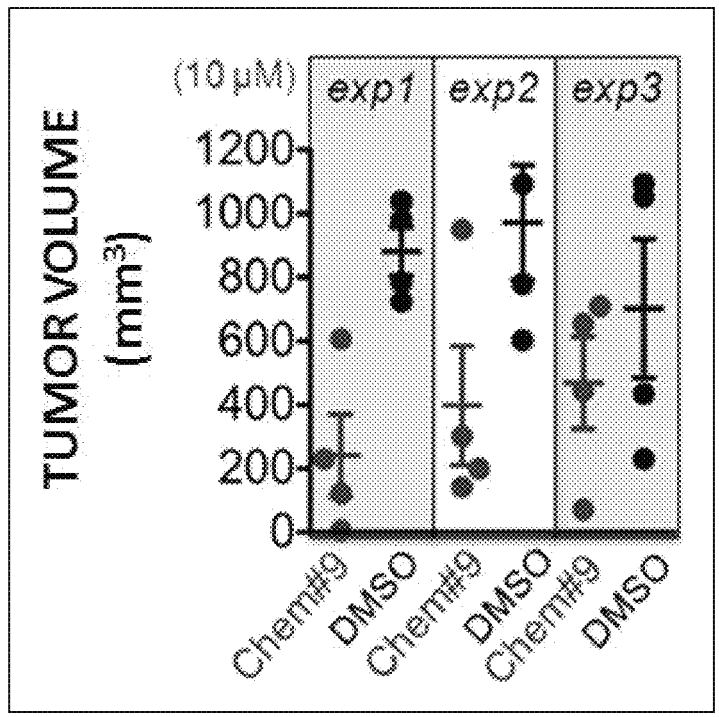
FIG. 10 is a plot showing tumor volumes in cancer-bearing mice to which compound #09 selected by the method of the present invention was introduced.
Figure 12:
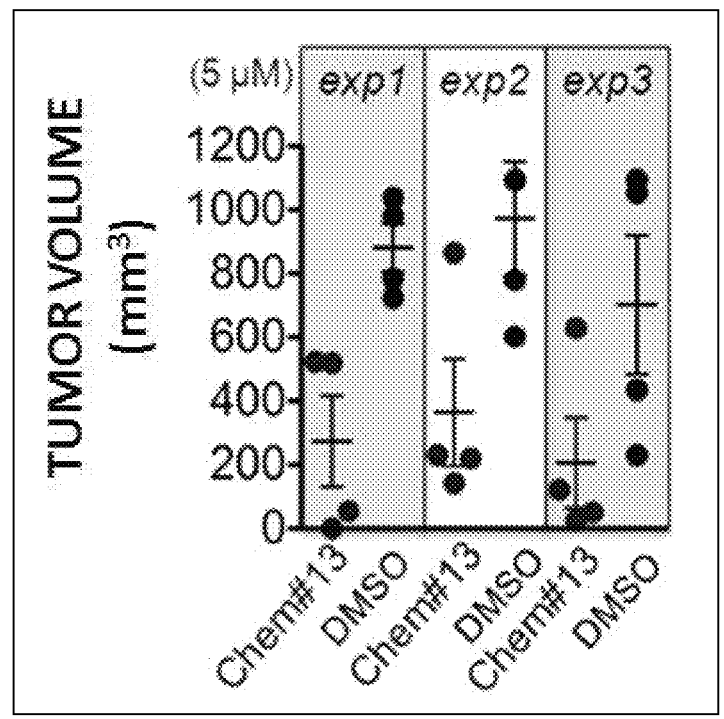
FIG. 12 is a plot showing tumor volumes in cancer-bearing mice to which compound #13 selected by the method of the present invention was introduced.

In addition, in the same manner as described above, the 53T was implanted in mice, and, from the following day, each of compound #09 at a concentration of 10 μM and compound #13 at a concentration of 5 μM was administered to four cancer-bearing mice every other day five times in total. Then, 21 days (3 weeks) after the implantation, the tumor diameters of the mice were measured, and the tumor volumes were calculated. In addition, a negative control to which DMSO was administered was also prepared, and the tumor volume was calculated in the same manner. In addition, these experiments were conducted three times independently of each other. FIGS. 10 and 12 show the obtained results. Note that in FIGS. 10 and 12, each point indicates the average volume of the tumors at the four sites in a mouse.

As is apparent from the results shown in FIGS. 9 to 12, both compounds #09 and #13 exhibited in vivo anticancer activity. In particular, as shown in FIG. 9, it was shown that the anticancer activity of compound #09 was dose-dependent activity. In addition, as shown in FIG. 11, it was found that compound #13 exhibited remarkable anticancer activity, even when administered at a low concentration of 5 μM.

Example 8

Figure 13:
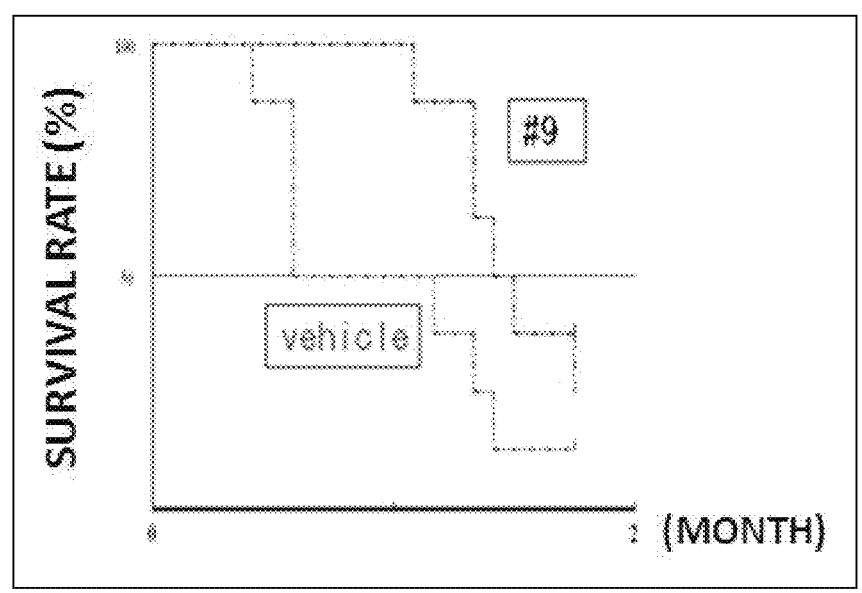
FIG. 13 is a graph showing change in survival rate of cancer-bearing mice to which compound #09 selected by the method of the present invention was introduced. Note that, in the graph, "vehicle" represents change in survival rate of cancer-bearing mice (negative control) to which DMSO was administered (the same shall apply in FIGS. 14 and 15).
Figure 14:
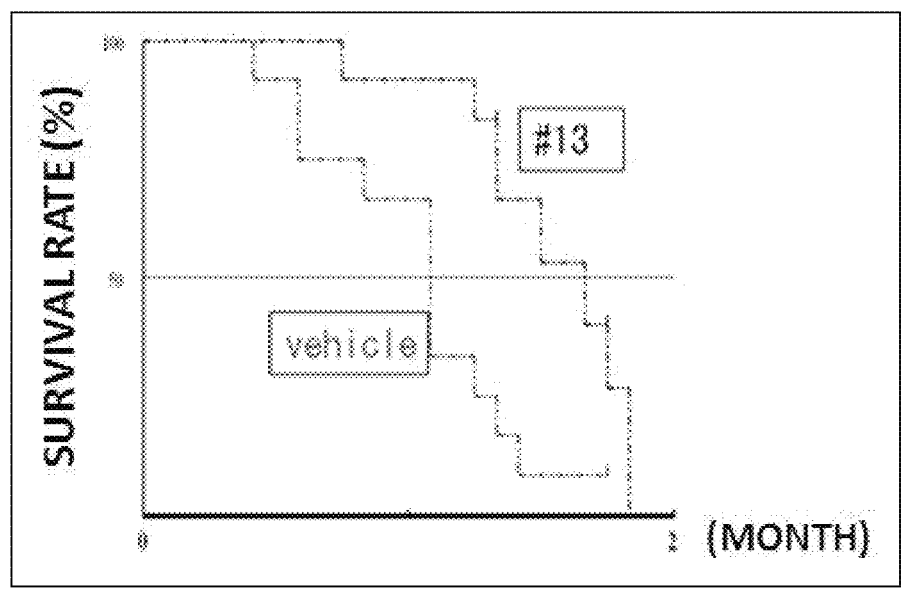
FIG. 14 is a graph showing change in survival rate of cancer-bearing mice to which compound #13 selected by the method of the present invention was introduced.
Figure 15:
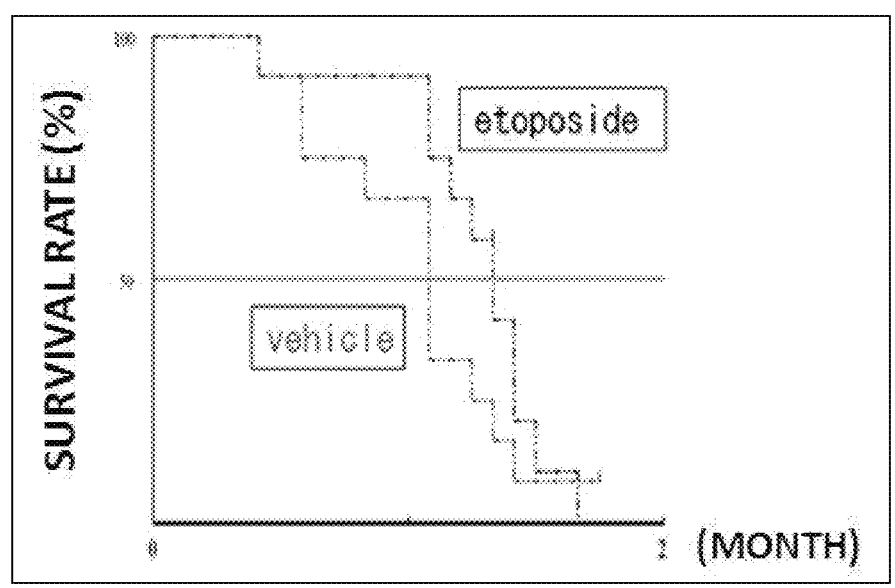
FIG. 15 is a graph showing change in survival rate of cancer-bearing mice to which an anticancer agent etoposide was introduced.

The survival rate of cancer-bearing mice to which compound #09 or #13 was administered was investigated by a method shown below. In addition, as a control, etoposide, which had been already clinically used as an anticancer agent, was administered to cancer-bearing mice, and the survival rate thereof was investigated. Specifically, in the same manner as in the above-described <Selection of Compounds having In Vivo Anticancer Activity>, the 53T was implanted at 4 sites in the ventral skin of each of wild-type C57/B6J mice at $3 \times 10^5$ cells per site. From the following day, each of compounds #09 and #13 was administered at 10 μM to 12 cancer-bearing mice every other day 5 times in total. In addition, as a control, etoposide was administered at 10 μM to cancer-bearing mice. Moreover, as a negative control, a group to which DMSO was administered was also prepared. In addition, the survival rates of these cancer-bearing mice were investigated, and a survival curve after the administration of each compound was obtained. FIGS. 13 to 15 show the obtained results.

As is apparent from the results shown in FIGS. 13 to 15, each of compounds #09 and #13 showed a higher improvement effect on the survival rate of the cancer-bearing mice than etoposide. Hence, it has been found that the screening method of the present invention makes it possible to select a compound having a stronger therapeutic effect on cancer than an already-existing anticancer agent. In addition, it has been shown that compound #09 has a stronger therapeutic effect on cancer than an already-existing anticancer agent.

Example 9

Figure 16:
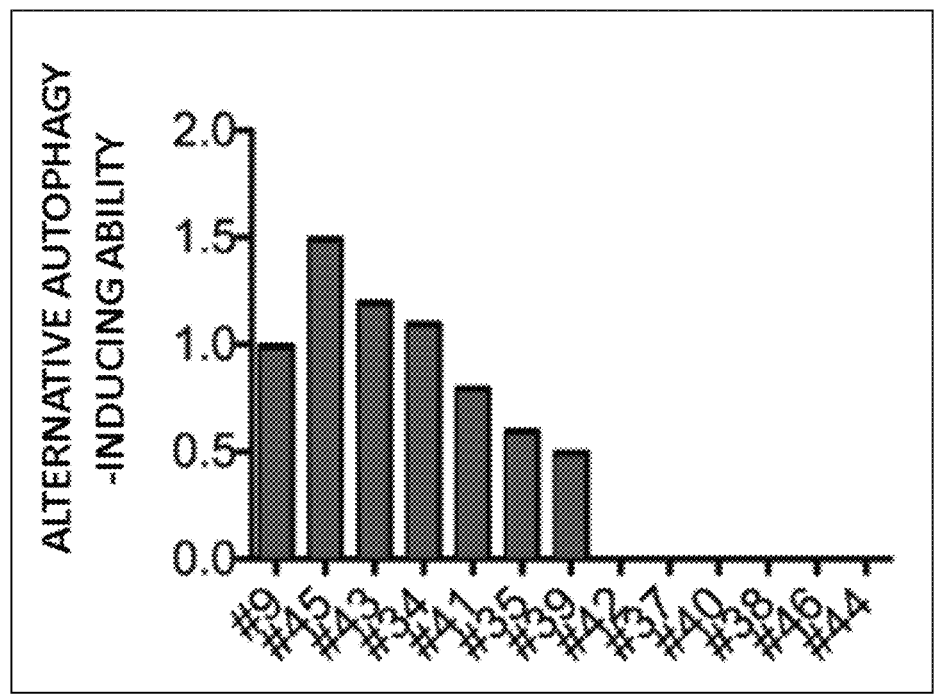
FIG. 16 is a graph showing alternative autophagy-inducing ability of compound #09 and analogous compounds thereof (compounds #34, #35, #37, #38, #39, #40, #41, #42, #43, #44, #45, and #46). Note that, in the graph, the vertical axis represents the relative activity value obtained by evaluating the autophagy area per cell in each of the cases where these compounds were added (the area of fluorescent bright spots due to aggregation of Lamp1-GFP in a cell) with the autophagy area in the case where compound #09 was added taken as 1.
Figure 17:
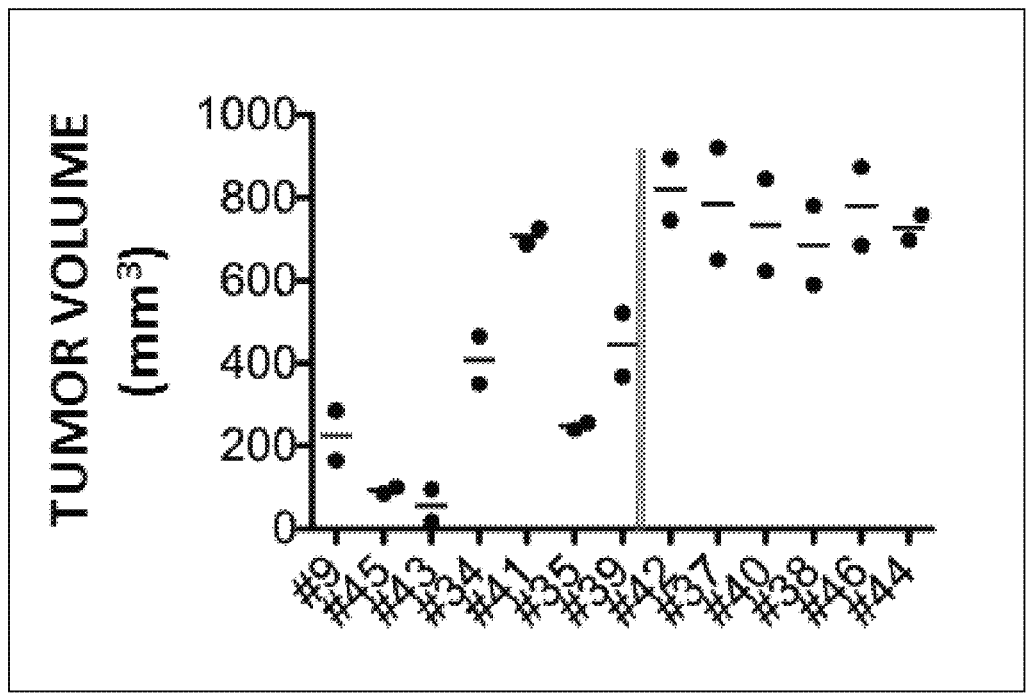
FIG. 17 is a plot showing tumor volumes in cancer-bearing mice to which compound #09 or an analogous compound thereof (compound #34, #35, #37, #38, #39, #40, #41, #42, #43, #44, #45, or #46) was introduced.

The ability to induce alternative autophagy of each of Compound #09 and analogous compounds thereof was evaluated by the same method as that described in Example 1. In addition, the anticancer activity of each of these compounds was evaluated by the same method as that described in Example 5. FIGS. 16 and 17 show the obtained results. The structures of compound #09 and the analogous compounds thereof are as follows. Note that those analogous compounds were purchased from Pharmeks Ltd. (RUSSIA).
[Chem. 20]
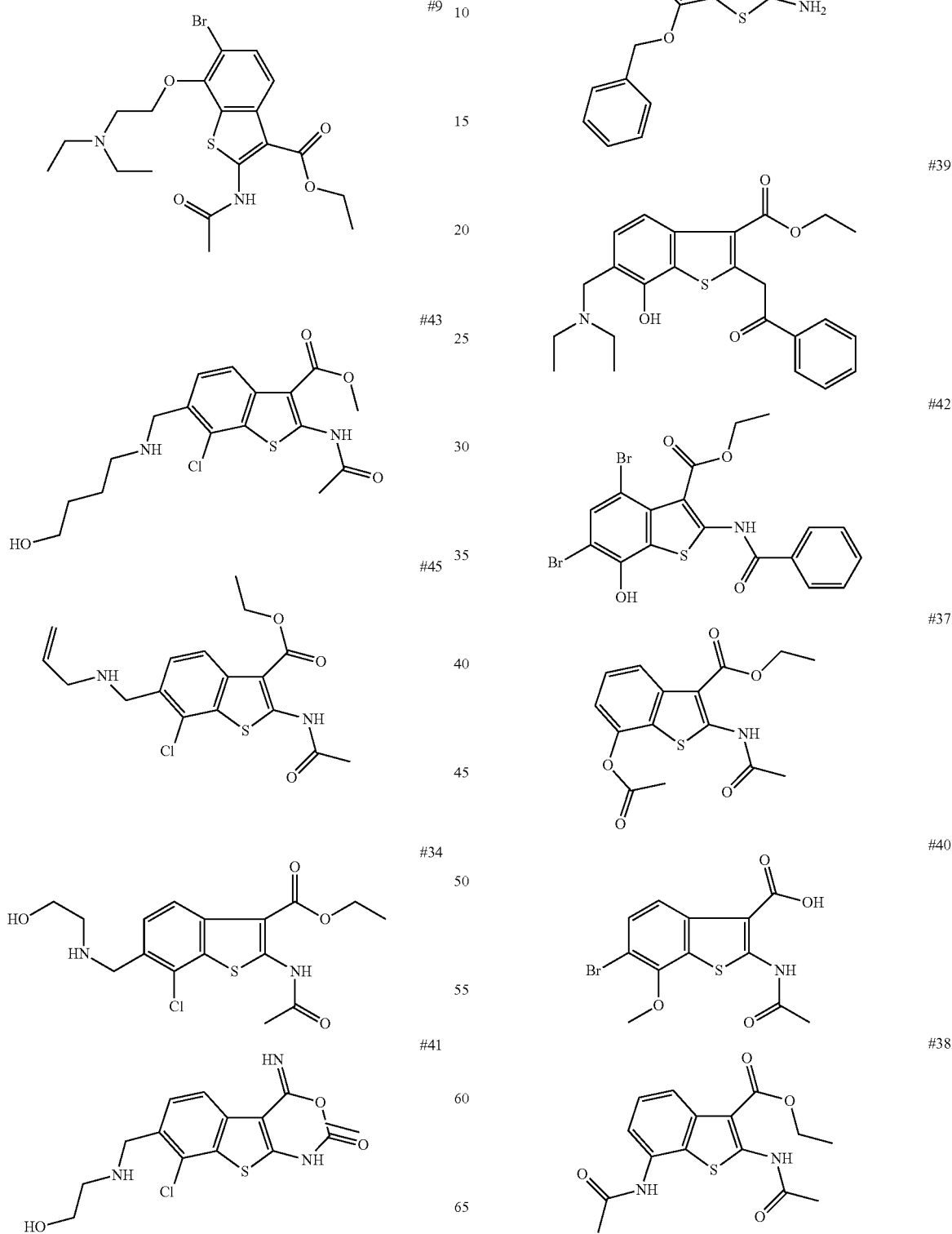

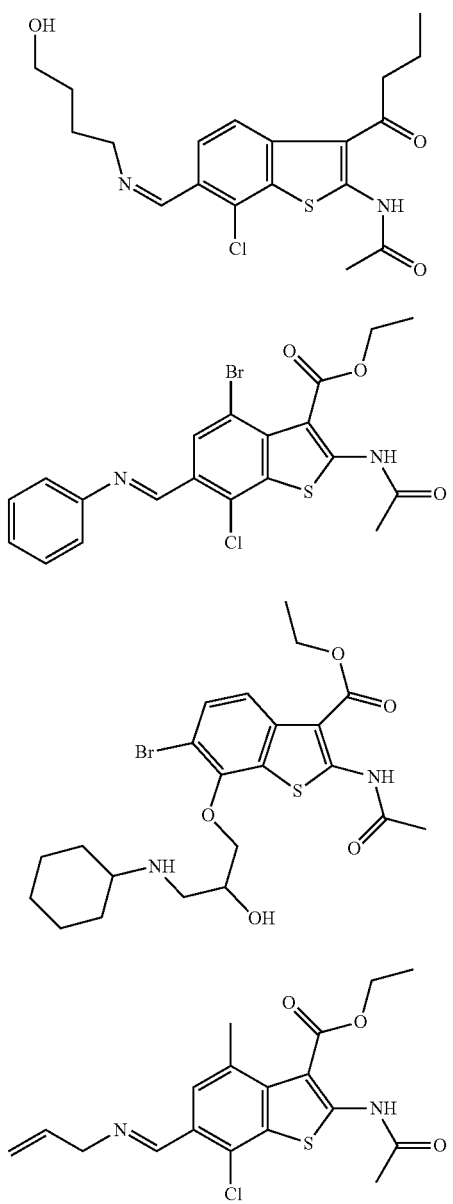

46

44

36

47

As is apparent from the results shown in FIGS. 16 and 17, it was found that analogous compounds (compounds #37, #38, #40, #42, #44, and #46) of compound #09 having no alternative autophagy-inducing activity did not have anticancer activity. On the other hand, it was found that compound #09 and almost all analogous compounds thereof having alternative autophagy-inducing activity had anticancer activity. Note that each of compounds #36 and #47 exhibited a strong cell-killing effect (necrosis) even when added at a low concentration, and hence was determined to be difficult to administer to a living organism because of the high toxicity.

Therefore, the usefulness of the step of selecting a compound having activity to induce autophagy by using, as an index, formation of fluorescent bright spots due to aggregation of a lysosomal protein in the screening method of the present invention is demonstrated.

Example 10

As analogous compounds of compound #09, novel benzothiophene compounds (TMD-459 and TMD-460) having the following structural formulae were designed and synthesized.

[Chem. 21]

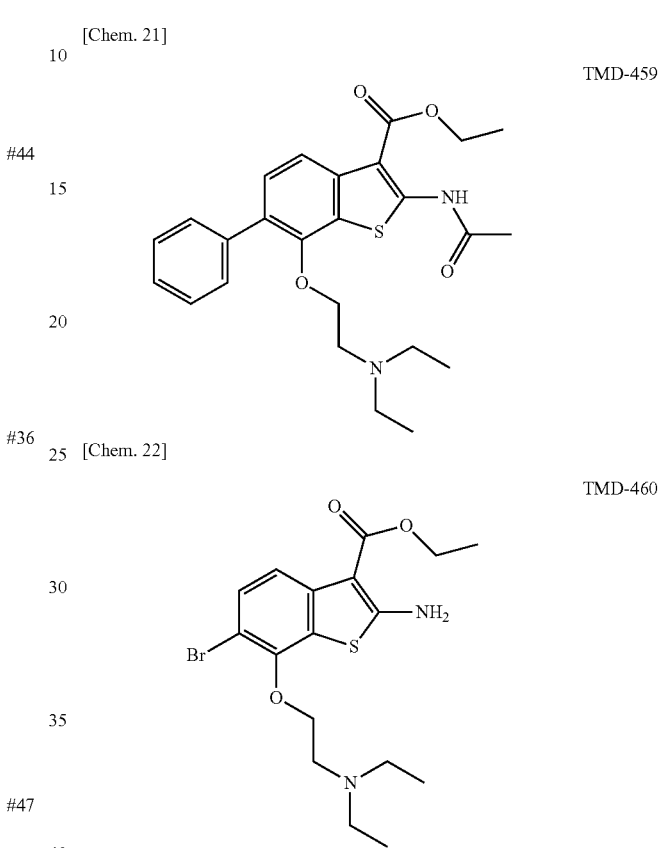

TMD-459

[Chem. 22]

TMD-460

Specifically, by using materials and methods shown below, first, ethyl 2-acetylamino-6-bromo-7-hydroxybenzo[b]thiophene-3-carboxylate was synthesized according to the description shown in "Grinev. A. N. et al., "Synthesis of 2-(acylamino)-7-hydroxybenzo[b]thiophene derivatives, bromination and nitration", Khimiya Geterotsiklicheskikh Soedinenii, 1987, vol. 4, pp. 460 to 462,", and converted to compound #9. Next, TMD-459 and TMD-460 were synthesized from compound #9.

<Materials and Methods>

(1) Chromatography

Analytical thin-layer chromatography (TLC) was conducted by using glass plates (MERCK 5715, silica gel 60 $F_{254}$) to which silica gel was applied beforehand. Spot detection was conducted with an ultraviolet lamp (254 nm), by iodine adsorption, and by staining with an aqueous potassium permanganate solution.

Preparative flash column chromatography was conducted with a medium pressure preparative liquid chromatograph (Yamazen Corporation, EPCLC-W-Prep 2XY A-Type) by using silica gel (Wako Pure Chemical Industries, Ltd., 295-34061, Presep® (Luer Lock) Silica Gel (HC-N) Type L).

For preparative thin-layer chromatography, glass plates on which silica gel (MERCK 1.07747.2500, silica gel 60 F$_{254}$) was applied were prepared and used.

(2) Nuclear Magnetic Resonance (NMR) Spectra $^1$H nuclear magnetic resonance (NMR) spectra (500 MHz) were measured by using a nuclear magnetic resonance apparatus, AVANCE 500, manufactured by Bruker. The chemical shifts (δ) are expressed as relative values by using tetramethylsilane ((CH$_3$)$_4$Si) (measurement in CDCl$_3$: 0 ppm) or a peak due to residual protons in the solvent for measurement (measurement in CD$_3$OD: 3.31 ppm; measurement in DMSO-d$_6$: 2.49 ppm) as an internal standard. The abbreviations s, d, t, q, m, and br for signal splitting patterns stand for singlet, doublet, triplet, quartet, multiplet, and broad, respectively.

$^{13}$C nuclear magnetic resonance spectra (126 MHz) were measured by using a nuclear magnetic resonance apparatus, AVANCE 500, manufactured by Bruker. Chemical shifts (δ) are expressed as relative values by using a peak due to a carbon of the solvent for measurement (measurement in CDCl$_3$: 77.0 ppm; measurement in CD$_3$OD: 49.0 ppm) as an internal standard.

(3) Chemicals

Unless otherwise noted, all reagents were commercially available products, and were used as purchased. As solvents for reactions, extraction, and chromatography, commercially available products of ethyl acetate, n-hexane, anhydrous dichloromethane, anhydrous tetrahydrofuran (THF), methanol, 1,4-dioxane, acetic acid, and N,N-dimethylformamide (DMF) were used as purchased.

The following reaction reagents were used. Ethyl 2-amino-4,5,6,7-tetrahydrobenzo[b]thiophene-3-carboxylate (Cat. No. 325-89562), acetic anhydride (Cat. No. 011-00276), acetic acid (Cat. No. 017-00256), potassium dichromate (Cat. No. 163-03665), bromine (Cat. No. 020-02403), sodium thiosulfate (Cat. No. 197-03585), potassium carbonate (Cat. No. 162-03495), and sodium hydroxide (Cat. No. 198-13765) were purchased from Wako Pure Chemical Industries, Ltd., and N-(2-chloroethyl) diethylamine hydrochloric acid salt (Cat. No. C0302) was purchased from Tokyo Chemical Industry Co., Ltd. These reaction reagents were used as purchased for reactions.

(4) Synthesis of Ethyl 2-Acetylamino-4,5,6,7-tetrahydrobenzo[b]thiophene-3-carboxylate

[Chem. 23]

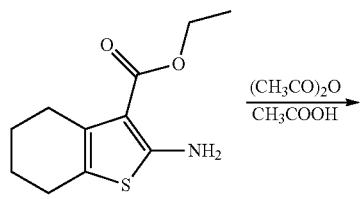

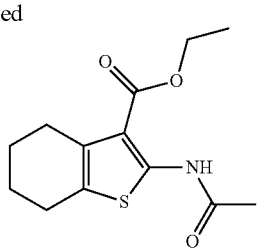

A mixture of ethyl 2-amino-4,5,6,7-tetrahydrobenzo[b]thiophene-3-carboxylate (25 g, 111 mmol), acetic acid (150 mL), and acetic anhydride (19 mL, 200 mmol) was stirred at 85° C. for 24 hours. To this reaction solution, 100 mL of water was added, and the precipitates were collected by filtration to obtain ethyl 2-acetylamino-4,5,6,7-tetrahydrobenzo[b]thiophene-3-carboxylate (30 g, quant.) as a white solid: TLC $R_f$=0.38 (n-hexane/ethyl acetate=3/1); $^1$H NMR (500 MHz, CDCl$_3$) δ 1.38 (t, J=7.0 Hz, 3H), 1.76-1.81 (m, 4H), 2.25 (s, 3H), 2.63 (t, J=4.5 Hz, 2H), 2.76 (t, J=4.5 Hz, 2H), 4.32 (q, J=7.0 Hz, 2H), 11.26 (br s, 1H); $^{13}$C NMR (126 MHz, CDCl$_3$) δ 14.5, 23.1, 23.2, 23.9, 24.6, 26.6, 60.7, 111.5, 126.9, 130.9, 147.8, 166.9, 167.1.

(5) Synthesis of Ethyl 2-Acetylamino-4,5,6,7-tetrahydro-7-oxobenzo[b]thiophene-3-carboxylate

[Chem. 24]

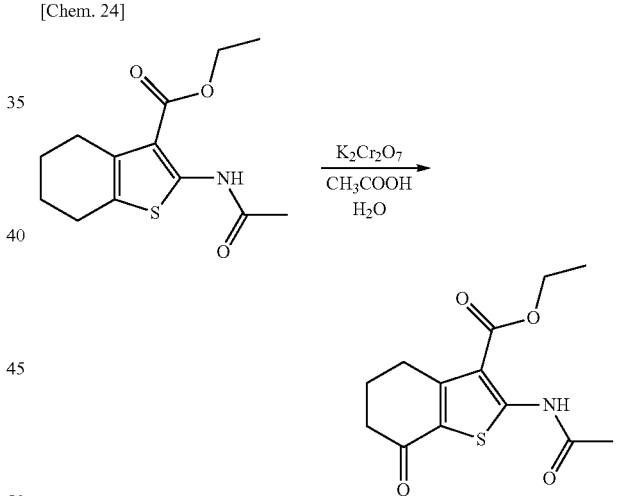

To ethyl 2-acetylamino-4,5,6,7-tetrahydrobenzo[b]thiophene-3-carboxylate (6.6 g, 25 mmol), acetic acid (35 mL) was added, followed by heating to 60° C. Then, a suspension of potassium dichromate (10 g, 52 mmol) and distilled water (10 mL) was slowly added, while keeping the reaction mixture below 80° C., followed by stirring at 60° C. for 24 hours. To this reaction mixture, aqueous sodium hydrogencarbonate was added, and extraction with ethyl acetate was conducted (×3). The organic layer was washed with saturated aqueous sodium chloride (×1) sequentially, and dried over anhydrous sodium sulfate. After filtration, the organic layer was concentrated under vacuum, and the residue was purified by silica gel flash column chromatography (n-hexane/ethyl acetate=4/1, and then ethyl acetate alone). Thus, ethyl 2-acetylamino-4,5,6,7-tetrahydro-7-oxobenzo[b]thiophene-3-carboxylate (2.73 g, 9.7 mmol, 39%) was obtained as a white solid: TLC $R_f$=0.48 (n-hexane/ethyl acetate=1/1); $^1$H NMR (500 MHz, CDCl$_3$) δ 1.43 (t, J=7.0 Hz, 3H), 2.16 (quin, J=6.5 Hz, 2H), 2.32 (s, 3H), 2.57 (t, J=6.5 Hz, 2H), 3.07 (t, J=6.5 Hz, 2H), 4.39 (q, J=7.0 Hz, 2H), 11.55 (br s, 1H); $^{13}$C NMR (126 MHz, CDCl$_3$) δ 14.5, 24.0, 26.8, 37.9, 61.5, 112.1, 127.7, 150.1, 156.2, 166.3, 167.9, 192.7.

(6) Synthesis of Ethyl 2-Acetylamino-6-bromo-7-hydroloxybenzo[b]thiophene-3-carboxylate

[Chem. 25]

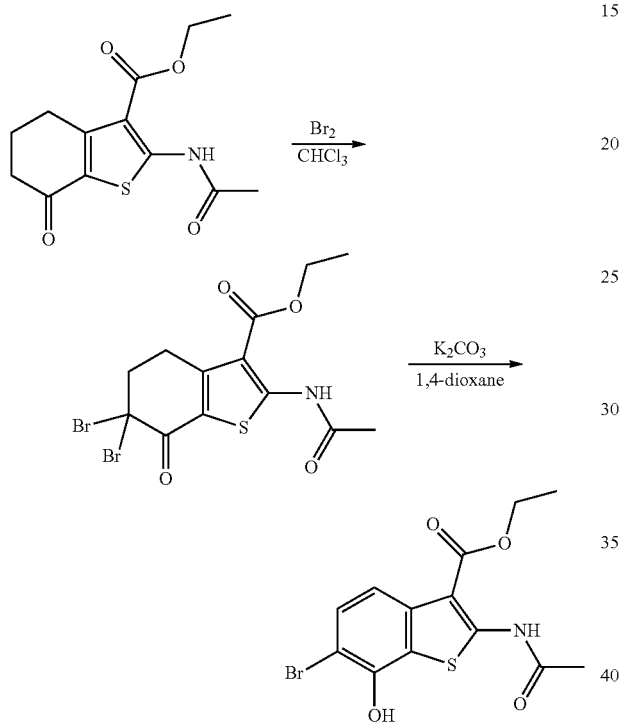

Under an argon atmosphere, a solution of bromine (1.0 mL, 19 mmol) in chloroform (5.0 mL) was slowly added to a solution of ethyl 2-acetylamino-4,5,6,7-tetrahydro-7-oxobenzo[b]thiophene-3-carboxylate (2.5 g, 8.9 mmol) in chloroform (25 mL), followed by heating under reflux (oil bath temperature: 75° C.) for 3 hours. The mixture was cooled to room temperature, and stirred at room temperature for 16 hours. Then, an aqueous sodium thiosulfate solution was added, and the product was extracted with methylene chloride (×3). The organic layer was washed with saturated aqueous sodium chloride, and dried over anhydrous sodium sulfate. After filtration, the organic layer was concentrated under vacuum, and the residue was purified by silica gel flash column chromatography (n-hexane/ethyl acetate=4/1, 1/1). Thus, ethyl 2-acetylamino-6,6-dibromo-4,5,6,7-tetrahydro-7-oxobenzo[b]thiophene-3-carboxylate (2.9 g, 6.6 mmol, 74%) was obtained as a white solid. Next, under an argon atmosphere, a solution of potassium carbonate (1.4 g, 10 mmol) in water (3.0 mL) was added to a solution of ethyl 2-acetylamino-6,6-dibromo-4,5,6,7-tetrahydro-7-oxobenzo[b]thiophene-3-carboxylate (2.9 g, 6.6 mmol) in 1,4-dioxane (15 mL), followed by heating under reflux (oil bath temperature: 120° C.) for 30 minutes. The formed gray precipitates were collected by filtration, and washed with methanol.

Thus, ethyl 2-acetylamino-6-bromo-7-hydroxybenzo[b]thiophene-3-carboxylate (2.2 g, 6.1 mmol, 93%) was obtained as a gray solid: TLC $R_f$=0.20 (n-hexane/ethyl acetate=2/1); $^1$H NMR (500 MHz, CDCl$_3$) δ 1.50 (t, J=7.0 Hz, 3H), 2.36 (s, 3H), 4.48 (q, J=7.0 Hz, 2H), 5.89 (s, 1H), 7.45 (d, J=8.5 Hz, 1H), 7.74 (d, J=8.5 Hz, 1H), 11.71 (br s, 1H); $^{13}$C NMR (126 MHz, CDCl$_3$) δ 14.6, 24.1, 61.4, 103.3, 106.4, 117.1, 121.5, 129.4, 135.6, 146.7, 153.5, 166.7, 168.3.

(7) Synthesis of Ethyl 2-Acetylamino-6-bromo-7-[2-(N,N-diethylamino)ethyloxy]benzo[b]thiophene-3-carboxylate (compound #09)

[Chem. 26]

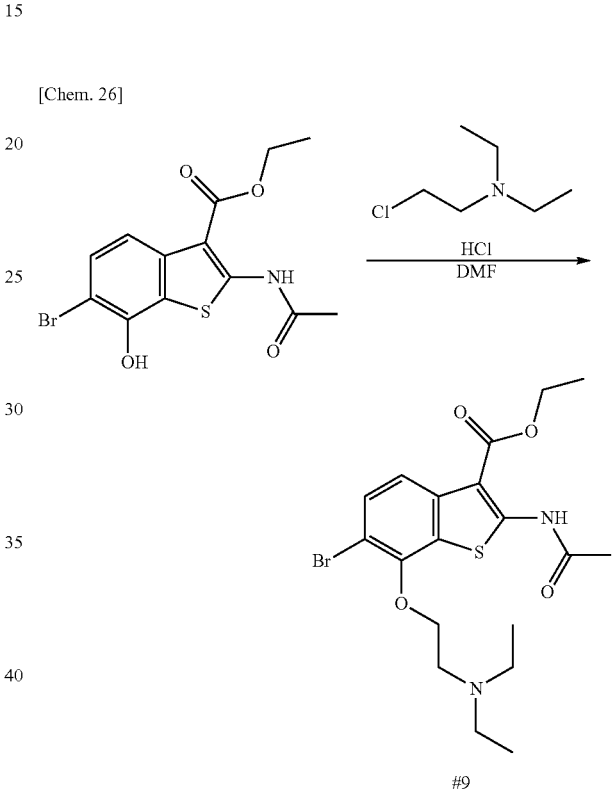

Under an argon atmosphere, potassium carbonate (403 mg, 2.9 mmol) and N-(2-chloroethyl)diethylamine hydrochloric acid salt (341 mg, 2.0 mmol) were added to a solution of ethyl 2-acetylamino-6-bromo-7-hydroxybenzo[b]thiophene-3-carboxylate (331 mg, 0.93 mmol) in N,N-dimethylformamide (5.0 mL), followed by stirring at 100° C. for 12 hours. After filtration, the mixture was concentrated under vacuum, and the residue was purified by silica gel flash column chromatography (methylene chloride/methanol=50/1, 10/1). Thus, ethyl 2-acetylamino-6-bromo-7-[2-(N,N-diethylamino)ethyloxy]benzo[b]thiophene-3-carboxylate (190 mg, 45%) was obtained as a light brown solid: TLC $R_f$=0.56 (methylene chloride/methanol=10/1); $^1$H NMR (500 MHz, CDCl$_3$) δ 1.13 (br t, J=7.0 Hz, 6H), 1.50 (t, J=7.0 Hz, 3H), 2.36 (s, 3H), 2.70-2.79 (br, 4H), 3.04-3.09 (br, 2H), 4.27 (t, J=6.5 Hz, 2H), 4.48 (q, J=7.0 Hz, 2H), 7.53 (d, J=8.5 Hz, 1H), 7.88 (d, J=8.5 Hz, 1H), 11.70 (br s, 1H); $^{13}$C NMR (126 MHz, CDCl$_3$) δ 11.9, 14.6, 24.1, 47.8, 52.6, 61.5, 71.6 (br), 106.6, 110.3, 120.4, 129.1, 131.1, 135.3, 150.5, 153.1, 166.6, 168.3.

(8) Synthesis of Ethyl 2-Amino-7-[2-(N,N-diethylamino)ethyloxy]-6-bromobenzo[b]thiophene-3-carboxylate (TMD-460)

[Chem. 27]

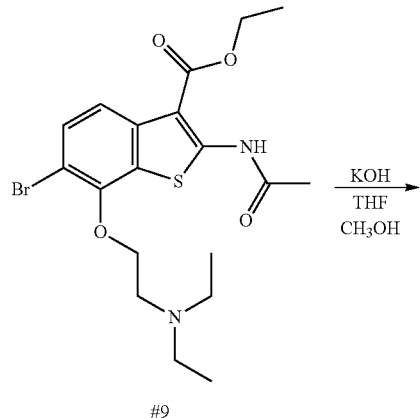

(9) Synthesis of Ethyl 2-Acetylamino-7-[2-(N,N-diethylamino)ethyloxy]-6-phenylbenzo[b]thiophene-3-carboxylate (TMD-459)

[Chem. 28]

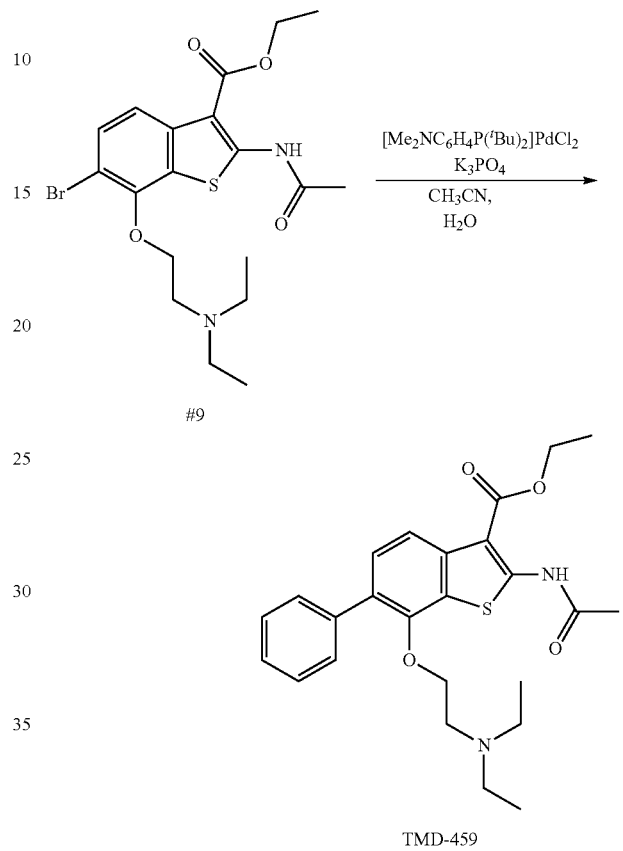

Under an argon atmosphere, an aqueous sodium hydroxide solution (1.0 M, 0.20 mL, 0.20 mmol) was added at 0° C. to a solution of ethyl 2-acetylamino-6-bromo-7-[2-(N,N-diethylamino)ethyloxy]benzo[b]thiophene-3-carboxylate (compound #09) (46 mg, 0.10 mmol) in a mixture of THF (2.0 mL) and methanol (2.0 mL). After stirring for 1 hour, the mixture was concentrated, and purified by preparative thin-layer chromatography (eluent: methylene chloride/methanol=10/1). Thus, ethyl 2-amino-7-[2-(N,N-diethylamino)ethyloxy]-6-bromobenzo[b]thiophene-3-carboxylate (TMD-460) (32.5 mg, 78%) was obtained as a brown oily liquid: TLC $R_f$=0.37 (methylene chloride/methanol=10/1); $^1$H NMR (500 MHz, CDCl$_3$) δ 1.09 (t, $J$=7.0 Hz, 6H), 1.44 (t, $J$=7.0 Hz, 3H), 2.69 (q, $J$=7.0 Hz, 4H), 2.98 (t, $J$=6.5 Hz, 2H), 4.18 (t, $J$=6.5 Hz, 2H), 4.40 (q, $J$=7.0 Hz, 2H), 6.63 (br s, 2H), 7.42 (d, $J$=8.5 Hz, 1H), 7.69 (d, $J$=8.5 Hz, 1H); $^{13}$C NMR (126 MHz, CDCl$_3$) δ 12.0, 14.8, 47.8, 52.7, 60.3, 71.5, 100.3, 108.4, 119.5, 123.8, 130.9, 138.9, 149.8, 164.8, 166.2.

Under an argon atmosphere, a solution of ethyl 2-acetylamino-6-bromo-7-[2-(N,N-diethylamino)ethyloxy]benzo[b]thiophene-3-carboxylate (compound #09) (22 mg, 50 μmol), phenylboronic acid (10 mg, 0.10 mmol), potassium phosphate n hydrate (23 mg, ca. 1 mmol), and bis[di-t-butyl(4-dimethylaminophenyl)phosphine]dichloropalladium (1.8 mg, 2.5 μmol) in acetonitrile (1.0 mL) and water (0.10 mL) was stirred at 100° C. for 12 hours. After filtration, the solution was concentrated under vacuum, and the residue was purified by preparative thin-layer chromatography (eluent: methylene chloride/methanol=10/1). Thus, ethyl 2-acetylamino-7-[2-(N,N-diethylamino)ethyloxy]-6-phenylbenzo[b]thiophene-3-carboxylate (TMD-459) (18 mg, 82%) was obtained as a yellow solid. This solid was recrystallized from acetonitrile to obtain colorless crystals: TLC $R_f$=0.56 (methylenechloride/methanol=10/1); $^1$H NMR (500 MHz, CDCl$_3$) δ 0.85-0.99 (br, 6H), 1.55 (t, $J$=7.0 Hz, 3H), 2.39 (s, 3H), 2.41-2.56 (br, 4H), 2.66-2.75 (br, 2H), 3.70-3.79 (br, 2H), 4.53 (q, $J$=7.0 Hz, 2H), 7.32-7.48 (m, 4H), 7.65 (d, $J$=7.5 Hz, 2H), 8.07 (d, $J$=8.5 Hz, 1H), 11.78 (br s, 1H); $^{13}$C NMR (126 MHz, CDCl$_3$) δ 11.8 (br), 14.6, 24.2, 47.6, 52.5 (br), 61.3, 71.2 (br), 106.7, 119.3, 127.4, 128.58, 128.63, 129.0, 129.40, 129.43, 135.2, 138.3, 150.9, 153.3, 166.9, 168.2.

Then, the thus obtained novel benzothiophene compounds (TMD-459 and TMD-460) were evaluated for the ability to induce alternative autophagy by the same method as that described in Example 1. Note that, in Example 10, each of the compounds was added to culture liquids at final concentrations of 10, 20, 30, 40, and 50 μM. In addition, compound #9 was also added as a reference example to culture liquids at the above-described concentrations. Then, 5 hours after the addition of each of these compounds, five visual fields per each well were photographed at random with IN CELL ANALYZER 1000, and the presence or absence of fluorescent bright spots due to the aggregation of Lamp1-GFP was visually determined.

As a result, although not shown in the figures, aggregation of the Lamp1-GFP was observed in all the cells in the observed visual fields after the stimulation with each of compound #9, TMD-459, and TMD-460 at concentrations of 10 μM or higher. Hence, it has been found that each of these benzothiophene compounds has ability to induce alternative autophagy.

Example 11

The cell death-inducing activity of each of TMD-460 and compound #09 was evaluated by a method shown below.

First, wild-type mouse embryonic fibroblasts (MEFs) immortalized by introducing SV40T antigen were seeded at $2 \times 10^4$/well and primary MEFs were seeded at $2 \times 10^4$/well on 96-well plates. Then, on the following day, each of the compounds was added at final concentrations of 10, 20, 30, 40, and 50 μM. In addition, a negative control to which only DMSO was added was also prepared. Subsequently, the cells were cultured at 37° C. under 10% $CO_2$ for 24 hours. Then, by using CTB according to the attached protocol, the amount of the fluorescence of each well of the cells 10 minutes after the addition of the CTB reagent was obtained as a CTB measurement value of the cells brought into contact with TMD-460 or compound #09. On the basis of such measurement values, the cell death induction rate of each compound was calculated according to the following formula.

Cell death induction rate=(CTB measurement value of negative control−CTB measurement value of cells to which compound was added)/CTB measurement value of negative control Table 2 shows the obtained results.

TABLE 2

|  | 10 μM | 20 μM | 30 μM | 40 μM | 50 μM |
|---|---|---|---|---|---|
| Compound #09 | 0.742581 | 0.887028 | 0.890025 | 0.891337 | 0.88478 |
| TMD-460 | 0.770121 | 0.875037 | 0.888527 | 0.890213 | 0.891899 |

As is apparent from the results shown in Table 2, it was found that the stimulation with each of TMD-460 and compound #09 at a final concentration 20 μM for 24 hours successfully induced cell death in 80% or more of the MEFs immortalized with SV40T antigen.

Example 12

Novel benzothiophene compounds (TMD-473, TMD-511 to TMD-520, TMD-593, and TMD-594) having the following structural formulae were designed and synthesized as analogous compounds of compound #09.

[Chem. 29]

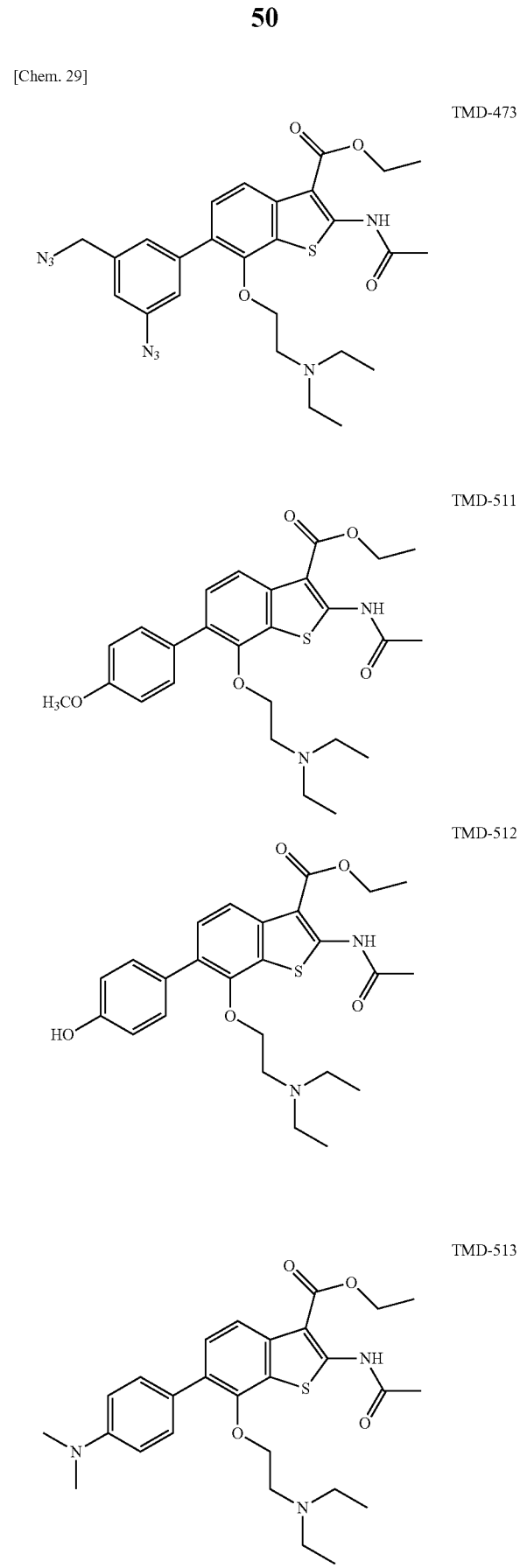

-continued
TMD-514
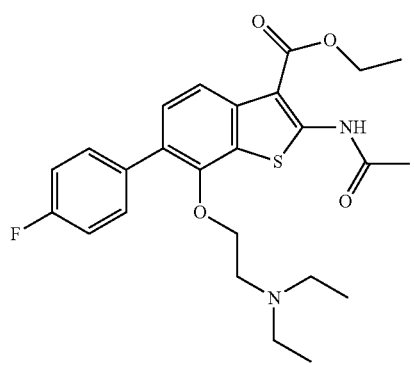
TMD-515
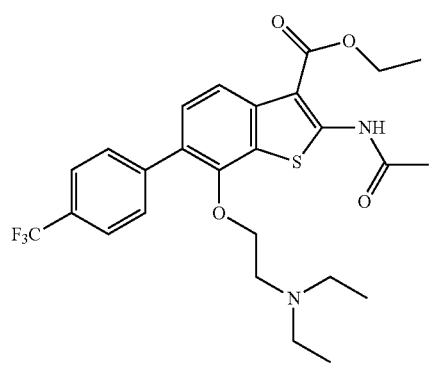
TMD-516
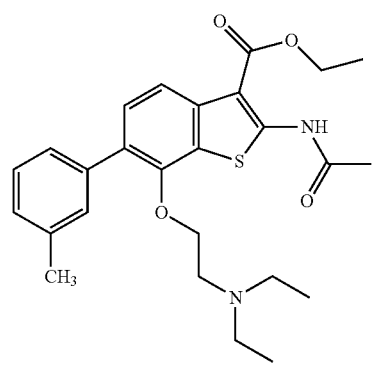
TMD-517
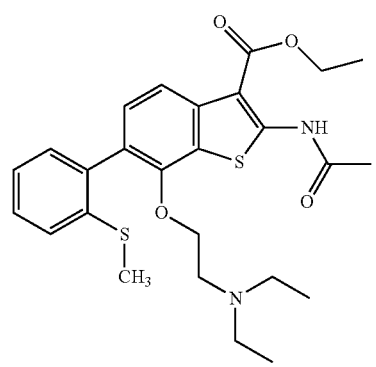
-continued
TMD-518
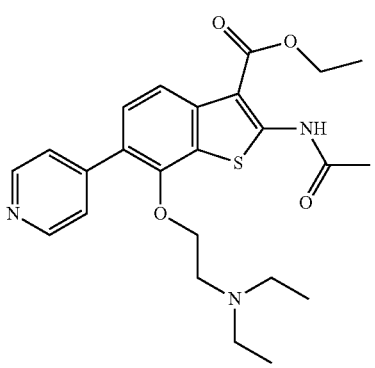
TMD-519
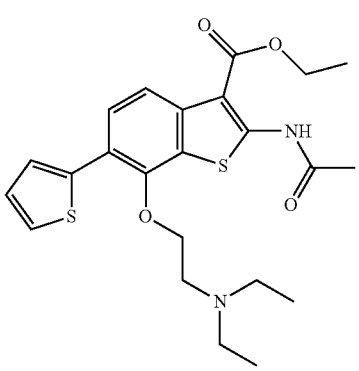
TMD-520
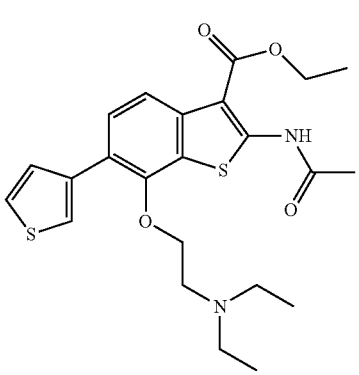
TMD-593
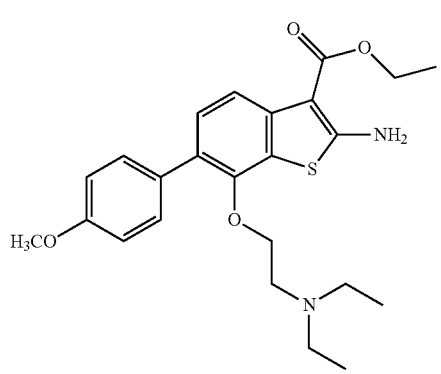

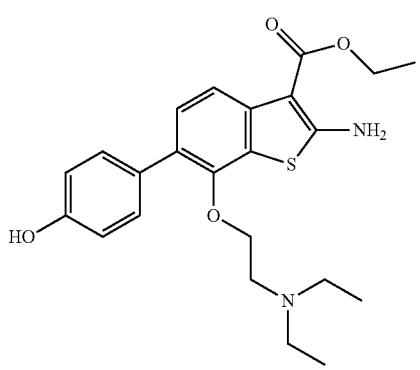

TMD-594

(10) Synthesis of Ethyl 2-Acetylamino-7-[2-(N,N-diethylamino)ethyloxy]-6-(3-azido-5-azidomethylphenyl)benzo[b]thiophene-3-carboxylate (TMD-473)

[Chem. 30]

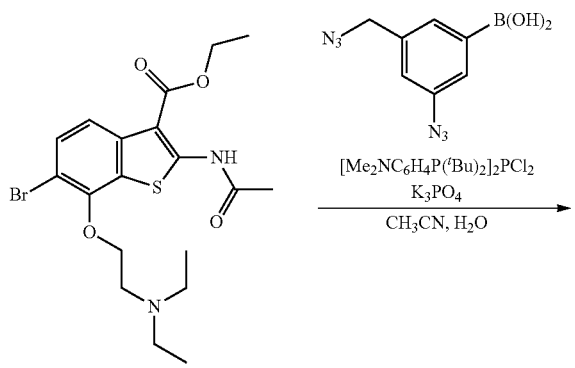

TMD-473

In the above-described formula, "Me" represents a methyl group ($CH_3$ group) (hereinafter the same shall apply).

Under an argon atmosphere, a solution of ethyl 2-acetylamino-6-bromo-7-[2-(N,N-diethylamino)ethyloxy]benzo[b]thiophene-3-carboxylate (compound #09) (23 mg, 50 μmol), 3-azido-5-azidomethylphenylboronic acid (22 mg, 0.10 mmol), potassium phosphate n hydrate (23 mg, ca. 1 mmol), and bis[di-t-butyl(4-dimethylaminophenyl)phosphine]dichloropalladium (1.8 mg, 3.0 μmol) in acetonitrile (1.0 mL) and water (0.10 mL) was stirred at 80° C. for 12 hours. After filtration, the solution was concentrated under vacuum, and the residue was purified by preparative thin-layer chromatography (eluent: methylene chloride/methanol=10/1). Thus, ethyl 2-acetylamino-7-[2-(N,N-diethylamino)ethyloxy]-6-(3-azido-5-azidomethylphenyl)benzo[b]thiophene-3-carboxylate (TMD-473) (23 mg, 84%) was obtained as a yellow solid. This solid was recrystallized from acetonitrile to obtain colorless crystals: TLC Rf=0.61 (methylene chloride/methanol=10/1); $^1$H NMR (400 MHz, $CDCl_3$) δ 0.92-0.97 (br, 6H), 1.52 (t, J=7.2 Hz, 3H), 2.37 (s, 3H), 2.45-2.50 (br, 4H), 2.68-2.74 (br, 2H), 3.72-3.79 (br, 2H), 4.40 (s, 2H), 4.50 (q, J=7.2 Hz, 2H), 7.00 (s, 1H), 7.31 (s, 1H), 7.38 (s, 1H), 7.39 (d, J=8.4 Hz, 1H), 8.06 (d, J=8.4 Hz, 1H), 11.75 (br s, 1H).

(11) Synthesis of Ethyl 2-acetylamino-7-[2-(N,N-diethylamino)ethyloxy]-6-(4-methoxyphenyl)benzo[b]thiophene-3-carboxylate (TMD-511)

[Chem. 31]

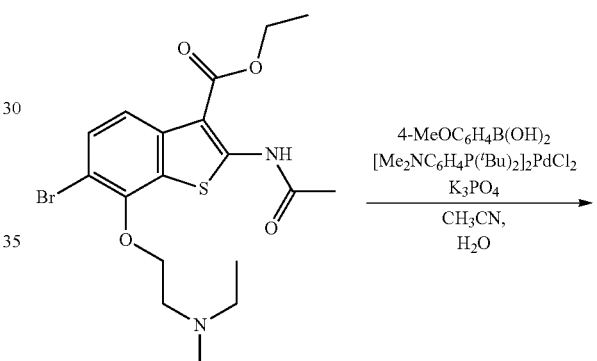

TDM-511

Under an argon atmosphere, a solution of ethyl 2-acetylamino-6-bromo-7-[2-(N,N-diethylamino)ethyloxy]benzo[b]thiophene-3-carboxylate (compound #09) (23 mg, 51 μmol), 4-methoxyphenylboronic acid (15 mg, 0.10 mmol), potassium phosphate n hydrate (23 mg, ca. 1 mmol), and bis[di-t-butyl(4-dimethylaminophenyl)phosphine]dichloropalladium (1.7 mg, 2.5 μmol) in acetonitrile (1.0 mL) and water (0.10 mL) was stirred at 80° C. for 12 hours. After filtration, the solution was concentrated under vacuum, and the residue was purified by preparative thin-layer chromatography (eluent: methylene chloride/methanol=10/1). Thus, ethyl 2-acetylamino-7-[2-(N,N-diethylamino)ethyloxy]-6-(4-methoxyphenyl)benzo[b]thiophene-3-carboxylate (TMD-511) (23 mg, 96%) was obtained as a yellow solid. This solid was recrystallized from acetonitrile to obtain colorless crystals: TLC Rf=0.47 (methylenechloride/methanol=10/1); 1H NMR (400 MHz, CDCl$_3$) δ 0.95 (t, $J$=7.2 Hz, 6H), 1.52 (t, $J$=7.2 Hz, 3H), 2.36 (s, 3H), 2.48 (q, $J$=7.2 Hz, 4H), 2.71 (t, $J$=6.8 Hz, 2H), 3.75 (t, $J$=6.8 Hz, 2H), 3.86 (s, 3H), 4.50 (q, $J$=7.2 Hz, 2H), 6.96-7.00 (AA' BB', 2H), 7.39 (d, $J$=8.4 Hz, 1H), 7.55-7.59 (AA' BB', 2H), 8.02 (d, $J$=8.4 Hz, 1H), 11.74 (br s, 1H).

(12) Synthesis of Ethyl 2-acetylamino-7-[2-(N,N-diethylamino)ethyloxy]-6-(4-hydroxyphenyl)benzo[b]thiophene-3-carboxylate (TMD-512)

Thus, ethyl 2-acetylamino-7-[2-(N,N-diethylamino)ethyloxy]-6-(4-hydroxyphenyl)benzo[b]thiophene-3-carboxylate (TMD-512) (16 mg, 68%) was obtained as a yellow solid. This solid was recrystallized from acetonitrile to obtain colorless crystals: TLC Rf=0.22 (methylenechloride/methanol=10/1); 1H NMR (400 MHz, CDCl$_3$) δ 1.05 (t, $J$=7.2 Hz, 6H), 1.52 (t, $J$=7.2 Hz, 3H), 2.36 (s, 3H), 2.65 (q, $J$=7.2 Hz, 4H), 2.87 (t, $J$=6.4 Hz, 2H), 3.86 (t, $J$=6.4 Hz, 2H), 4.50 (q, $J$=7.2 Hz, 2H), 6.86-6.89 (AA' BB', 2H), 7.38 (d, $J$=8.4 Hz, 1H), 7.46-7.49 (AA' BB', 2H), 8.03 (d, $J$=8.4 Hz, 1H), 11.74 (br s, 1H).

(13) Synthesis of Ethyl 2-Acetylamino-7-[2-(N,N-diethylamino)ethyloxy]-6-(4-di methylaminophenyl)benzo[b]thiophene-3-carboxylate (TMD-513)

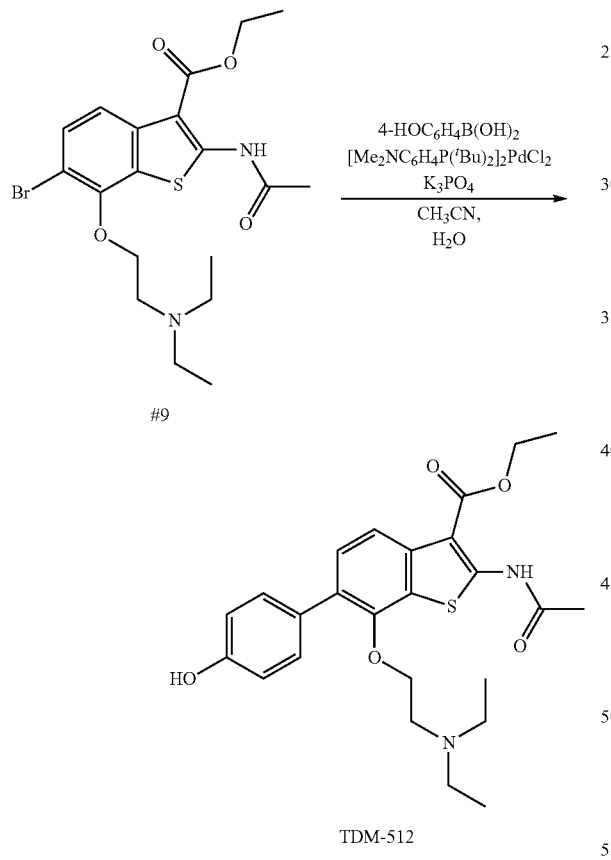

TDM-512

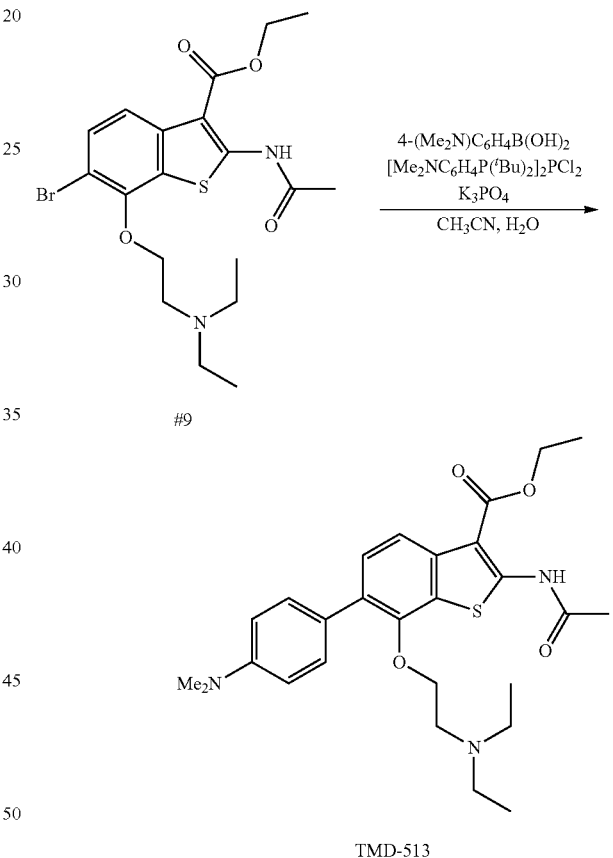

TMD-513

Under an argon atmosphere, a solution of ethyl 2-acetylamino-6-bromo-7-[2-(N,N-diethylamino)ethyloxy]benzo[b]thiophene-3-carboxylate (compound #09) (23 mg, 51 µmol), 4-hydroxyphenylboronic acid (14 mg, 0.10 mmol), potassium phosphate n hydrate (23 mg, ca. 1 mmol), and bis[di-t-butyl(4-dimethylaminophenyl)phosphine]dichloropalladium (1.4 mg, 2.0 µmol) in acetonitrile (2.0 mL) and water (0.20 mL) was stirred at 80° C. for 12 hours. After filtration, the solution was concentrated under vacuum, and the residue was purified by preparative thin-layer chromatography (eluent: methylene chloride/methanol=10/1).

Under an argon atmosphere, a solution of ethyl 2-acetylamino-6-bromo-7-[2-(N,N-diethylamino)ethyloxy]benzo[b]thiophene-3-carboxylate (compound #09) (22 mg, 50 µmol), 4-dimethylaminophenylboronic acid (17 mg, 0.10 mmol), potassium phosphate n hydrate (23 mg, ca. 1 mmol), and bis[di-t-butyl(4-dimethylaminophenyl)phosphine]dichloropalladium (1.7 mg, 3.0 µmol) in acetonitrile (1.0 mL) and water (0.10 mL) was stirred at 80° C. for 12 hours. After filtration, the solution was concentrated under vacuum, and the residue was purified by preparative thin-layer chromatography (eluent: methylene chloride/methanol=10/1). Thus, ethyl 2-acetylamino-7-[2-(N,N-diethylamino)ethyloxy]-6-(4-di methylaminophenyl)benzo[b]thiophene-3-carboxylate (TMD-513) (14 mg, 57%) was obtained as a brown solid: TLC Rf=0.39 (methylene chloride/methanol=10/1); 1H NMR (400 MHz, CDCl$_3$) δ 0.95 (t, J=7.2 Hz, 6H), 1.50 (t, J=7.2 Hz, 3H), 2.35 (s, 3H), 2.49 (q, J=7.2 Hz, 4H), 2.73 (t, J=6.8 Hz, 2H), 3.00 (s, 6H), 3.77 (t, J=6.8 Hz, 2H), 4.49 (q, J=7.2 Hz, 2H), 6.79-6.82 (AA' BB', 2H), 7.40 (d, J=8.4 Hz, 1H), 7.52-7.55 (AA' BB', 2H), 8.00 (d, J=8.4 Hz, 1H), 11.72 (br s, 1H).

(14) Synthesis of Ethyl 2-acetylamino-7-[2-(N,N-diethylamino)ethyloxy]-6-(4-fluorophenyl)benzo[b]thiophene-3-carboxylate (TMD-514)

[Chem. 34]

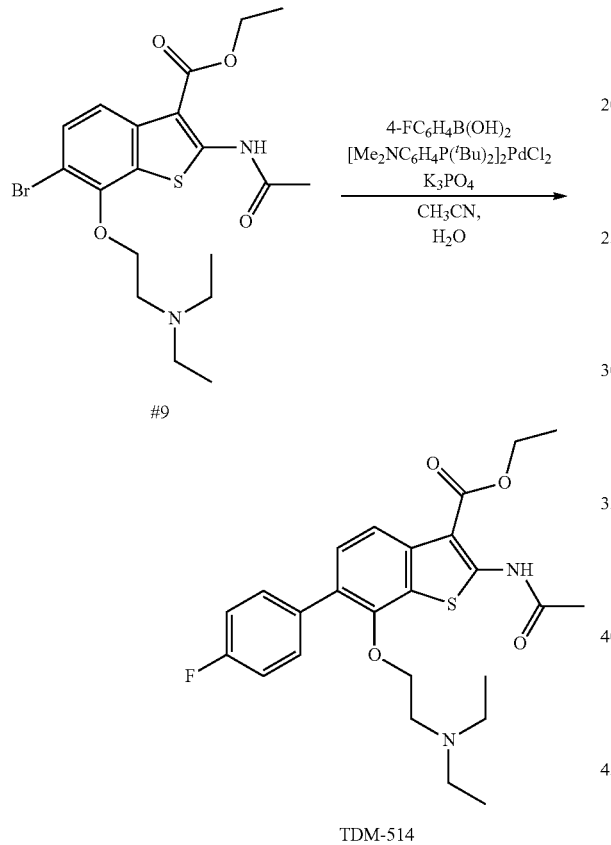

TDM-514

Under an argon atmosphere, a solution of ethyl 2-acetylamino-6-bromo-7-[2-(N,N-diethylamino)ethyloxy]benzo[b]thiophene-3-carboxylate (compound #09) (24 mg, 51 μmol), 4-fluorophenylboronic acid (15 mg, 0.10 mmol), potassium phosphate n hydrate (23 mg, ca. 1 mmol), and bis[di-t-butyl(4-dimethylaminophenyl)phosphine]dichloropalladium (1.6 mg, 2.5 μmol) in acetonitrile (2.0 mL) and water (0.20 mL) was stirred at 80° C. for 12 hours. After filtration, the solution was concentrated under vacuum, and the residue was purified by preparative thin-layer chromatography (eluent: methylene chloride/methanol=10/1). Thus, ethyl 2-acetylamino-7-[2-(N,N-diethylamino)ethyloxy]-6-(4-fluorophenyl)benzo[b]thiophene-3-carboxylate (TMD-514) (22 mg, 92%) was obtained as a yellow solid. This solid was recrystallized from acetonitrile to obtain colorless crystals: TLC Rf=0.50 (methylenechloride/methanol=10/1); 1H NMR (400 MHz, CDCl$_3$) δ 0.94 (t, J=7.2 Hz, 6H), 1.52 (t, J=7.2 Hz, 3H), 2.36 (s, 3H), 2.45 (q, J=7.2 Hz, 4H), 2.69 (t, J=6.8 Hz, 2H), 3.73 (t, J=6.8 Hz, 2H), 4.50 (q, J=7.2 Hz, 2H), 7.10-7.16 (m, 2H), 7.37 (d, J=8.4 Hz, 1H), 7.58-7.63 (m, 2H), 8.04 (d, J=8.4 Hz, 1H), 11.74 (br s, 1H).

(15) Synthesis of Ethyl 2-acetylamino-7-[2-(N,N-diethylamino)ethyloxy]-6-(4-trifluoromethylphenyl)benzo[b]thiophene-3-carboxylate (TMD-515)

[Chem. 35]

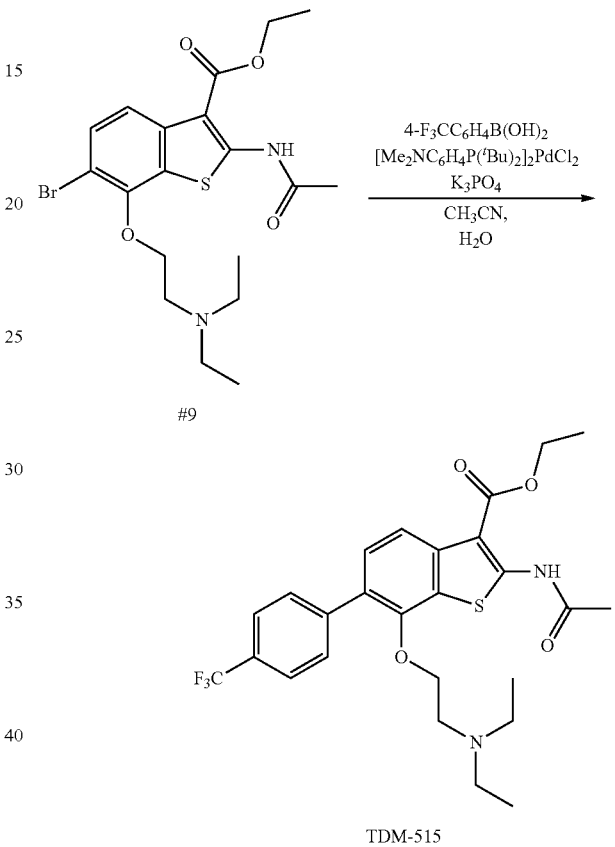

TDM-515

Under an argon atmosphere, a solution of ethyl 2-acetylamino-6-bromo-7-[2-(N,N-diethylamino)ethyloxy]benzo[b]thiophene-3-carboxylate (compound #09) (23 mg, 50 μmol), 4-trifluoromethylphenylboronic acid (19 mg, 0.10 mmol), potassium phosphate n hydrate (20 mg, ca. 1 mmol), and bis[di-t-butyl(4-dimethylaminophenyl)phosphine]dichloropalladium (1.6 mg, 2.3 μmol) in acetonitrile (2.0 mL) and water (0.20 mL) was stirred at 80° C. for 12 hours. After filtration, the solution was concentrated under vacuum, and the residue was purified by preparative thin-layer chromatography (eluent: methylene chloride/methanol=10/1). Thus, ethyl 2-acetylamino-7-[2-(N,N-diethylamino)ethyloxy]-6-(4-trifluoromethylphenyl)benzo[b]thiophene-3-carboxylate (TMD-515) (6.2 mg, 24%) was obtained as a brown solid: TLC Rf=0.56 (methylene chloride/methanol=10/1); 1H NMR (400 MHz, CDCl$_3$) δ 0.88-0.96 (br, 6H), 1.52 (t, J=7.2 Hz, 3H), 2.37 (s, 3H), 2.38-2.48 (br, 4H), 2.66-2.72 (br, 2H), 3.70-3.75 (br, 2H), 4.51 (q, J=7.2 Hz, 2H), 7.40 (d, J=8.4 Hz, 1H), 7.68-7.71 (AA' BB', 2H), 7.75-7.78 (AA' BB', 2H), 8.08 (d, J=8.4 Hz, 1H), 11.76 (br s, 1H).

(16) Synthesis of Ethyl 2-Acetylamino-7-[2-(N,N-diethylamino)ethyloxy]-6-(3-methylphenyl)benzo[b]thiophene-3-carboxylate (TMD-516)

[Chem. 36]

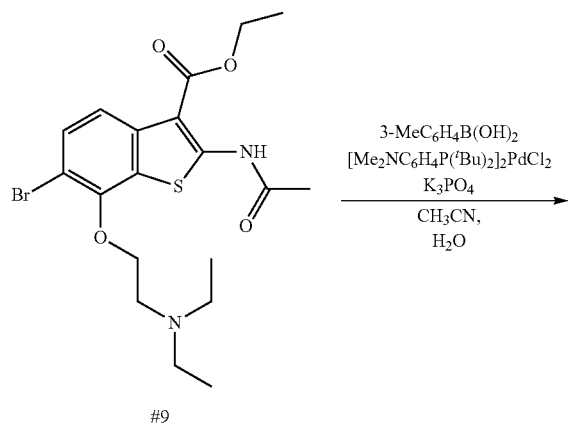

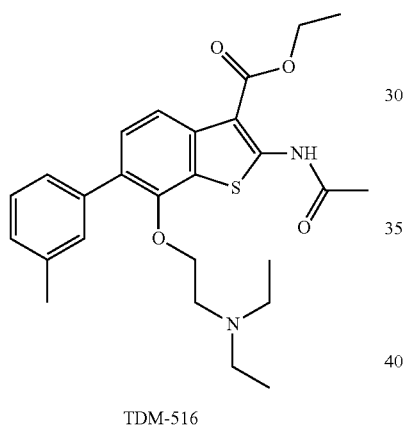

TDM-516

Under an argon atmosphere, a solution of ethyl 2-acetylamino-6-bromo-7-[2-(N,N-diethylamino)ethyloxy]benzo[b]thiophene-3-carboxylate (compound #09) (24 mg, 52 μmol), 3-methylphenylboronic acid (14 mg, 0.10 mmol), potassium phosphate n hydrate (23 mg, ca. 1 mmol), and bis[di-t-butyl(4-dimethylaminophenyl)phosphine]dichloropalladium (1.6 mg, 2.5 μmol) in acetonitrile (1.0 mL) and water (0.10 mL) was stirred at 80° C. for 12 hours. After filtration, the solution was concentrated under vacuum, and the residue was purified by preparative thin-layer chromatography (eluent: methylene chloride/methanol=10/1). Then, ethyl 2-acetylamino-7-[2-(N,N-diethylamino)ethyloxy]-6-(3-methylphenyl)benzo[b]thiophene-3-carboxylate (TMD-516) (22 mg, 90%) was obtained as a yellow solid. This solid was recrystallized from acetonitrile to obtain colorless crystals: TLC Rf=0.42 (methylenechloride/methanol=10/1); 1H NMR (400 MHz, CDCl$_3$) δ 0.93 (t, J=7.2 Hz, 6H), 1.52 (t, J=7.2 Hz, 3H), 2.17 (s, 3H), 2.36 (s, 3H), 2.46 (q, J=7.2 Hz, 4H), 2.70 (t, J=6.8 Hz, 2H), 3.74 (t, J=6.8 Hz, 2H), 4.50 (q, J=7.2 Hz, 2H), 7.16 (d, J=7.6 Hz, 1H), 7.32 (dd, J=7.6, 7.6 Hz, 1H), 7.39-7.52 (m, 3H), 8.03 (d, J=8.4 Hz, 1H), 11.74 (br s, 1H).

(17) Synthesis of Ethyl 2-acetylamino-7-[2-(N,N-diethylamino)ethyloxy]-6-(2-methylthiophenyl)benzo[b]thiophene-3-carboxylate (TMD-517)

[Chem. 37]

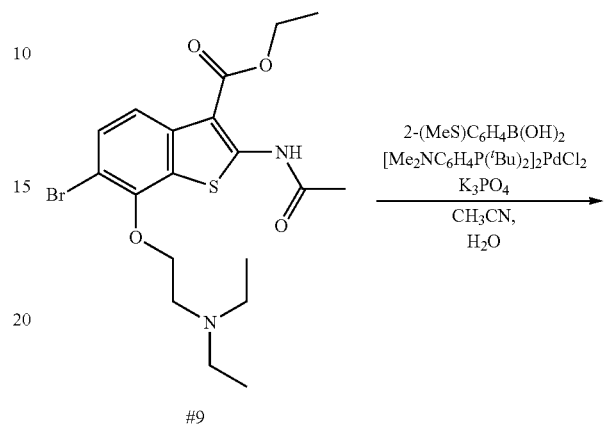

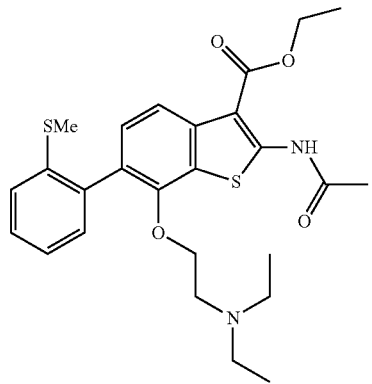

TDM-517

Under an argon atmosphere, a solution of ethyl 2-acetylamino-6-bromo-7-[2-(N,N-diethylamino)ethyloxy]benzo[b]thiophene-3-carboxylate (compound #09) (23 mg, 50 μmol), 2-methylthiophenylboronic acid (17 mg, 0.10 mmol), potassium phosphate n hydrate (23 mg, ca. 1 mmol), and bis[di-t-butyl(4-dimethylaminophenyl)phosphine]dichloropalladium (1.6 mg, 2.5 μmol) in acetonitrile (2.0 mL) and water (0.20 mL) was stirred at 80° C. for 12 hours. After filtration, the solution was concentrated under vacuum, and the residue was purified by preparative thin-layer chromatography (eluent: methylene chloride/methanol=10/1). Thus, ethyl 2-acetylamino-7-[2-(N,N-diethylamino)ethyloxy]-6-(2-methylthiophenyl)benzo[b]thiophene-3-carboxylate (TMD-517) (18 mg, 73%) was obtained as a brown solid: TLC Rf=0.36 (methylene chloride/methanol=10/1); 1H NMR (400 MHz, CDCl$_3$) δ 0.90 (t, J=7.2 Hz, 6H), 1.50 (t, J=7.2 Hz, 3H), 2.17 (s, 3H), 2.35-2.42 (m, 5H), 2.61 (t, J=6.8 Hz, 2H), 3.74-2.83 (br, 2H), 4.49 (q, J=7.2 Hz, 2H), 7.20 (ddd, J=1.2, 7.2, 7.2 Hz, 1H), 7.27-7.39 (m, 4H), 8.03 (d, J=8.0 Hz, 1H), 11.76 (br s, 1H).

(18) Synthesis of Ethyl 2-acetylamino-7-[2-(N,N-diethylamino)ethyloxy]-6-(4-pyridyl)benzo[b]thiophene-3-carboxylate (TMD-518)

[Chem. 38]

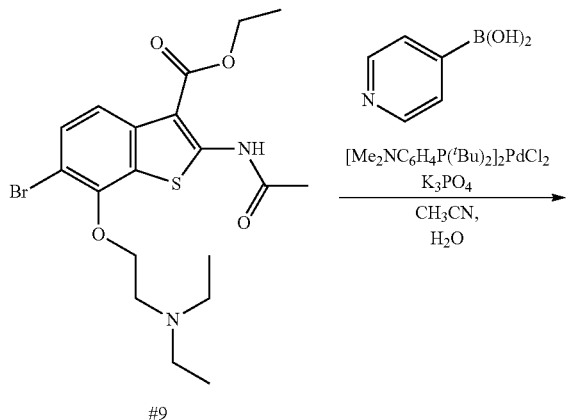

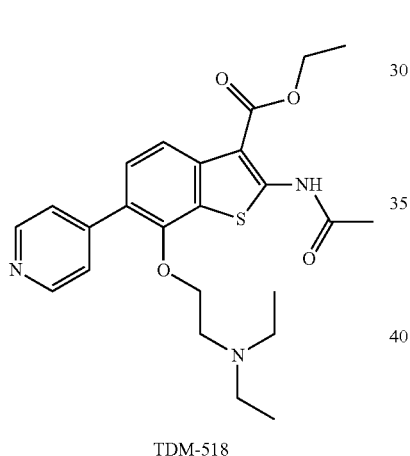

TDM-518

Under an argon atmosphere, a solution of ethyl 2-acetylamino-6-bromo-7-[2-(N,N-diethylamino)ethyloxy]benzo[b]thiophene-3-carboxylate (compound #09) (24 mg, 53 µmol), 4-pyridylboronic acid (12 mg, 0.10 mmol), potassium phosphate n hydrate (23 mg, ca. 1 mmol), and bis[di-t-butyl(4-dimethylaminophenyl)phosphine]dichloropalladium (1.6 mg, 2.5 µmol) in acetonitrile (2.0 mL) and water (0.20 mL) was stirred at 80° C. for 12 hours. After filtration, the solution was concentrated under vacuum, and the residue was purified by preparative thin-layer chromatography (eluent: methylene chloride/methanol=10/1). Thus, ethyl 2-acetylamino-7-[2-(N,N-diethylamino)ethyloxy]-6-(4-pyridyl)benzo[b]thiophene-3-carboxylate (TMD-518) (6.0 mg, 26%) was obtained as a brown solid: TLC Rf=0.22 (methylene chloride/methanol=10/1); 1H NMR (400 MHz, CDCl₃) δ 0.96 (t, J=7.2 Hz, 6H), 1.53 (t, J=7.2 Hz, 3H), 2.37 (s, 3H), 2.50 (q, J=7.2 Hz, 4H), 2.75 (t, J=6.8 Hz, 2H), 3.80 (t, J=6.8 Hz, 2H), 4.51 (q, J=7.2 Hz, 2H), 7.42 (d, J=8.4 Hz, 1H), 7.59-7.62 (AA' BB', 2H), 8.09 (d, J=8.4 Hz, 1H), 8.66-8.68 (AA' BB', 2H), 11.76 (br s, 1H).

(19) Synthesis of Ethyl 2-acetylamino-7-[2-(N,N-diethylamino)ethyloxy]-6-(2-thienyl)benzo[b]thiophene-3-carboxylate (TMD-519)

[Chem. 39]

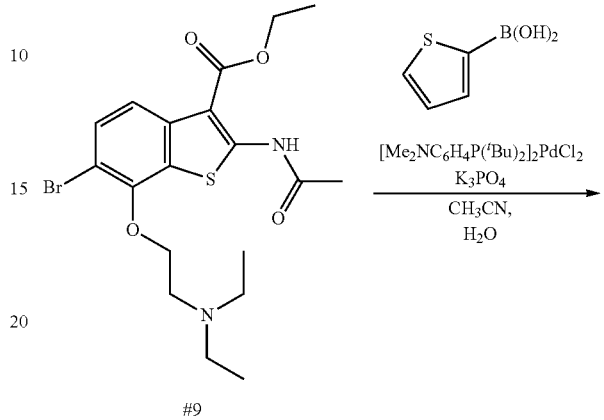

TDM-519

Under an argon atmosphere, a solution of ethyl 2-acetylamino-6-bromo-7-[2-(N,N-diethylamino)ethyloxy]benzo[b]thiophene-3-carboxylate (compound #09) (23 mg, 51 µmol), 2-thienylboronic acid (13 mg, 0.10 mmol), potassium phosphate n hydrate (23 mg, ca. 1 mmol), and bis[di-t-butyl(4-dimethylaminophenyl)phosphine]dichloropalladium (1.8 mg, 3.0 µmol) in acetonitrile (1.0 mL) and water (0.10 mL) was stirred at 80° C. for 12 hours. After filtration, the solution was concentrated under vacuum, and the residue was purified by preparative thin-layer chromatography (eluent: methylene chloride/methanol=10/1). Thus, ethyl 2-acetylamino-7-[2-(N,N-diethylamino)ethyloxy]-6-(2-thienyl)benzo[b]thiophene-3-carboxylate (TMD-519) (20 mg, 87%) was obtained as a yellow solid. This solid was recrystallized from acetonitrile to obtain colorless crystals: TLC Rf=0.42 (methylenechloride/methanol=10/1); 1H NMR (400 MHz, CDCl₃) δ 1.04 (t, J=7.2 Hz, 6H), 1.52 (t, J=7.2 Hz, 3H), 2.36 (s, 3H), 2.60 (q, J=7.2 Hz, 4H), 2.94 (t, J=6.8 Hz, 2H), 4.01 (t, J=6.8 Hz, 2H), 4.49 (q, J=7.2 Hz, 2H), 7.11 (dd, J=3.6, 5.2 Hz, 1H), 7.35 (dd, J=1.2, 5.2 Hz, 1H), 7.51 (dd, J=1.2, 3.6 Hz, 1H), 7.64 (d, J=8.4 Hz, 1H), 8.01 (d, J=8.4 Hz, 1H), 11.73 (br s, 1H).

(20) Synthesis of Ethyl 2-acetylamino-7-[2-(N,N-diethylamino)ethyloxy]-6-(3-thienyl)benzo[b]thiophene-3-carboxylate (TMD-520)

[Chem. 40]

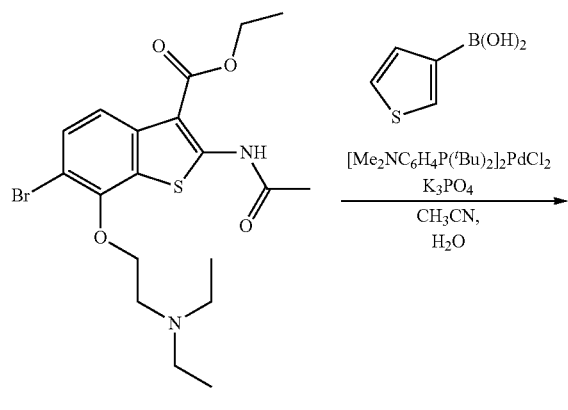

9

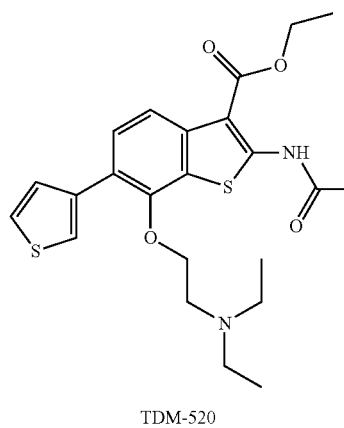

TDM-520

Under an argon atmosphere, a solution of ethyl 2-acetylamino-6-bromo-7-[2-(N,N-diethylamino)ethyloxy]benzo[b]thiophene-3-carboxylate (compound #09) (23 mg, 50 µmol), 3-thienylboronicacid (13 mg, 0.10 mmol), potassium phosphate n hydrate (23 mg, ca. 1 mmol), and bis[di-t-butyl (4-dimethylaminophenyl)phosphine]dichloropalladium (1.8 mg, 3.0 µmol) in acetonitrile (1.0 mL) and water (0.10 mL) was stirred at 80° C. for 12 hours. After filtration, the solution was concentrated under vacuum, and the residue was purified by preparative thin-layer chromatography (eluent: methylene chloride/methanol=10/1). Thus, ethyl 2-acetylamino-7-[2-(N,N-diethylamino)ethyloxy]-6-(3-thienyl)benzo[b]thiophene-3-carboxylate (TMD-520) (20 mg, 86%) was obtained as a yellow solid. This solid was recrystallized from acetonitrile to obtain colorless crystals: TLC Rf=0.42 (methylenechloride/methanol=10/1); 1H NMR (400 MHz, CDCl$_3$) δ 1.00 (t, J=7.2 Hz, 6H), 1.52 (t, J=7.2 Hz, 3H), 2.36 (s, 3H), 2.54 (q, J=7.2 Hz, 4H), 2.81 (t, J=6.8 Hz, 2H), 3.85 (t, J=6.8 Hz, 2H), 4.50 (q, J=7.2 Hz, 2H), 7.38 (dd, J=2.8, 5.2 Hz, 1H), 7.49-7.54 (m, 2H), 7.67 (dd, J=1.2, 2.8 Hz, 1H), 8.02 (d, J=8.4 Hz, 1H), 11.73 (br s, 1H).

(21) Synthesis of Ethyl 2-amino-7-[2-(N,N-diethylamino)ethyloxy]-6-(4-methoxyphenyl)benzo[b]thiophene-3-carboxylate (TMD-593)

[Chem. 41]

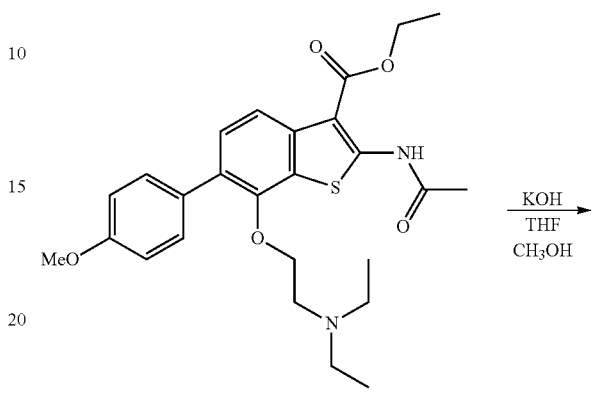

TMND-511

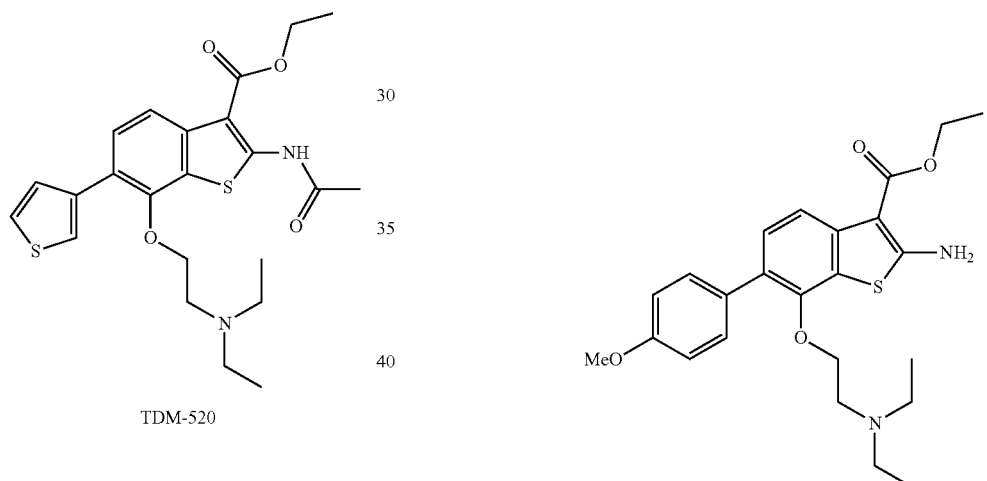

TMD-593

Under an argon atmosphere, an aqueous sodium hydroxide solution (1.0 M, 0.10 mL, 0.10 mmol) was added at room temperature to a solution of ethyl 2-acetylamino-7-[2-(N,N-diethylamino)ethyloxy]-6-(4-methoxyphenyl)benzo[b]thiophene-3-carboxylate (TMD-511) (9.7 mg, 20 µmol) in a mixture of THF (1.0 mL) and methanol (1.0 mL). After stirring for 1 hour, the mixture was concentrated, and purified by preparative thin-layer chromatography (eluent: methylene chloride/methanol=10/1). Thus, ethyl 2-amino-7-[ 2-(N,N-diethylamino)ethyloxy]-6-(4-methoxyphenyl)benzo[b]thiophene-3-carboxylate (TMD-593) (8.2 mg, 93%) was obtained as a yellow solid: TLC Rf=0.22 (methylene chloride/methanol=10/1); 1H NMR (400 MHz, CDCl$_3$) δ 0.98-1.02 (br, 6H), 1.44 (t, J=7.2 Hz, 3H), 2.48-2.60 (br, 4H), 2.66-2.73 (br, 2H), 3.70-3.75 (br, 2H), 3.86 (s, 3H), 4.42 (q, J=7.2 Hz, 2H), 6.55 (br s, 2H), 6.95-6.98 (AA' BB', 2H), 7.26 (d, J=8.0 Hz, 1H), 7.51-7.54 (AA' BB', 2H), 7.85 (d, J=8.0 Hz, 1H).

(22) Synthesis of Ethyl 2-amino-7-[2-(N,N-diethyl-amino)ethyloxy]-6-(4-hydroxyphenyl)benzo[b]thiophene-3-carboxylate (TMD-594)

[Chem. 42]

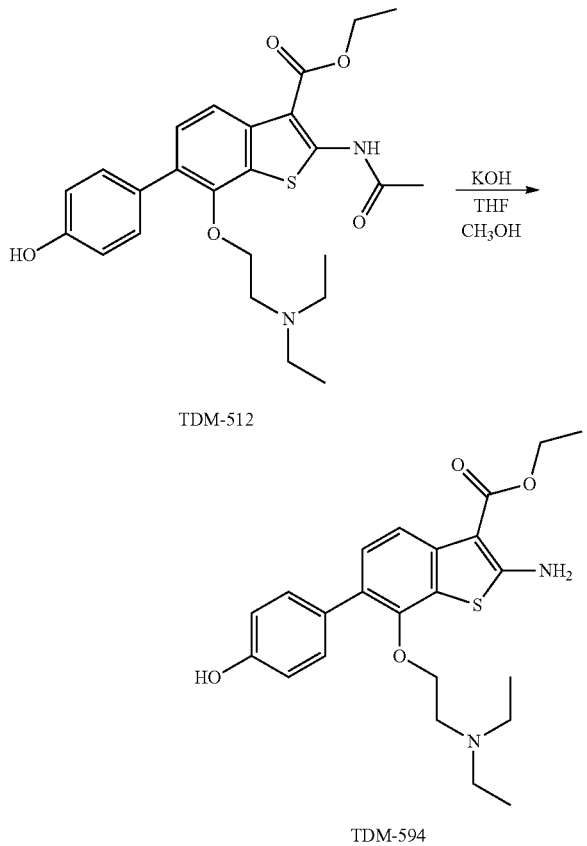

Under an argon atmosphere, an aqueous sodium hydroxide solution (1.0 M, 0.10 mL, 0.10 mmol) was added at room temperature to a solution of ethyl 2-acetylamino-7-[2-(N,N-diethylamino)ethyloxy]-6-(4-hydroxyphenyl)benzo[b]thiophene-3-carboxylate (TMD-512) (9.4 mg, 20 μmol) in a mixture of THF (1.0 mL) and methanol (1.0 mL). After stirring for 1 hour, the mixture was concentrated, and purified by preparative thin-layer chromatography (eluent: methylene chloride/methanol=10/1). Thus, ethyl 2-amino-7-[2-(N,N-diethylamino)ethyloxy]-6-(4-hydroxyphenyl) benzo[b]thiophene-3-carboxylate (TMD-594) (8.1 mg, 95%) was obtained as a colorless solid: TLC Rf=0.17 (methylene chloride/methanol=10/1); 1H NMR (400 MHz, CDCl$_3$) δ 1.03 (t, $J$=7.2 Hz, 3H), 1.46 (t, $J$=7.2 Hz, 3H), 2.55-2.62 (br, 4H), 2.71-2.75 (br, 2H), 3.74-3.78 (br, 2H), 4.43 (q, $J$=7.2 Hz, 2H), 6.57 (br s, 2H), 6.86-6.89 (AA' BB', 2H), 7.26 (d, $J$=8.4 Hz, 1H), 7.44-7.47 (AA' BB', 2H), 7.85 (d, $J$=8.4 Hz, 1H).

Example 13

Figure 18:
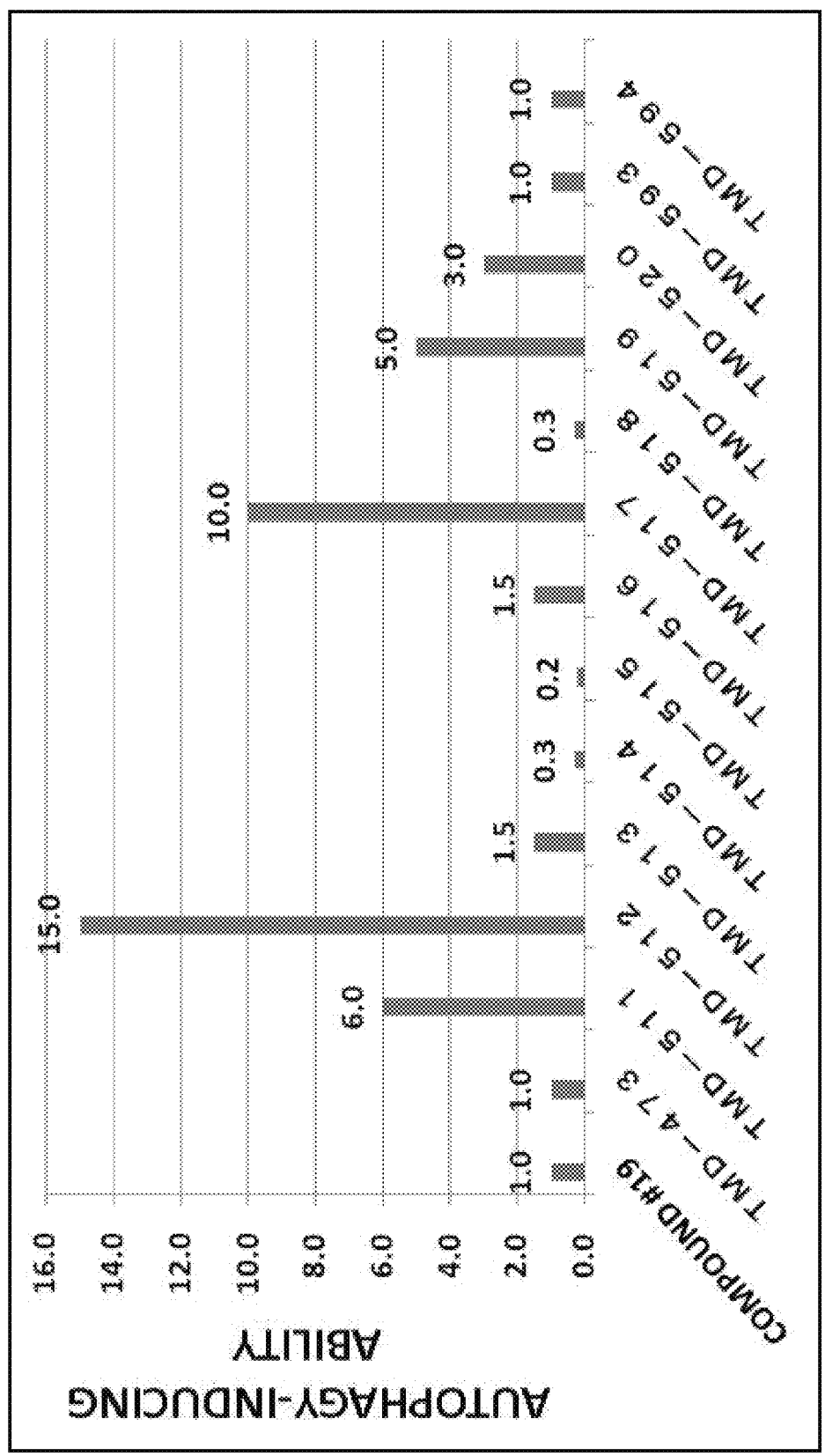
FIG. 18 is a graph showing ability to induce alternative autophagy of each of compound #09 and analogous compounds thereof (TMD-473, TMD-511 to 520, TMD-593, and TMD-594). Note that, in the graph, the vertical axis represents the relative activity value obtained by evaluating the autophagy area per cell in each of the cases where these compounds were added, with the autophagy area in the case where compound #09 was added taken as 1.

The ability to induce alternative autophagy of each of compound #09 and the analogous compounds thereof (TMD-473, TMD-511 to TMD-520, TMD-593, and TMD-594) was evaluated by the same method as that described in Example 1. FIG. 18 shows the obtained results.

As is apparent from the results shown in FIG. 18, it was found that each of the benzothiophene compounds (TMD-473, TMD-511 to TMD-520, TMD-593, and TMD-594) had ability to induce alternative autophagy.

INDUSTRIAL APPLICABILITY

As described above, according to the present invention, it is possible to provide an alternative autophagy-inducing agent and an anticancer agent comprising a benzothiophene compound as an active ingredient. Accordingly, the anticancer agent comprising the benzothiophene compound of the present invention as an active ingredient is useful for treatment and prevention (recurrence prevention) of various types of cancer, and particularly useful for treatment and the like of cancer which has acquired resistance to apoptosis.

In addition, in the present invention, it is possible to achieve efficient screening for a compound having anticancer activity by using activity to induce alternative autophagy as an index. Hence, the screening method of the present invention is useful for development of an agent for treatment or prevention (recurrence prevention) of various types of cancer, and particularly for development of an agent for treatment or the like of cancer which has acquired resistance to apoptosis.

The invention claimed is:

1. A method for inducing alternative autophagy, comprising
introducing a benzothiophene compound represented by the following general formula (1) into any one of a cultured cell and an animal:

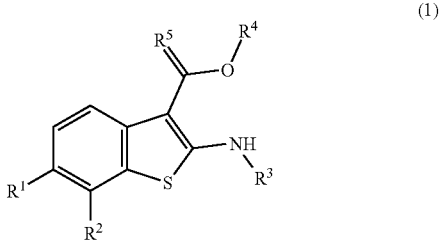

(1)

in the formula (1), R$^1$ is an optionally substituted 5- to 10-membered aromatic carbon ring, an optionally substituted 5- to 10-membered aromatic heterocycle, or a group represented by —R$^6$—R$^7$, R$^2$ is a halogen atom, a hydroxyl group, or a group represented by —O—R$^6$—R$^7$ or —O—R$^6$—R$^8$, R$^3$ is a hydrogen atom or a group represented by —C(=O)R$^9$, R$^4$ is a linear, branched, or cyclic alkyl group having 1 to 6 carbon atoms, and R$^5$ is an oxygen atom or an imino group, and also in the formula (1), R$^6$s, which may be the same or different, each independently is a linear, branched, or cyclic alkylene group having 1 to 6 carbon atoms, R$^7$s, which may be the same or different, each independently is an amino group optionally substituted by a linear, branched, or cyclic alkyl group having 1 to 6 carbon atoms, a linear, branched, or cyclic alkenyl group having 2 to 6 carbon atoms, or a linear, branched, or cyclic hydroxyalkyl group having 1 to 6 carbon atoms, R$^8$ is an optionally substituted 5- to 10-membered aromatic carbon ring or an optionally substituted 5- to 10-membered aromatic heterocycle, and R$^9$ is a linear, branched, or cyclic alkyl group having 1 to 6 carbon atoms, an optionally substituted 5- to 10-membered aromatic carbon ring, or an optionally substituted 5- to 10-membered aromatic heterocycle, and inducing alternative autophagy in any one of the cultured cell or the animal.

2. At least one benzothiophene compound selected from the group consisting of the following (a) and (b):
(a) a benzothiophene compound represented by the following general formula (1):

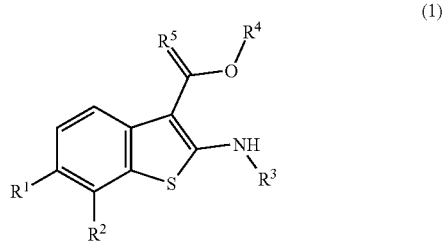
(1)

in the formula (1), $R^1$ is an optionally substituted 5- to 10-membered aromatic carbon ring or an optionally substituted 5- to 10-membered aromatic heterocycle, $R^2$ is a halogen atom, a hydroxyl group, or a group represented by —O—$R^6$—$R^7$ or —O—$R^6$—$R^8$, $R^3$ is a hydrogen atom or a group represented by —C(=O)$R^9$, $R^4$ is a linear, branched, or cyclic alkyl group having 1 to 6 carbon atoms, and $R^5$ is an oxygen atom or an imino group, and also in the formula (1), $R^6$ is a linear, branched, or cyclic alkylene group having 1 to 6 carbon atoms, $R^7$ is an amino group optionally substituted by a linear, branched, or cyclic alkyl group having 1 to 6 carbon atoms, a linear, branched, or cyclic alkenyl group having 2 to 6 carbon atoms, or a linear, branched, or cyclic hydroxyalkyl group having 1 to 6 carbon atoms, $R^8$ is an optionally substituted 5- to 10-membered aromatic carbon ring or an optionally substituted 5- to 10-membered aromatic heterocycle, and $R^9$ is a linear, branched, or cyclic alkyl group having 1 to 6 carbon atoms, an optionally substituted 5- to 10-membered aromatic carbon ring, or an optionally substituted 5- to 10-membered aromatic heterocycle; and
(b) a benzothiophene compound represented by the general formula (1):
in the formula (1), $R^1$ is a halogen atom, $R^2$ is a halogen atom or a group represented by —O—$R^6$—$R^7$, $R^3$ is a group represented by a hydrogen atom, $R^4$ is a linear, branched, or cyclic alkyl group having 1 to 6 carbon atoms, and $R^5$ is an oxygen atom or an imino group, and also in the formula (1), $R^6$ is a linear, branched, or cyclic alkylene group having 1 to 6 carbon atoms, and $R^7$ is an amino group optionally substituted by a linear, branched, or cyclic alkyl group having 1 to 6 carbon atoms, a linear, branched, or cyclic alkenyl group having 2 to 6 carbon atoms, or a linear, branched, or cyclic hydroxyalkyl group having 1 to 6 carbon atoms, and the benzothiophene compound having alternative autophagy-inducing activity.

3. An anticancer agent comprising the benzothiophene compound according to claim 2 as an active ingredient, and any one of pharmacologically acceptable carriers and media.

4. A method for treating cancer, comprising a step of administering the benzothiophene compound according to claim 2 to a patient.

5. A benzothiophene compound represented by the following general formula (1):

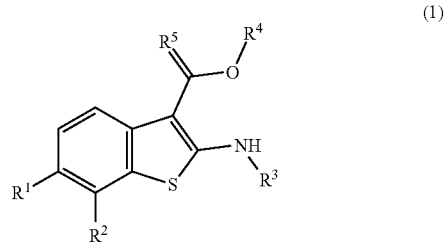
(1)

in the formula (1), $R^1$ is a group selected from the following groups

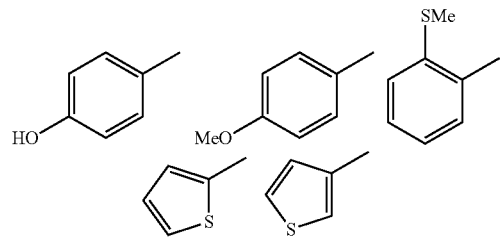

$R^2$ is a group represented by —O—$C_2H_4$—$N(C_2H_5)_2$, $R^3$ is a group represented by —C(=O) $CH_3$, $R^4$ is a group represented by —$C_2H_5$, $R^5$ is an oxygen atom.

6. An anticancer agent comprising the benzothiophene compound according to claim 5 as an active ingredient and any one of pharmacologically acceptable carriers and media.

7. A method for inducing alternative autophagy, comprising
introducing the benzothiophene compound according to claim 2 into any one of a cultured cell and an animal, and
inducing alternative autophagy in any one of the cultured cell and the animal.

* * * * *